US011039927B2

(12) United States Patent
Dee et al.

(10) Patent No.: US 11,039,927 B2
(45) Date of Patent: Jun. 22, 2021

(54) METHODS, SYSTEMS AND DEVICES FOR REPAIRING ANATOMICAL JOINT CONDITIONS

(71) Applicant: Subchondral Solutions, Inc., Los Gatos, CA (US)

(72) Inventors: Derek Dee, Los Gatos, CA (US); Chris Maurer, Los Gatos, CA (US)

(73) Assignee: SUBCHONDRAL SOLUTIONS, INC., Los Gatos, CA (US)

( * ) Notice: Subject to any disclaimer, the term of this patent is extended or adjusted under 35 U.S.C. 154(b) by 254 days.

(21) Appl. No.: 15/778,196

(22) PCT Filed: Nov. 23, 2016

(86) PCT No.: PCT/US2016/063481
§ 371 (c)(1),
(2) Date: May 22, 2018

(87) PCT Pub. No.: WO2017/091657
PCT Pub. Date: Jun. 1, 2017

(65) Prior Publication Data
US 2019/0076257 A1 Mar. 14, 2019

Related U.S. Application Data
(60) Provisional application No. 62/260,030, filed on Nov. 25, 2015.

(51) Int. Cl.
*A61F 2/30* (2006.01)
*A61B 17/16* (2006.01)
*A61F 2/46* (2006.01)

(52) U.S. Cl.
CPC ...... *A61F 2/30756* (2013.01); *A61B 17/1615* (2013.01); *A61B 17/1635* (2013.01);
(Continued)

(58) Field of Classification Search
None
See application file for complete search history.

(56) References Cited

U.S. PATENT DOCUMENTS 4,615,705 A 10/1986 Scales et al.
4,839,215 A 6/1989 Starling et al.
(Continued)

FOREIGN PATENT DOCUMENTS

BE 1015258 A5 12/2004
CN 102085114 A 6/2011
(Continued)

OTHER PUBLICATIONS

Practical haematology (Year: 2006).*
(Continued)

*Primary Examiner* — Samuel S Hanna
(74) *Attorney, Agent, or Firm* — Kilpatrick Townsend & Stockton LLP

(57) ABSTRACT

The present invention relates generally to minimally invasive, cost-effective, adaptable methods, systems, and devices used to repair anatomical joint conditions. The repair may be necessitated by trauma, disease or other conditions. The anatomical joint may specifically include mammalian joints such as the knee, shoulder, elbow, wrist, finger, hip, spine, toe and ankle, for example. The methods, systems, and devices disclosed herein include leveraging the significant (and often unappreciated) role the subchondral bone plays in the health status of the afflicted anatomical joint.

23 Claims, 33 Drawing Sheets

(52) U.S. Cl.
CPC ............ *A61B 17/1675* (2013.01); *A61F 2/30* (2013.01); *A61F 2/30771* (2013.01); *A61F 2/4618* (2013.01); *A61F 2002/305* (2013.01); *A61F 2002/3085* (2013.01); *A61F 2002/30367* (2013.01); *A61F 2002/30387* (2013.01); *A61F 2002/30405* (2013.01); *A61F 2002/30462* (2013.01); *A61F 2002/30485* (2013.01); *A61F 2002/30784* (2013.01); *A61F 2002/30841* (2013.01)

(56) References Cited

U.S. PATENT DOCUMENTS

| | | | |
|---|---|---|---|
| 5,026,373 | A | 6/1991 | Ray et al. |
| 5,306,311 | A | 4/1994 | Stone et al. |
| 5,968,098 | A * | 10/1999 | Winslow ............ A61B 17/1757 623/17.11 |
| 5,984,970 | A | 11/1999 | Bramlet |
| 6,037,519 | A | 3/2000 | McKay |
| 6,176,874 | B1 | 1/2001 | Vacanti et al. |
| 6,251,143 | B1 * | 6/2001 | Schwartz ............ A61B 17/064 623/23.72 |
| D450,122 | S | 11/2001 | Michelson |
| 6,371,958 | B1 | 4/2002 | Overaker |
| 6,520,964 | B2 | 2/2003 | Tallarida et al. |
| 6,530,958 | B1 | 3/2003 | Cima et al. |
| 6,575,986 | B2 | 6/2003 | Overaker |
| 6,579,293 | B1 | 6/2003 | Chandran |
| 6,585,770 | B1 | 7/2003 | White et al. |
| 6,712,822 | B2 | 3/2004 | Re et al. |
| 7,608,105 | B2 | 10/2009 | Pavlov et al. |
| 7,641,694 | B1 * | 1/2010 | Goble ................. A61F 2/30756 623/18.11 |
| 8,556,972 | B2 | 10/2013 | Gordon et al. |
| 8,591,592 | B2 | 11/2013 | Dreyfuss |
| 8,968,404 | B2 | 3/2015 | Dee |
| 10,610,364 | B2 | 4/2020 | Dee |
| 10,792,130 | B2 * | 10/2020 | Soler ................... A61C 8/0025 |
| 2002/0120270 | A1 | 8/2002 | Trieu et al. |
| 2003/0007957 | A1 * | 1/2003 | Britton ................. A61L 15/225 424/93.72 |
| 2004/0230315 | A1 | 11/2004 | Ek |
| 2005/0060037 | A1 | 3/2005 | Michelson |
| 2005/0164146 | A1 * | 7/2005 | Cantor ................ A61C 8/0022 433/173 |
| 2005/0266383 | A1 | 12/2005 | Aravena et al. |
| 2007/0128575 | A1 | 6/2007 | Trieu |
| 2007/0179610 | A1 | 8/2007 | Biedermann et al. |
| 2007/0244565 | A1 | 10/2007 | Stchur |
| 2007/0299450 | A1 | 12/2007 | Her et al. |
| 2008/0051796 | A1 | 2/2008 | Nycz et al. |
| 2008/0077248 | A1 | 3/2008 | Murillo et al. |
| 2008/0114400 | A1 | 5/2008 | Dant et al. |
| 2008/0154266 | A1 | 6/2008 | Protopsaltis et al. |
| 2008/0154314 | A1 * | 6/2008 | McDevitt ........... A61B 17/8095 606/304 |
| 2008/0249577 | A1 | 10/2008 | Dreyfuss |
| 2008/0262616 | A1 | 10/2008 | Mckay |
| 2008/0269747 | A1 | 10/2008 | Justin |
| 2009/0024229 | A1 | 1/2009 | Chen et al. |
| 2009/0143867 | A1 | 6/2009 | Gage et al. |
| 2009/0276053 | A1 | 11/2009 | Brown et al. |
| 2009/0298777 | A1 | 12/2009 | McKay |
| 2010/0082491 | A1 | 4/2010 | Rosenblatt et al. |
| 2010/0160984 | A1 | 6/2010 | Berry et al. |
| 2010/0168856 | A1 * | 7/2010 | Long ................... A61F 2/30756 623/14.12 |
| 2010/0191346 | A1 | 7/2010 | Bloor et al. |
| 2011/0009964 | A1 | 1/2011 | Schwartz et al. |
| 2011/0029081 | A1 | 2/2011 | Malone |
| 2011/0054529 | A1 | 3/2011 | Michelson |
| 2011/0137352 | A1 | 6/2011 | Biedermann et al. |
| 2012/0172880 | A1 * | 7/2012 | Dee ..................... A61F 2/30756 606/87 |
| 2012/0185044 | A1 * | 7/2012 | Dee ......................... A61F 2/389 623/14.12 |
| 2012/0239156 | A1 | 9/2012 | De Wilde et al. |
| 2012/0316513 | A1 | 12/2012 | Sharkey et al. |
| 2014/0379032 | A1 | 12/2014 | Hennard |
| 2015/0142121 | A1 | 5/2015 | Dee |
| 2016/0250026 | A1 | 9/2016 | Dee |
| 2017/0325914 | A1 * | 11/2017 | Tushtev ................ A61F 2/0811 |

FOREIGN PATENT DOCUMENTS

| | | | |
|---|---|---|---|
| CN | 104271055 | A | 1/2015 |
| CN | 104540476 | A | 4/2015 |
| EP | 1129675 | A2 | 9/2001 |
| GB | 2236679 | A | 4/1991 |
| JP | 10504217 | A | 4/1998 |
| JP | 2001293003 | A | 10/2001 |
| JP | 2007532149 | A | 11/2007 |
| JP | 2008539814 | A | 11/2008 |
| JP | 2015511858 | A | 4/2015 |
| WO | 2004054463 | A2 | 7/2004 |
| WO | 2008016862 | A1 | 2/2008 |
| WO | 2010144065 | A2 | 12/2010 |
| WO | WO-2016062307 | A1 * | 4/2016 ............ A61F 2/0811 |
| WO | 2017091657 | A1 | 6/2017 |

OTHER PUBLICATIONS

U.S. Appl. No. 13/420,825, Final Office Action dated Oct. 24, 2013, 13 pages.
U.S. Appl. No. 13/421,792, Notice of Allowance dated Oct. 27, 2014, 11 pages.
U.S. Appl. No. 14/603,586, Final Office Action dated May 5, 2016, 12 pages.
U.S. Appl. No. 14/603,586, Non-Final Office Action dated Nov. 10, 2015, 9 pages.
U.S. Appl. No. 15/148,894, Final Office Action dated Jan. 19, 2018, 12 pages.
U.S. Appl. No. 15/148,894, Final Office Action dated Apr. 12, 2019, 15 pages.
U.S. Appl. No. 15/148,894, Non-Final Office Action dated Aug. 1, 2018, 13 pages.
U.S. Appl. No. 15/148,894, Non-Final Office Action dated Jul. 13, 2017, 9 pages.
Chinese Patent Application No. 201280072377.7, Office Action dated Feb. 2, 2016, 14 pages.
European Patent Application No. 12871086.0, Extended European Search Report dated Sep. 23, 2015, 7 pages.
Japanese Patent Application No. 2015-500409, Office Action dated Dec. 25, 2015, 9 pages.
International Patent Application No. PCT/US2012/029291, International Search Report and Written Opinion dated Jul. 13, 2012, 9 pages.
International Application No. PCT/US2016/063481, International Search Report and Written Opinion dated Apr. 12, 2017, 44 pages.
BR112018010562-7, Office Action dated Jun. 23, 2020, 5 pages.
CN201680076499.1, Office Action dated Jul. 28, 2020, 22 pages.
EP16869218.4, Extended European Search Report dated Nov. 13, 2019, 6 pages.

* cited by examiner

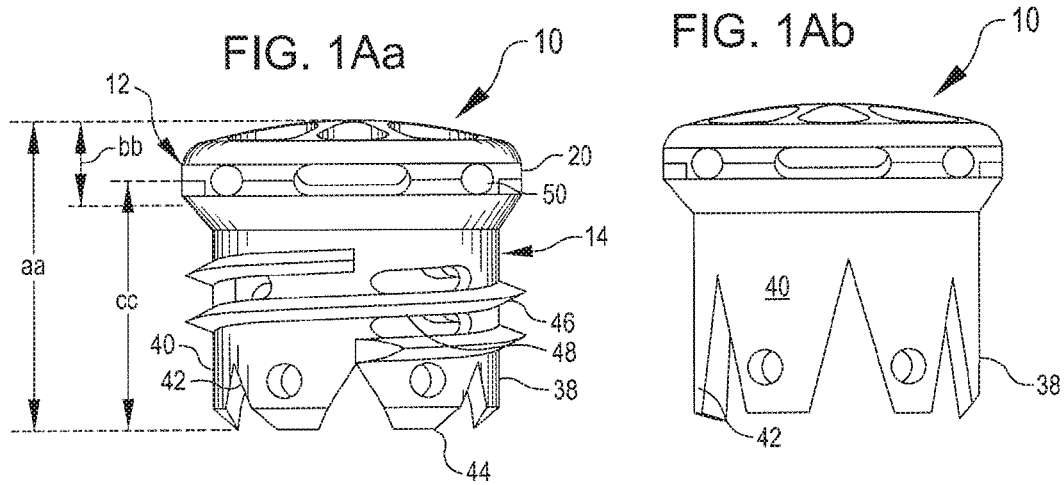
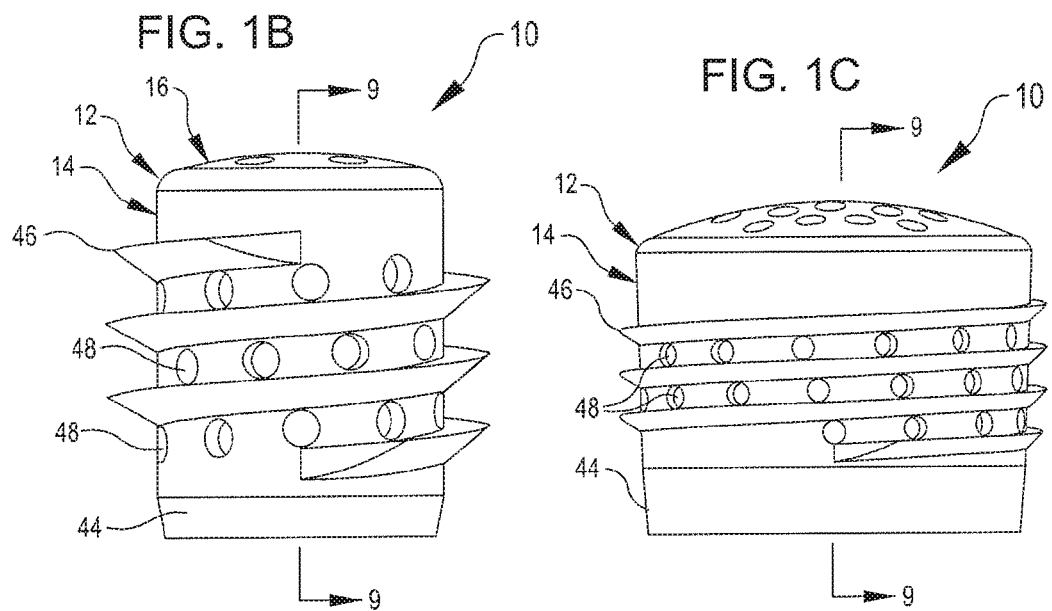
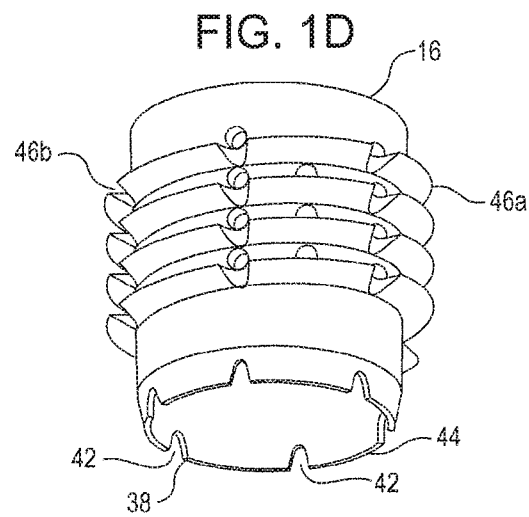

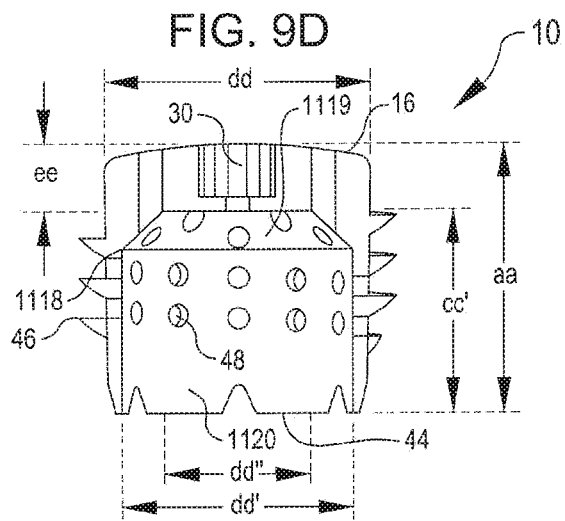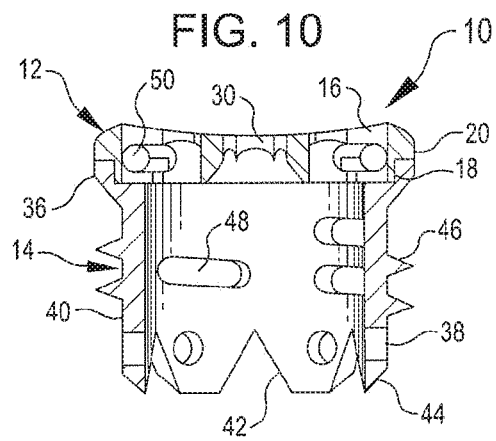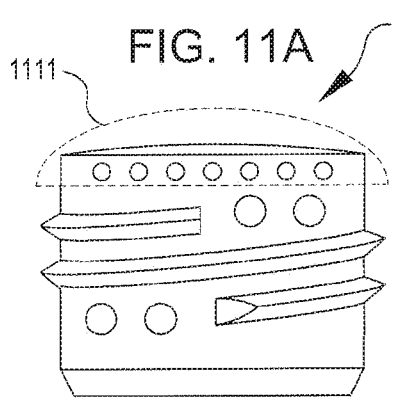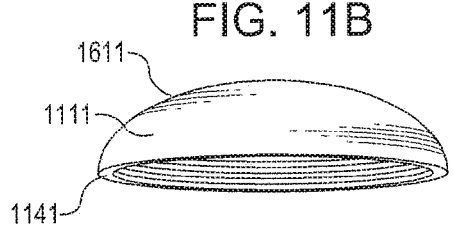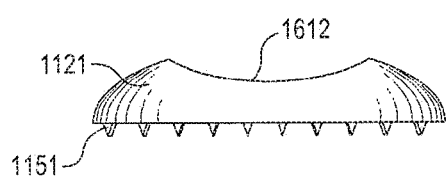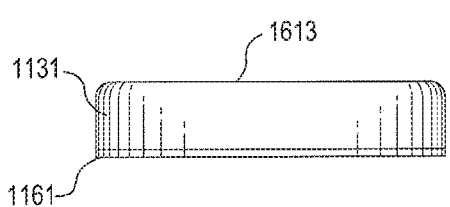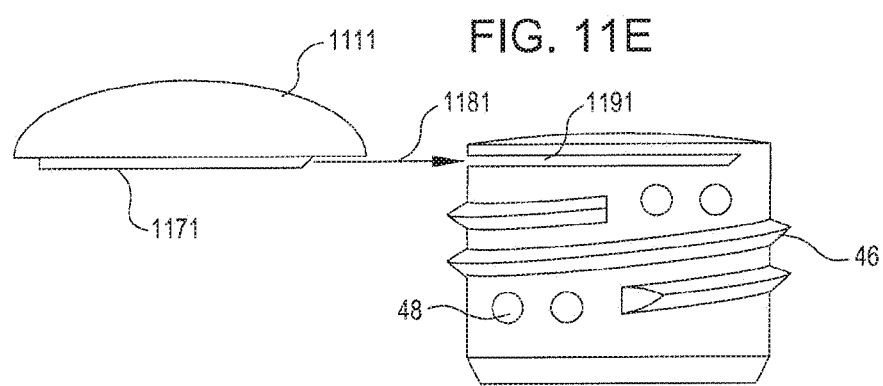

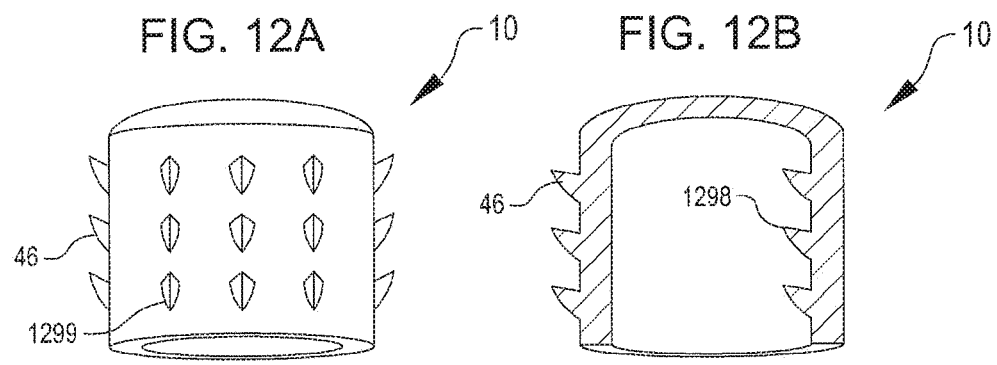
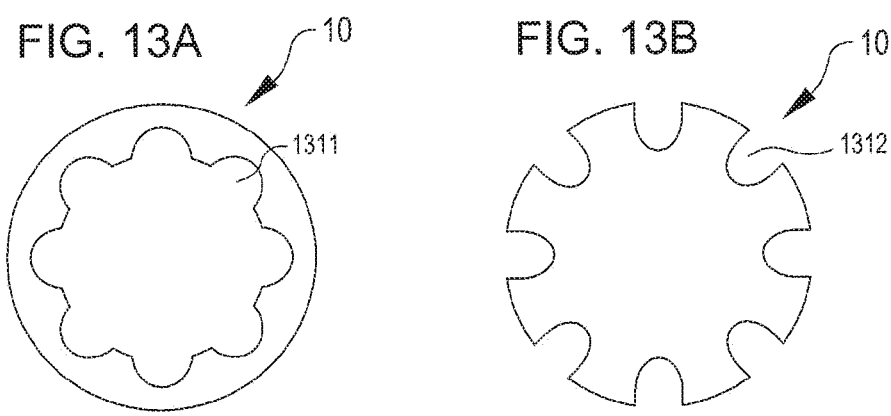
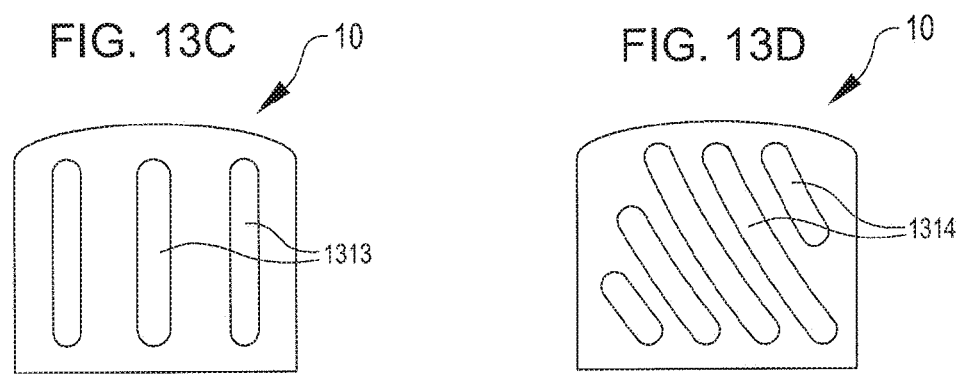

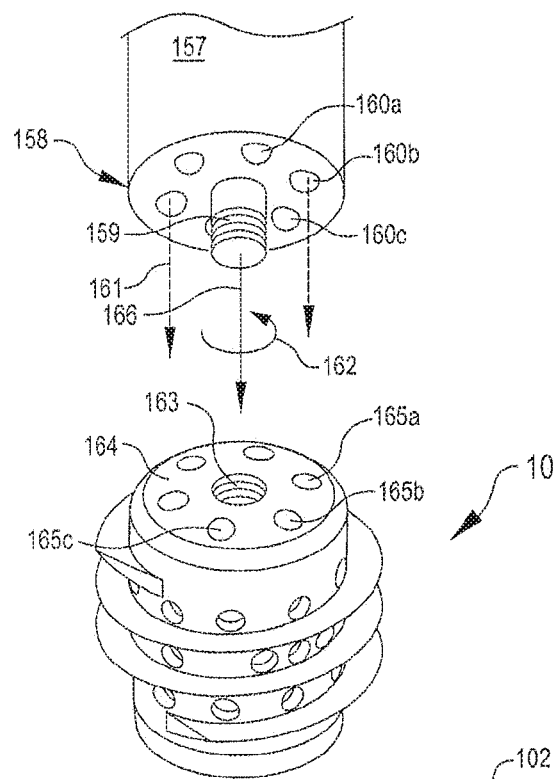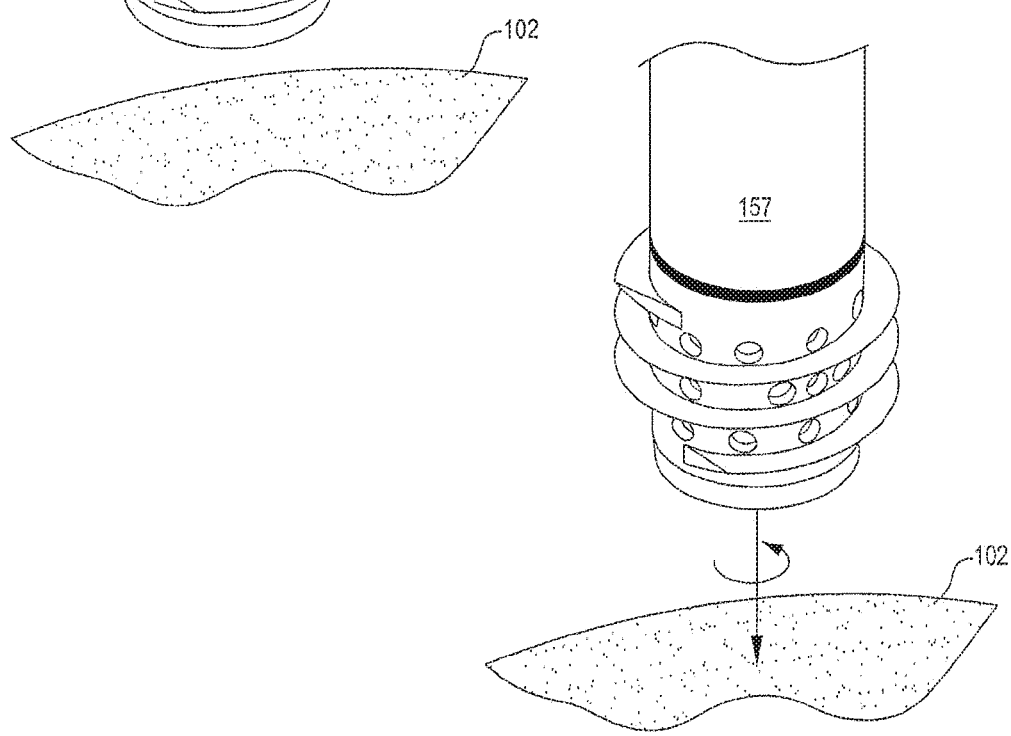

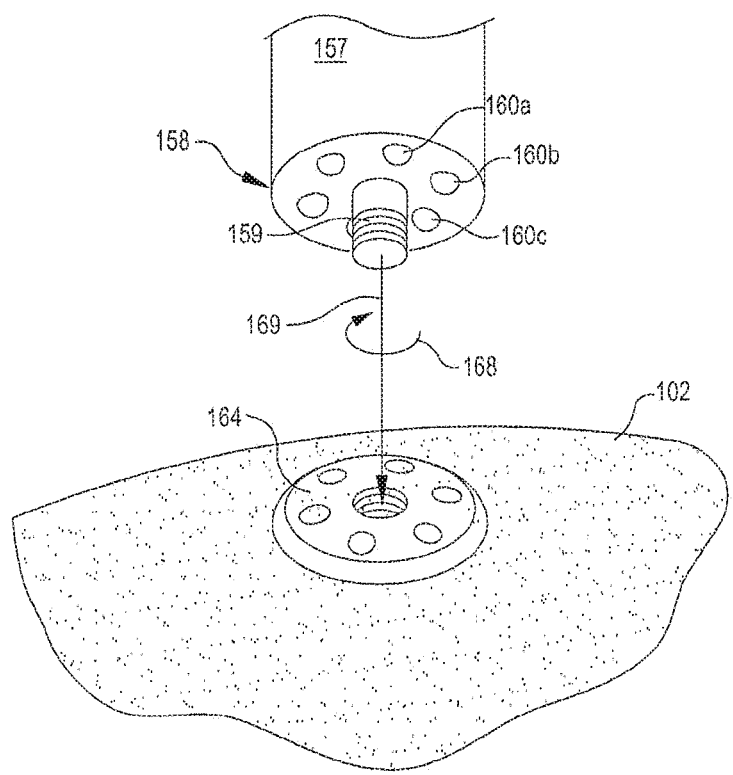

METHODS, SYSTEMS AND DEVICES FOR REPAIRING ANATOMICAL JOINT CONDITIONS

CROSS-REFERENCES TO RELATED APPLICATIONS

This application is a U.S. National Phase Application of PCT Application No. PCT/US2016/063481, filed Nov. 23, 2016, which claims the benefit of U.S. Provisional Application No. 62/260,030, filed on Nov. 25, 2015, which is incorporated herein by reference in its entirety for all purposes.

BACKGROUND OF THE INVENTION

The present invention relates generally to methods, systems, and devices for repairing anatomical joints. The repair may be necessitated by trauma, disease or other conditions (i.e. genetic deformity) and may specifically include mammalian joints such as the knee, shoulder, elbow, wrist, toe, hip, finger, spine and/or ankle, for example.

The knee is particularly susceptible to degeneration from disease, trauma, and long-term repetitive use that eventually leads to pain, swelling, and/or ankylosis. Knee pain alone is the impetus for various medical interventions and associated treatment costs.

Typically, the knee joint undergoes a wide range of motion and stress daily. In a healthy knee, the articulation between the bones of the knee is lined with cartilage. This cartilage serves to keep the knee stable, reduce joint friction, and absorb shock. Serious problems result when this cartilage deteriorates. In some cases, a patient may be in such severe pain that they cannot walk or bear weight.

Patients most often seek treatment because of pain and deterioration of quality of life attributed to osteoarthritis. Degenerative arthritis (i.e. osteoarthritis) is a very common joint disorder affecting an estimated 21 million Americans and may be part of a cluster of diseases known as metabolic syndrome. The disease is characterized by cartilage loss at the joint, and symptoms generally include pain and stiffness. Osteoarthritis can affect all joints of the body. The main goal of osteoarthritis treatment is to reduce or eliminate pain and restore normal joint function. Both non-surgical and surgical treatments are currently available for this purpose, with the appropriate treatment being selected based, in part, on the stage and/or severity of the disease.

Non-surgical treatments for knee osteoarthritis may include weight loss (for the overweight patient), activity modification (low impact exercise), quadriceps strengthening, patellar taping, analgesic and anti-inflammatory medications, and injections of corticosteroids and/or viscosupplements. Non-surgical joint treatments, usually involve pharmacological intervention such as the administration of non-steroidal anti-inflammatory drugs or injection of hyaluronic acid-based products. These treatments are initially administered to patients experiencing relatively less severe pain or joint complications. However, when non-surgical treatments prove ineffective, or for patients with severe pain or bone injury, surgical intervention is most likely required.

In addition to osteoarthritis, other conditions and diseases that impair the integrity and function of the knee and other human joints, include arthroses, chondromalacia patella, isolated chondral defect, juvenile idiopathic arthritis, ligamentous deficiency arthroses, osteonecrosis, osteochondritis dissecans, patellar instability, post-ligamentous injury arthritis, post-meniscectomy arthritis, post-meniscectomy arthroses, post-traumatic arthritis, septic arthritis and rheumatoid arthritis. Rheumatoid arthritis is an autoimmune disease where the body's defensive mechanisms attack the healthy joint tissue. Genetic defects can also predispose a person to experience joint problems.

Isolated articular cartilage defects and generalized cartilage disease, arthroses and arthritis, respectively, have certain surgical treatment options which attempt to mimic or recreate normal anatomy and joint mechanics and/or relieve symptoms of discomfort, instability and pain. Isolated disease often progresses to generalized disease, or arthritis. Generalized arthritis may also develop without known prior isolated disease. Arthritis may be present as a uni-, bi-, or tri-compartmental disease.

Uni-compartmental arthritis is typically less amenable to surgical options used for smaller isolated articular defects. With advanced cartilage degeneration and joint space narrowing, there is typically increased axial deformity and misalignment. Surgical options include osteotomy or uni-compartmental replacement. Options for bi- or tri-compartmental arthritis are combined procedures or total knee replacement.

Cartilage disease has been previously addressed by various means of replacing or substituting the damaged cartilage. Microfracture or abrasionplasty is a form of irritating exposed bone to create replacement fibrocartilage, but the resultant material is inferior to native cartilage.

Treating cartilage disease has also been attempted by realigning the joint with an osteotomy. This relieves an overloaded compartment, transferring stress to a less diseased compartment. The success of this approach involves avoiding non-union and other complications, requires prolonged non-weight bearing activity and requires eight to twelve months to realize clinical benefits. Only patients with mostly uni-compartmental disease are candidates for this treatment. Osteotomy also complicates latter joint replacement.

Osteochondral transplant replaces plugs of diseased cartilage and accompanying subchondral bone with grafts from either the patient or human cadaver. Small discrete lesions work well, but larger lesions, bipolar disease, and diffuse disease are not well addressed by this transplant procedure. Chondrocyte implantation harvests the patient's cartilage cells, grows them, and re-implants them on the bony bed, and covers them with a periosteal patch. Each of the aforementioned techniques work best for small contained lesions, unipolar defects and primarily femoral condyle lesions. Less optimal results occur with patellofemoral joint disease and tibial sided disease.

Surgical treatments, such as high tibial osteotomy (HTO), arthroplasty (TKA), or total knee replacement (TKR) are frequently recommended for patients with severe pain associated with osteoarthritis, especially when other non-invasive options have failed.

Arthroscopy is used to treat other causes of pain from arthritis, namely, loose bodies, loose or frayed cartilage, meniscus tears, and synovitis. These are temporizing measures (as this author can personally attest having undergone multiple arthroscopic surgeries).

The end stage of cartilage disease is to perform total joint reconstruction. This type of procedure presents a prolonged recovery time and surgical risks. Because total joint prostheses are fabricated of metal and plastic, revision surgery for worn-out components is fraught increased risk of complications compared to primary surgery.

All the aforementioned surgical procedures are relatively invasive, expensive and often only provide short term pain relief for the patient. Unfortunately, none of these procedures ameliorate all of the joint conditions and diseases discussed above.

Very little is known about the cause and progression of arthritis. Recently, with current diagnostic techniques such as MRI and bone scintigraphy, more information has been elucidated about the disease process and progression. In particular, it has been discovered that the subchondral bone plays a significant and important role in the initiation and progression of arthritis. The subchondral bone lies under the articular cartilage and provides support for the cartilage of the articular surface. Therefore, arthritis is not just a disease of the cartilage, but a disease affecting the underlying subchondral bone as well. Most of the clinical research to date is focused on cartilage regeneration/replacement and not on the status of underlying bone health.

Traditionally, cartilage has been viewed to be avascular, with diffusion of nutrients occurring from within the joint. Studies have confirmed, however, that subchondral bone is a key source of vascular and nutritional support for cartilage. With age, vascular and structural support from the subchondral bone diminishes, allowing arthritic disease to progress. The inability of the bone to adequately repair itself as increasing damage occurs starts a cycle of further destruction, interfering with cartilage vascular supply and structural support. Thus, the patient often experiences a downward spiral of pain.

As cartilage wear occurs, the primary functions of cartilage—to provide a low-friction bearing surface and to transmit stresses to the underlying bone—are diminished. Bone is most healthy when resisting compressive stresses. The shear stresses from the joint are partially converted to compression and tension via the architecture of the cartilage baseplate. Further, by virtue of the ultra-low friction surface of cartilage on cartilage (which is about 20× lower friction than ice on ice), shear stresses are mostly converted to longitudinal stress. The subchondral bone is the predominant shock absorber of joint stress. Via its arch-like latticework of trabecular bone, stresses are transmitted to the outer cortices and ultimately dissipated. Cartilage itself provides surprisingly little shock absorption secondary to its shear thickness and mechanical properties.

Bone is the ultimate shock absorber, with fracture being the unfortunate endpoint of force attenuation. Trabecular microfractures have been shown to occur in locations of bone stress in impulsively loaded joints. Every joint has a physiologic envelope of function. When this functional envelope is exceeded, the rate of damage exceeds the rate of repair. As cartilage disease progresses, subchondral bone is less able to dissipate the shear-type stresses it encounters. The attempts of subchondral bone to heal and remodel are seen as arthritis progresses including noticeable osteophyte formation, subchondral sclerosis, cyst formation, subchondral MRI-enhanced changes, and increased signal on bone scintigraphy. Joint deformity from these changes further increases joint reaction force. Cartilage homeostasis is compromised across structural, vascular, neural, and nutritional regions.

Clinical success of current cartilage surgery is limited as it generally only works for small, uni-polar (one-sided joint) lesions of the femoral condyle. No current treatment exists for bone edema or osteonecrosis of the knee.

Additional information related to attempts to address these problems can be found in U.S. patent numbers: U.S. RE43714; U.S. Pat. Nos. 2,188,631; 4,055,862; 4,344,193; 4,431,416; 4,502,161; 4,654,314; 4,687,675; 4,728,332; 4,787,848; 4,820,156; 4,880,429; 4,886,456; 4,919,667; 4,963,145; 5,007,934; 5,026,373; 5,171,322; 5,176,710; 5,306,311; 5,344,459; 5,514,141; 5,632,745; 5,865,849; 5,984,970; 6,037,519; 6,042,610; 6,046,379; 6,093,204; 6,149,651; 6,193,755; 6,206,927; 6,447,545; 6,530,956; 6,540,786; 6,562,071; 6,629,997; 6,645,251; 6,699,252; 6,758,865; 6,761,739; 6,767,369; 6,783,550; 6,793,676; 6,855,165; 6,911,044; 6,923,831; 6,994,730; 7,066,961; 7,282,063; 7,291,169; 7,297,161; 7,338,524; 7,585,311; 7,608,105; 80,775,563; 8,317,792; 8,480,757; 8,623,089; 8,608,802; 8,753,401; 8,753,401; 8,968,404; 9,155,625; and U.S. patent application Publication Numbers: US 20020173855; US 20030040798; US 20030109928; US 2003083665; US 20040006393; US 20040133275; US 20040199250; US 20040243250; US 20050004572; US 20050033424; US 20050043813; US 20050055101; US 20050060037; US 20050171604; US 20050209703; US 20050221703; US 20050234549; US 20050267584; US 20050278025; US 20060155287; US 20060173542; US 20060190078; US 20070005143; US 20070078518; US 20070179610; US 20080077248; US 20080119947; US 20080215055; US 20080262616; US 20090024229; US 20100145451; US 20110029081; US 20110034930; US 20110125264; US 20120053588; US 20120172880; US 20130035764; US 20140303629; US 20140287017; US 20140250676; US 20140276845; US 20140148910; US 20140121708; US 20140114369; US 20140107795; US 20140109384; US 20140277544; US 20130035561; US 20140276845; US 20140039454; US 20130035764; US 20140121708; US 20120316513; US 20140074103; US 20130325126; US 20140074117; US 20110125264; US 20140107781; US 20110125157; US 20120316571; US 20160250026; as well as European Patent Application Numbers: EP 0739631B1; EP 1541095; EP 1719532A3; EP 2174674B1; EP 2308027B1; EP 2621411A2; EP 2717808A2 and International Patent Application Numbers: CA 2838816A1; WO 199624302A1; WO 200139694A1; WO 2007007106A1; WO 2010065426A1; WO 2011063240A1; WO 2011063250A1; WO 2012170805A2; WO 2013137889A1; WO 2014145406A1; WO 2014145267A1; WO 2014152533A1; WO 2014159913A1; WO 2014039998A1; WO 2014053913A2; WO 2014045124A2; and WO 2014074806A1, for example.

Various methods, systems, and devices for repairing anatomical joint conditions, including some embodiments of the invention, can mitigate or reduce the effect of, or even take advantage of, some or all of these potential problems.

Therefore, there is a legitimate need for cost-effective, minimally invasive methods, systems and devices for repairing anatomical joints, including the human knee joint. The need is particularly acute in society today given an aging population that cherishes an active lifestyle. It would be particularly desirable to have a minimally invasive methods, systems and devices for repairing anatomical joints conditions that specifically address the subchondral bone in arthritic disease process and progression to relieve the pain that results from diseased subchondral bone and the spectrum of symptoms that result from arthritis, including pain, stiffness and swelling. It would be further desirable to have methods, systems and devices for repairing anatomical joints that provide: (1) a treatment specifically for bone edema, bone bruises, and osteonecrosis that has previously not existed; (2) structural scaffolding to assist in the reparative processes of diseased bone next to joints; (3) shock absorbing enhancement to subchondral bone, (4) compressive, tensile, and especially shear stress attenuation enhancement to subchondral bone; (5) a means to prevent further joint deformity from subchondral bone remodeling such as osteophyte formation; (6) assistance in the healing or prevention of further destruction of overlying cartilage by maintaining and allowing vascularity and nutritional support from subchondral bone; (7) assistance in the healing or prevention of further destruction of overlying cartilage by providing an adequate structural base; (8) a minimally invasive alternative to total joint reconstruction that also does not preclude or further complicate joint reconstruction: (9) a treatment for subchondral bone disease and arthritis that delays or stops disease progression; (10) an implant for arthritis that is less likely to loosen or wear, as it is integral to the trabecular framework it supports; (11) an alternative for tibial sided, patellofemoral, and bipolar disease (tibial-femoral) that is relatively easy to perform, as an adjunct to arthroscopy, and as an outpatient procedure with minimal downtime for the patient; (12) a treatment for arthritis that allows a higher level of activity than that allowed after joint resurfacing or replacement; (13) a cost effective alternative to joint replacement with reduced need for revision and surgical morbidity, especially in countries with limited medical resources; and (14) a treatment option in veterinary medicine, specifically in equine arthroses and arthritides, among other desirable features, as described herein.

BRIEF SUMMARY OF THE INVENTION

According to one embodiment of the present invention, an implantable orthopedic device for repairing anatomical joints and ameliorating joint conditions at a treatment site of a human or animal (i.e. equine, ovine or bovine) comprises a first section with a joint-ward end, an opposing mating end, and a lateral wall extending between the joint-ward end and the mating end. The first section further comprises a peripheral column partially forming the lateral wall of the first section and a central column at least partially within the peripheral column. The joint-ward end comprises a plurality of fenestrations. Each fenestration is formed by a confluence of the peripheral column and the central column. The first section further comprises a central aperture within and formed by the central column and configured to mate with an introducer. A second section comprises a mating end, an opposing leading end, and a lateral wall extending between the mating end and the leading end. The lateral wall has an inner wall and an outer wall. The lateral wall of the second section comprises protrusions on the inner wall, outer wall, or a combination of both the inner and outer walls. The leading end comprises an edge that first penetrates a bone during implantation. The lateral wall of the second section further comprises a plurality of fenestrations between the protrusions. The device has a width and a length and the width and length of the device comprise an aspect ratio of between about 0.3 and 3.0, respectively. More specifically, the width and the length of the device may comprise an aspect ratio of between about 0.3 and 2.0, respectively. The implantable orthopedic device is implanted in the bone at the treatment site and the bone is a subchondral bone.

In some embodiments, the implantable orthopedic device may include a biomaterial. The biomaterial is a biocompatible material, a biocomposite material, a biomimetic material, a bioactive material, a nanomaterial, a partially absorbable material, a fully absorbable material, a tissue forming material, a biphasic material, a replaceable material, a graft material (e.g. an allograft, autograft, or xenograft) or any combination of these materials. The biphasic material may include a solid component and non-solid component. In some embodiments, the non-solid component is a gel. The gel has an elastomeric quality and a viscosity in order to sufficiently inhibit the it from dripping off the device when the device is implanted at the treatment site. The viscosity is greater than about 1.0 mPa-s (i.e. millipascal seconds). Preferably, the viscosity is between about 1.5 mPa-s and 5.0 mPa-s. The gel is generally similar to the consistency of a Haribo Gummibärchen (i.e. gummy bear fruit candy), for example. The non-solid component of the biphasic material exhibits viscoelastic properties. The biomaterial includes an antimicrobial agent and/or a chemotherapeutic agent.

In some embodiments, the anatomical joint may include a mammalian hip, knee, ankle, shoulder, elbow, wrist, finger, toe, or spine per some embodiments of the subject invention. The anatomical joint is selected from the group consisting of an acetabulofemoral joint, an acromioclavicular joint, a femoropatellarjoint, a femorotibial joint, a glenohumeral joint, a humeroradial joint, a humeroulnar joint, an interphalangeal joint, a metacarpal joint, a radioulnar joint and a talocrural joint. In some cases, the anatomical joint is a human knee joint. The condition is chosen from the group consisting of chondromalacia patella, isolated chondral defect, juvenile idiopathic arthritis, ligamentous deficiency arthroses, osteonecrosis, osteoarthritis, osteochondritis dissecans, patellar instability, post-ligamentous injury arthritis, post-meniscectomy arthritis, post-meniscectomy arthroses, post-traumatic arthritis, septic arthritis, rheumatoid arthritis, osteochondral defect, subchondral bone insufficiency, fracture, overload or genetic defects. The term "overload" in this use implies a pre-fracture state. The plurality of fenestrations (i.e. perforations, openings or pores) are variable sizes (and shapes) that provide support for different tissue types and also promote healing repair at the treatment site. For example, the plurality of fenestrations between the protrusions on the second section of the lateral wall are between about 300 microns and 1200 microns in size to promote bone growth while the plurality of fenestrations on the joint-ward end of the first section are between about 100 microns to 800 microns in size to promote cartilage growth. Preferably, the plurality of fenestrations on the joint-ward end of the first section are between about 400 microns to 800 microns in size to promote cartilage growth. Circular pores, pie-shaped fenestrations and other shapes are considered. The plurality of fenestrations are pores sized about 400 microns in diameter to promote bone growth and pores sized about 200 microns in diameter to promote cartilage growth.

In other embodiments, an external surface of the device is at least partially textured to increase the surface area of the device. The texture may include a dimpled pattern or even relatively more complex "patterns within a pattern" configurations. The external surface is at least partially coated with a material and the material coating may be a biomaterial that promotes tissue growth, tissue differentiation and/or tissue attraction, for example. The material coating is selectively applied to create a region of relatively thick coating and a region of relatively thin coating on the external surface of the device. The material coating may be sprayed on the external surface of the device, bonded to the external surface of the device or deposited on the external surface of the device. The many ways to coat surfaces are well known to those of skill in the art and may include chemical or electrochemical bonding, spray coating, vapor deposition, roll-to-roll coating and many other methods, for example.

In some embodiments of the invention, the lateral wall of the second section includes one or more vascular grooves extending from the mating end to the leading end. The one or more vascular grooves provide a surface area for blood adhesion and may extend in an substantially parallel configuration to encourage blood flow capillarity and discourage blood flow turbulence. Alternatively or additionally, the one or more vascular grooves may extend in an substantially spring-shaped (i.e. coiled) configuration to encourage blood flow capillarity and discourage blood flow turbulence. In some embodiments, the device is configured for customized production, the customized device corresponds to a specific joint anatomy to accommodate bipolar defects or gender-specific differences, for example. The device may even be produced in a customized fashion using additive manufacturing (AM), direct metal laser sintering (DMLS), selective laser sintering (SLS), selective laser melting (SLM), metal injection molding (MIM), laser engineered net shaping (LENS), 3D printing, or computer-aided design/computer-aided manufacturing (CAD/CAM) techniques, for examples. Of course, other production methods are contemplated and are not limited to the examples previously provided. The customized device may be a monobloc device or a modular device and may be configured to accept and retain an amount of the biomaterial when the biomaterial is administered post-implantation. The amount of biomaterial administered post-implantation may be made with a needle injection, a fluoroscope guide, or an ultrasound guide. A carrier substance may be attached to the device. The carrier substance is a polymer, or biomaterial, or medicine, or a hybrid combination thereof. The carrier substance may be a polymer configured in a sponge matrix arrangement. The carrier substance may be a biomaterial that includes cartilage, osteocartilage, platelet-rich plasma (PRP), a chemotactic substance or a cellular differentiation substance. The cartilage or other tissue may be an autograft, allograft or xenograft. The carrier substance may also include an artificial graft with a synthetic material, for example. The cellular differentiation substance may include stem cells, specifically including but not limited to, injectable mesenchymal stem cells (MSCs) that are configured to migrate to the device when the device is implanted at the treatment site. Further, the biomaterial may be contained by a cover.

In some embodiments, the lateral wall of the second section has a taper from the mating end to the leading end and the taper is a variable configuration or an adjustable configuration. The outer wall of the lateral wall of the second section has a taper of between about 1.0 degree and 9.0 degrees from the mating end to the leading end and the inner wall of the lateral wall of the second section has a taper of between about 1.0 degree and 9.0 degrees from the mating end to the leading end. The protrusions on the inner wall and the protrusions on the outer wall are both configured to engage bone when the device is implanted at a treatment site. The protrusions may be threads including a variable thread pitch design or a consistent thread pitch design. The threads may be chosen from the group consisting of reverse cutting threads, notched threads, tapered threads, buttress threads, metric threads, trapezoidal threads, acme threads, pipe straight threads, unified threads, custom threads and multi-threads, for example. The tapered threads are configured to constantly purchase new bone to minimize strip out and increase holding power at the treatment site.

In another embodiment, the device further comprises at least three struts with each strut extending between and connecting the peripheral column and the central column. Each strut supports the central column. The struts may be between the pie-shaped fenestrations, for example. The three or more struts may include one or more flares extending below the at least three struts. The flare(s) are configured to resist subsidence within the bone at the treatment site. It is understood that the at least one flare may be a tapered flare, a helical flare, a notched flare or a barbed flare configuration. The helical flare may include an angle of more than 45 degrees and the flare is configured to self-lock. The mating end of the second section includes a non-threaded press-fit portion configured to substantially seal out synovial fluid. The device may also include a geometric washer attached to the joint-ward end of the first section. The washer geometry comprises a convex, concave or flat profile as seen on a cross-sectional, lateral perspective view. Additionally, the washer geometry is configured in a bowl-shape to contain a biomaterial and promote tissue ingrowth at the treatment site. The biomaterial may comprises a porous material impregnated with a matrix-promoting substance and the substance may support a population of progenitor cells.

The washer geometry may include chambers to house a biomaterial and engage a tissue at the treatment site. The chambers may have an overhanging lip portion configured to retain the biomaterial. Furthermore, the washer geometry may be independently customized and configured to match a topography of the bone at the treatment site. This has several advantages including facilitating smooth joint movement post-implantation. The attachable washer includes a threaded attachment, a spiked attachment, a slide-lock attachment, a snap-fit attachment or a notched attachment, for example. The washer may be partially or completely absorbable over a period of time after the washer is attached to the device at the treatment site. The washer may also be configured to promote guided tissue regeneration (GTR).

In another embodiment of the subject invention, a method of repairing anatomical joints and ameliorating joint conditions comprises providing at least one non-telescoping, single walled primary bearing strut element of variable geometry and thickness having a longitudinal body with open opposing ends and a vertically disposed inner edge and a vertically disposed outer edge suitable for insertion within a subchondral bone. The vertically disposed outer edge is aligned to fit the subchondral bone at the treatment site. A plurality of vertically-formed hollow grooves are disposed on the outer edge and engaged with a longitudinal insertion holder. The longitudinal insertion holder is used to penetrate the subchondral bone during insertion of the at least one non-telescoping, single walled primary bearing strut element within the subchondral bone at the treatment site. The at least one non-telescoping, single walled primary bearing strut element is maintained in place within the subchondral bone by aligning the vertically disposed inner edge to first penetrate the subchondral bone during insertion. A porosity of the longitudinal body is positioned at the treatment site to promote healing by vascularity, bridging bone, and other biological elements that pass through the porous body.

In yet another embodiment, a method of preparing a defect at a treatment site on a subchondral bone to repair an anatomical joint and ameliorate a joint condition comprises surgically accessing the treatment site. A sizing instrument with a proximal end, a distal end, and a cylindrical member disposed between the proximal end and the distal end is accessed. The cylindrical member has a lumen for receiving a guidewire. The distal end of the sizing instrument is centered in a position over the defect at the treatment site on the subchondral bone. The distal end has concentric rings and each ring has a known diameter. A diameter of the defect is measured by comparing the defect diameter with the closest corresponding known diameter on the sizing instrument. The guidewire is inserted through the lumen of the cylindrical member while the distal end of the sizing instrument is centrally positioned over the defect. The subchondral bone is contacted with a distal end of the guidewire. The center of the defect is marked by reversibly attaching the guidewire to the subchondral bone. The sizing instrument is then removed over the guidewire. A countersink instrument having a diameter substantially matching the measured diameter of the defect is selected. The countersink is positioned over the guidewire. The countersink is simultaneously rotated and lowered to engage a soft tissue and the subchondral bone. The subchondral bone is penetrated with the countersink to form a hole. The hole has a first depth. The countersink is removed over the guidewire. A cannulated drill is positioned over the guidewire. An inner circular portion of the subchondral bone is now removed while preserving a central post of subchondral bone in an substantially undisturbed native state by simultaneously rotating and lowering the cannulated drill into a center of the countersink hole. The inner circular portion has a second depth. The cannulated drill is removed over the guidewire. The guidewire is detached from the subchondral bone and the guidewire is removed from the treatment site. An implantable orthopedic device is placed in the hole over a top of the central post. The central post is accepted by a hollow central column of the device when implanted. The orthopedic device is secured into the hole using a driver instrument and the driver instrument is removed leaving the orthopedic device secured in place. This method may further comprise the step of providing an inflatable envelope, inserting the inflatable envelope into the anatomical joint in a collapsed position and at least partially expanding the envelope to an inflated position to cause surrounding tissue to be displaced by an inflation pressure. In this manner, the treatment site may be more easily accessed and viewed by the surgeon because tissues in the vicinity of the treatment site are retracted (i.e. displaced) as the envelope inflates. The hollow central column of the implantable orthopedic device may include a chamfer. The chamfer narrows a diameter of the hollow central column to compact the central post of the subchondral bone when the implantable orthopedic device is placed in the hole over the top of the central post. The chamfer includes an angle of about 45 degrees. The loading of the central post is increased and/or resorption of the central post is decreased when the central post of the subchondral bone is compacted. The chamfer inhibits formation of bone cysts and/or bone spurs. The implantable orthopedic device includes a blind-ended central aperture which extends only partially through a joint-ward end of the device such that synovia (i.e. synovial fluid) leakage is mitigated or even prevented.

The first depth, as previously described, allows the implantable orthopedic device to be implanted substantially flush with (or slightly below) a surface of the subchondral bone. The second depth promotes blood flow around the top and sides of the central post to facilitate repair of the anatomical joint at the treatment site. The central post of subchondral bone is preserved in an substantially undisturbed state to provide structural integrity to the treatment site and facilitate repair of the anatomical joint. The inner portion has a diameter less than or equal to the diameter of the countersink hole and the inner portion has a diameter larger than a diameter of a wall of the implantable orthopedic device. The inner portion has a second depth sufficient to allow placement of the implantable orthopedic device.

Furthermore, the countersink instrument comprises two or more blades and the blades are equally spaced apart from one another. The blades are arranged circumferentially about a central axis. In some embodiments, the countersink instrument comprises four blades with each blade oriented at 180 degrees relative to the adjacent blade. The cannulated drill comprises two or more prongs and each prong is equally spaced apart from one another. In other embodiments, the cannulated drill comprises three prongs and the prongs are configured to debride and clear bone away during use to preserve a porosity of the bone, minimize tissue trauma, encourage bleeding, and promote healing at the treatment site. Each blade is configured with a radius of curvature that substantially mirrors a radius of curvature of the subchondral bone at the treatment site. The radius of curvature of the subchondral bone at the treatment site may be convex, concave or even flat (i.e. 180 degrees).

Some minor bleeding during this procedure is beneficial to promote healing. The bleeding includes laminar blood flow, turbulent blood flow, capillary blood flow and percolatory blood flow. The orthopedic device is secured in the hole using the driver instrument and further comprises engaging a distal end of the driver instrument with a joint-ward end of a first section of the orthopedic device and screwing the orthopedic device into the hole. This method my also further include creating one or more vascular channels in the subchondral bone at the treatment site to facilitate additional minor bleeding. These vascular channels are created after the step of removing the countersink over the guidewire. The vascular channels are created by drilling, reaming, tapping, boring, or poking, for example. Of course other ways to create vascular channels and micro channels are contemplated.

The second depth is greater than the length of the implantable orthopedic device. The distal end of the driver instrument reversibly engages a joint-ward end of the device to move the orthopedic device into the hole. The step of moving the orthopedic device into the hole may further comprise locking the device in the hole at a depth where the joint-ward end of the device is substantially flush with a surface of the subchondral bone. The orthopedic device is locked via a morse locking tapered connection. The treatment site may be accessed from a variety of directions using different surgical techniques. For example, an antegrade insertion technique may be used to access the site through the joint surface from below. The treatment site may also be accessed from either side using a peripheral insertion technique. Alternatively, the treatment site may be surgically accessed using a retrograde insertion technique whereby the treatment site or joint compartment is accessed in a direction opposite antegrade. Retrograde, antegrade and peripheral insertion techniques are well known to those of ordinary skill in the art including orthopedic surgeons, for example. The implantable orthopedic device may be covered with a protective sleeve before the device is introduced into a patient and the sleeve may be removed before the device is positioned in the hole over a top of the central post.

In another embodiment of the invention, a cannula is disclosed to arthroscopically retract a target tissue at an anatomical joint. The cannula comprises a delivery tube having a distal end, a proximal end, and an elongate member disposed between the distal and proximal ends. A guided slot runs at least partially along a length of the elongate member. A rod-like retractor is configured for movable insertion in the delivery tube. The retractor has a distal end, a proximal end, and an elongate section disposed between the distal and proximal ends. The distal end of the retractor is bent at an angle relative to the elongate section of the retractor. In use, the distal end of the retractor is configured to movably track along the slot and engage the target tissue. The engaged tissue is retracted in an substantially proximal direction relative to an axis of the delivery tube when a force is applied to the proximal end of the retractor. The retractor can be locked at a position along the slot. The cannula may have an angle of about 90 degrees. The delivery tube of the cannula may be composed of a transparent material such as clear plastic, for example. The cannula may be configured to extend telescopically and may not be straight. The cannula is capable of retaining a reversibly customized configuration. The customized configuration is accomplished by the application of one or more directional forces along the delivery tube (e.g. such as bending a shape memory material). The retractor may include an inflatable balloon which inflates around at least part of a cross-sectional circumference of the cannula. The cannula further includes one or more modular leaflets. The cannula is bendable so as to facilitate navigation along a tortuous anatomical path.

In yet another embodiment, a method for retracting a tissue of an anatomical joint is disclosed. The joint has a targeted space, the method comprises surgically accessing the anatomical joint. An inflatable envelope is arthroscopically inserted in the targeted space in a first collapsed position and the inflatable envelope is at least partially expanded into a second inflated position to cause the surrounding tissue to be displaced by an inflation pressure. The envelope is inflated with a gas or liquid. If a liquid is used to inflate the envelope, a saline solution may be used. Of course, many other substances can also be used to safely and efficiently inflate the envelope.

In other embodiments, the anatomical joint is a human knee joint and the targeted space is a suprapatellar pouch or a retropatellar pouch. The displaced tissue may be cartilage, ligament, tendon, and/or adipose tissue, for example. The inflatable envelope is foldable in the collapsed position and may also be deflated and subsequently removed from the targeted space.

In another embodiment, a method for delivering at least one therapeutic biomaterial to a primary treatment site to repair an anatomical joint comprises accessing an implantable orthopedic device. The device includes multiple portions with each portion having a different surface area. A first biomaterial is applied to at least a first portion of the orthopedic device and the device is implanted at the primary treatment site where the biomaterial promotes repair of the anatomical joint. A portion of the biomaterial may migrate away from the primary treatment site into the surrounding joint compartment to provide therapy to a secondary site beyond, and in addition to, the primary treatment site. The secondary site may be a medullary canal, for example. A second biomaterial is applied to at least a second portion of the device. The second biomaterial and the at least second portion are different from the first biomaterial and the at least first portion of the device. At least one therapeutic biomaterial may be a biocompatible material, a biocomposite material, a biomimetic material, a bioactive material, a nanomaterial, a partially absorbable material, a fully absorbable material, a tissue forming material, a biphasic material, a replaceable material, a graft material (e.g. an allograft, autograft, or xenograft) or any combination of the aforementioned materials. At least one therapeutic biomaterial is applied to the at least first portion of the device after the orthopedic device is implanted at the treatment site. At least one therapeutic biomaterial is applied to the at least first portion of the device both before and after the orthopedic device is implanted at the treatment site. Also, at least one therapeutic biomaterial promotes tissue growth, encourages bleeding and inhibits infection so as to facilitate repair of the anatomical joint. The at least one biomaterial also possess chemotactic, cellular homing, biological crosstalk and/or time-release capabilities. In some embodiments, the at least first and/or the at least second portions of the device include pores, scaffolds, lattices, matrices, or any combination thereof and the different surface areas of each portion correspond to a property of the at least one biomaterial.

In another embodiment of the invention, a kit for repairing an anatomical joint is disclosed. The kit comprises the implantable orthopedic device, a sizing instrument, a guidewire, a countersink instrument, a cannulated drill, a drill bit guide, a drill bit, a sleeve, a driver instrument, an injector, an inflatable envelope, at least one biomaterial, instructions for use, and a package. The package holds the implantable orthopedic device as previously described, the sizing instrument, the guidewire, the countersink instrument, the cannulated drill, the drill bit guide, the drill, the sleeve, the driver instrument, the injector, the inflatable envelope, at least one biomaterial, and the instructions for using the kit. In some embodiments, the kit is sterilizable.

In another embodiment of the invention, a method of securing a carrier substance to a bone defect comprises positioning a first implantable orthopedic device substantially near the bone defect. The device comprises a joint-ward end, an opposing mating end, and a lateral wall extending between the joint-ward end and the mating end. The lateral wall includes fenestrations. A length of strand material is provided and the strand has first and second ends. The first end is threaded through a first fenestration. The first end exits through a second fenestration. The first end is then secured to the device. A first carrier substance is placed substantially near, or in contact with, the joint-ward end of the device. The carrier substance has therapeutic properties. The second end of strand material is looped across the carrier substance. The second end is threaded through a third fenestration which is opposite, or adjacent to, the first fenestration. The second end exits through a fourth fenestration. The second end of the length of strand material is pulled taut across the carrier substance and the second end to the device is secured to tether the carrier substance near the joint-ward end of the device. The first end and the second end may be secured to the device by tying a knot at each end, for example. The strand material may comprise absorbable sutures or non-absorbable sutures and the carrier substance and/or one or more strands may be secured either pre- or post-implantation of the device. Additional lengths of strand material are used to form patterns to tether the carrier substance near the joint-ward end of the device.

In yet another embodiment of the invention, a method of attaching a carrier substance to a bone defect comprises positioning a first implantable orthopedic device substantially near the bone defect at a first location. A second implantable orthopedic device is positioned substantially near the bone defect at a second location. It should be noted that the first and second locations are different locations. Each of the first and second devices comprises a joint-ward end, an opposing mating end, and a lateral wall extending between the joint-ward end and the mating end. A carrier substance is placed substantially near, or in direct contact with, the joint-ward end of the first and second devices. The carrier substance spans a contiguous area between the first and second devices across the bone defect. A length of strand material is provided and the material has a first end and a second end. The first end is threaded through a first fenestration in the first device. The first end exits through a second fenestration in the first device. The first end is secured to the first device. The second end of a strand material is looped across the carrier substance. The second end is threaded through a first fenestration in the second device. The second end exits through a second fenestration in the second device. The second end of the length of suture material is pulled taut across the carrier substance. The second end is secured to the second device so as to tether the carrier substance between the devices. The lateral wall may include threads for anchoring the device in a bone and, if the lateral wall contains threads, the threads include notches spaced along a thread path. The fenestrations are vertically aligned under each of the notches. The carrier substance comprises a polymer, or biomaterial, or medicine, or a combination thereof. The fenestrations may be vertically aligned with each other along the lateral wall.

In another embodiment, a driver instrument for reversibly engaging an implantable orthopedic device is disclosed. The device is configured to implant in a bone. The driver instrument comprises a distal end having a male configuration including a centrally-located threaded protuberance and relatively shorter elongate knobs. The knobs form a diameter around the protuberance such that when the driver instrument is aligned in proximity with the implantable device and rotated, the threaded protuberance engages a mirror reverse female configuration located on a joint-ward end of the implantable device. Continued rotation causes the knobs to engage the corresponding configuration on the implantable device to provide sufficient leverage to implant the implantable orthopedic device in the bone.

In yet another embodiment, an extraction tool is disclosed for removing an implantable orthopedic device implanted in a bone. The extraction tool comprises a distal end, a proximal end and an elongate member disposed between the distal end and the proximal end. The elongate member includes a conduit running at least along a length of the distal end. The conduit includes two or more nubs projecting from an inside surface of the conduit. The nubs are configured to engage and slide past corresponding notches spaced vertically along thread paths of the implantable orthopedic device when the extraction tool is placed over an exposed surface of the implantable orthopedic device. The extraction tool is rotated after the two or more nubs engage and slide past at least one of the corresponding notches to seat the notches between thread paths. This allows efficient leverage using a twisting and/or pulling motion to remove the device from the bone. The nubs on the inside surface of the conduit are about 0.9 mm in length.

BRIEF DESCRIPTION OF THE DRAWINGS

These and other features, aspects and advantages of the present invention will become better understood with regard to the following description, appended claims, and accompanying figures where:

FIGS. 1Aa, 1Ab, 1B and 1C are side views of embodiments of a device for repairing anatomical joint conditions according to the present invention;

FIG. 1D is a side perspective view of embodiments of a device for repairing anatomical joint conditions according to the present invention;

FIG. 9D is a cross-sectional, side view of another embodiment of the device for repairing anatomical joint conditions according to the present invention;

FIG. 10 is a cross-sectional, side view of another embodiment of the device for repairing anatomical joint conditions according to the present invention;

FIG. 11A is a side view of an embodiment of a device for repairing anatomical joint conditions according to the present invention;

FIGS. 11B-11D are lateral perspective views of alternative embodiments according to the present invention;

FIG. 11E is a lateral perspective view of an embodiment of a device for repairing anatomical joint conditions according to the present invention;

FIGS. 11Hd-11Hi are top views of FIG. 4D with alternative embodiments according to the present invention;

FIGS. 11Hj-11Hl are top views of FIG. 4D with alternative embodiments according to the present invention;

FIG. 11Hm is a lateral perspective view of an alternative embodiment according to the present invention;

FIGS. 12A-12B are lateral views of an embodiment according to the present invention;

FIGS. 13A-13B are top perspective views of embodiments according to the present invention;

FIGS. 13C-13D are lateral perspective views of yet additional embodiments of a device for repairing anatomical joint conditions according to the present invention;

FIGS. 17Fb-17H are lateral perspective views of other embodiments of the present invention;

FIGS. 23A-23C are perspective sequential views of a driver instrument and implantable orthopedic device according to embodiments of the present invention.

DETAILED DESCRIPTION OF THE INVENTION

According to one embodiment of the present invention there is provided a device for repairing anatomical joint conditions and ameliorating joint conditions. According to another embodiment of the present invention, there is provided a method for repairing anatomical joints and ameliorating a joint condition so, preparing a defect at a treatment site on a bone to repair an anatomical joint, a cannula for retracting a target tissue, a method for delivering at least one biomaterial to a primary treatment site, and a kit for repairing an anatomical joint. In one embodiment, the method comprises providing a device according to the present invention. These embodiments will now be described in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed and shown are not intended to be limiting nor are they intended to indicate that each step is essential to the method or that each step must occur in the order disclosed but instead are exemplary steps only.

All dimensions specified in this disclosure are by way of example only and are not intended to be limiting, except where the context requires otherwise. Further, the proportions shown in these Figures are not necessarily to scale. As will be understood by those with skill in the art with reference to this disclosure, the actual dimensions and proportions of any device or part of a device disclosed in this disclosure will be determined by its intended use.

This provisional application is related to U.S. patent application Ser. No. 13/421,792 (our reference number 96342-893565-000120US), now U.S. Pat. No. 8,968,404, entitled Method and Device for Ameliorating Joint Conditions and Diseases, filed Mar. 15, 2012, the contents of which are incorporated in this disclosure by reference in their entirety. The provisional application is also related to U.S. patent application Ser. No. 13/420,825 (our reference number 96342-894576-000110US) now issued as U.S. Pat. No. 8,753,401, entitled Joint Support and Subchondral Support System, filed Mar. 15, 2013, the contents of which are incorporated in this disclosure in their entirety.

Figure 9A:
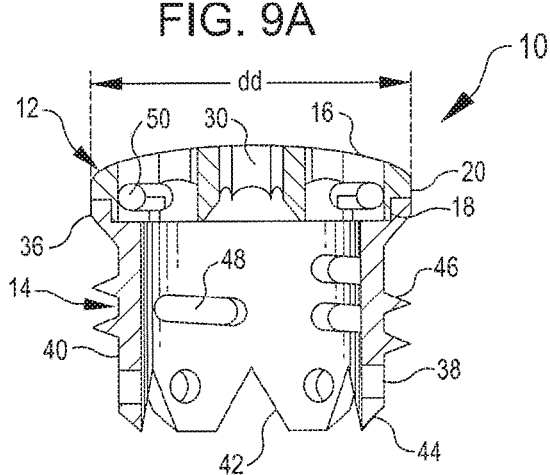
FIG. 9A is a cross-sectional, side view of the embodiment of the device for repairing anatomical joint conditions shown in FIG. 1A taken along line 9-9.
Figure 9B:
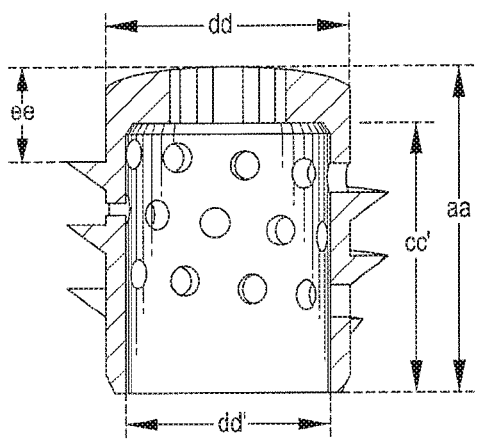
FIG. 9B is a cross-sectional, side view of the embodiment of the device for repairing anatomical joint conditions shown in FIG. 1B taken along line 9-9.
Figure 9C:
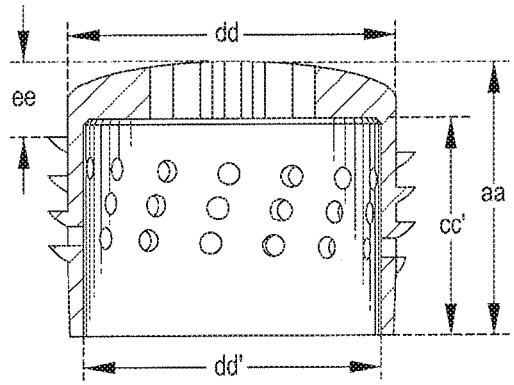
FIG. 9C is a cross-sectional, side view of the embodiment of the device for repairing anatomical joint conditions shown in FIG. 1C taken along line 9-9.

According to one embodiment of the present invention, there is provided methods, systems and devices for repairing anatomical joint conditions. As per FIGS. 1Aa, 2A, and 3, the device 10 comprises a first section 12 and a second section 14, and comprises a generally cylindrical shape partially or completely closed at one end. The first section 12 and second section 14 may be separately attachable (i.e., threaded or press-fit) or fused together. The device 10 further comprises an axial length (aa). The axial length (aa) is between about 5 mm and 30 mm (FIG. 1Aa). The device may be a single section as shown in FIG. 1B, 1C or 1D. The axial length (aa) may be between 8 mm and 16 mm. Preferably, the axial length (aa) is 8 mm (FIG. 9B) or 14 mm (FIG. 9C).

Figure 4A:
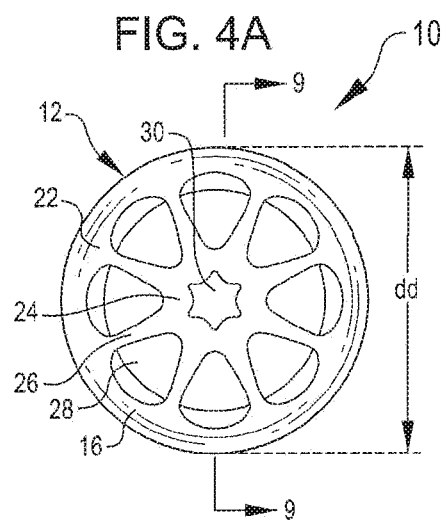
FIGS. 4A, 4B, 4C and 4D are top perspective views of embodiments of the device for repairing anatomical joint conditions shown in FIGS. 1Aa, 1B, 1C and 1D, respectively.
Figure 4B:
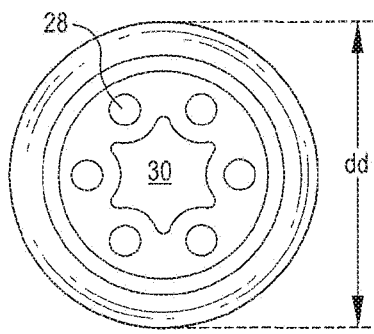
Figure 4C:
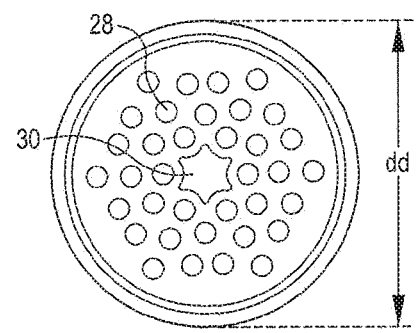

The first section 12 of the device 10 comprises a joint-ward end 16, an opposing mating end 18, and a lateral wall 20 extending between the joint-ward end 16 and the mating end 18. The first section 12 further comprises a diameter (dd) and an axial length (bb). The diameter (dd) is between 5 mm and 30 mm (FIG. 4A). In another embodiment, the diameter (dd) is between 6 mm (FIG. 4B) and 16 mm (FIG. 4C). In one embodiment, the device may be tapered so the diameter (dd) is different than diameter (dd'). FIGS. 9B and 9C show a taper of 6 mm and 16 mm (dd) to 5 mm and 14 mm (dd'), respectively, for example. In one embodiment, the axial length (bb) is between 0.5 mm and 2.5 mm (FIG. 1Aa). Preferably, the axial length (bb) is between about 1 mm and 2.5 mm. The axial length (bb) to the start of the first thread 46 is shown as distance (ee). The distance (ee) is about 2.45 mm (FIG. 9B) and about 4 mm (FIG. 9C), for example.

In one embodiment, the first section 12 further comprises a peripheral column 22 partially forming the lateral wall 20, a central column 24, and three or more than three struts 26, each strut 26 extending between and connecting the peripheral column 22 and the central column 24, and each strut 26 thereby supporting the central column 24.

Figure 7:
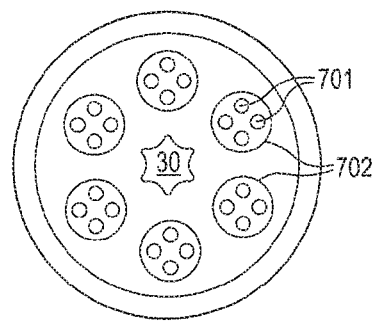
FIGS. 7 and 8 are top perspective views of embodiments of the device for repairing anatomical joint conditions.
Figure 8:
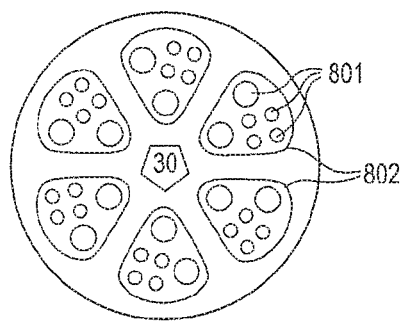

In one embodiment, the joint-ward end 16 further comprises a plurality of fenestrations 28, where each fenestration 28 is formed by a confluence of the peripheral column 22, the central column 24, and two adjacent struts 26 of the three or more than three struts 26. Each fenestration 28 can comprise any shape suitable for the intended purpose of the device 10, as will be understood by those with skill in the art with respect to this disclosure. In one embodiment, as shown particularly in FIGS. 2A and 4A, each fenestration 28 comprises a pear or teardrop shape. In another embodiment, as shown in FIGS. 2B, 2C, 2D, 4B, 4C and 4D, each fenestration 28 comprises circular pores. As will be understood by those with skill in the art with respect to this disclosure, all fenestrations 28 on the device 10 can comprise the same size and shape or one or more than one fenestration 28 can comprise a different size, different shape or both a different size and a different shape than one or more than one other fenestration 28. The fenestrations can also be arranged in a "pattern 701, 801 within a pattern 702, 802" configuration as shown in FIGS. 7 and 8, respectively. This arrangement may also include fractal and/or undulating surface geometries. Of course, a plethora of other patterns are possible.

The fenestrations may have different porosities targeted to promote specific tissue growth and differentiation. For example, fenestrations of about 300-1200 microns in diameter may promote existing bone growth and/or regrow bone (particularly along the sides of the device) while fenestrations of about 400-800 microns may be best suited to promote existing cartilage growth, regrow cartilage and/or prevent bone hypertrophy at a treatment site to promote healing (particularly at the joint-ward end of the device). Additional information to prevent bone hypertrohy is described in U.S. patent application Ser. No. 15/148,894, filed on May 6, 2016, (now published as U.S. Patent Application Publication No. 2016/0250026 A1), the contents of which are incorporated herein by reference.

The first section 12 or joint-ward end of the device further comprises a central aperture 30 within and formed by the central column 24. The central aperture 30 can extend axially completely through the joint ward end 16 as shown particularly in FIG. 9A or can be blind-ended extending only partially through within joint-ward end 16 as shown in FIG. 9D, for example. The central aperture 30 is configured to mate with a driver instrument as disclosed and described below. The central aperture 30 comprises any shape suitable for the intended purpose of the device 10, as will be understood by those with skill in the art with respect to this disclosure. For example, the central aperture 30 may be a square shape, a round shape (FIG. 2A and FIG. 6), a six-pointed star shape (FIGS. 2B, 2C, 2D, 3, 5), a five-pointed star shape (FIG. 7) or a pentagonal shape (FIG. 8), for example. In one embodiment, as shown in FIGS. 2A and 23, the central aperture 30 comprises threads 32 to assist in mating with a driver instrument.

In another embodiment shown in the cross-sectional, side view of FIG. 9D, the hollow central column 1120 of the implantable orthopedic device 10 may include a chamfer 1119. The chamfer is essentially a symmetrical sloping surface at an edge or corner 1118. The chamfer 1119 narrows a diameter of the hollow central column 1120 from a diameter of dd' to a diameter of dd" to compact the central post 1513 of the subchondral bone 1514 when the implantable orthopedic device 10 is placed in the hole over the top of the central post 1513 (as shown in FIG. 15B). The chamfer 1119 at corner 1118 may include an angle of about 45 degrees, for example. The loading of the central post 1513 is increased and/or resorption of the central post is decreased when the central post of the subchondral bone is compacted. Additionally, the chamfer 1119 inhibits formation of bone cysts and/or bone spurs, particularly when the chamfer is used in conjunction with the washer 1111 (FIGS. 11A-11E) or cap 1142 (FIG. 11G) to recreate separation and form a barrier to seal compartments of the device 10. The implantable orthopedic device 10 may include a blind-ended central aperture 30 which extends only partially through a joint-ward end 16 of the device 10 such that synovia (i.e. synovial fluid) leakage is mitigated, discouraged or prevented. It's important to contain the synovial fluid in the joint cavity since the principal role of synovial fluid is to reduce friction between the articular cartilage of joints during movement. Another advantage of this embodiment is that it easily permits backfilling during OATS (i.e. osteochondral autograft transfer system) procedures, when healthy cartilage from a non weight bearing joint is transferred to a damaged area of the knee or other anatomical joint.

Figure 2A:
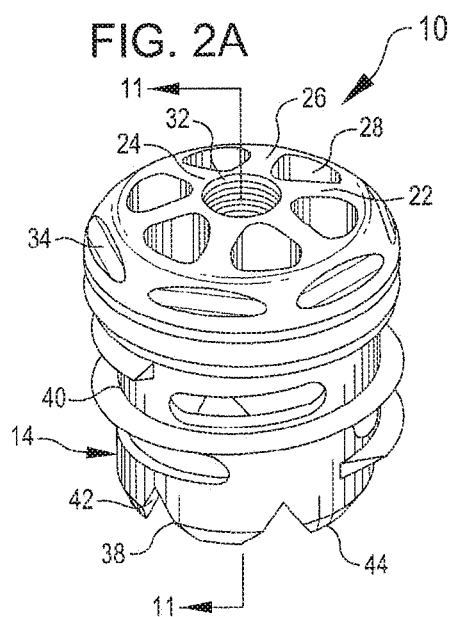
FIGS. 2A, 2B, 2C and 2D are top, lateral perspective views of other embodiments of a device for repairing anatomical joint conditions according to the present invention.
Figure 2B:
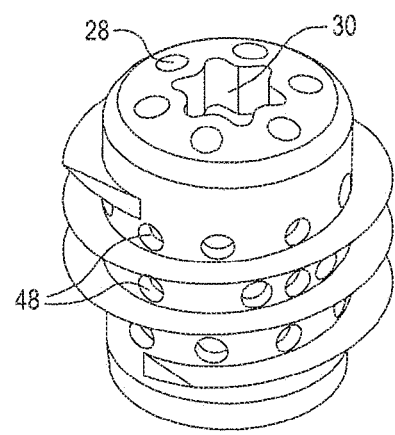
Figure 2C:
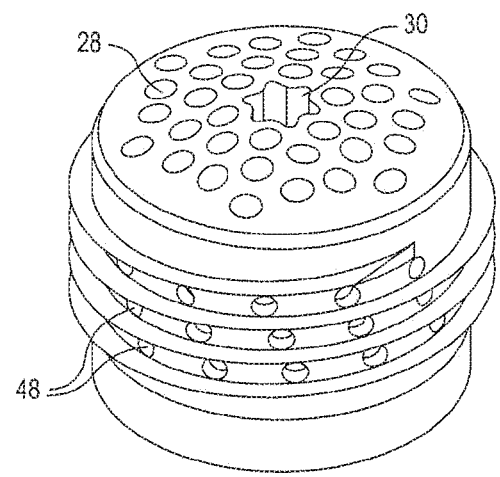
Figure 6:
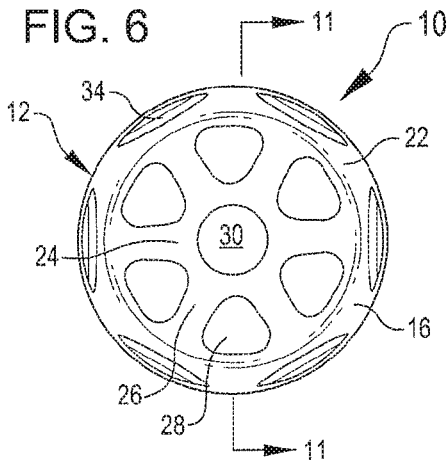
FIG. 6 is a top perspective view of an embodiment of the device for repairing anatomical joint conditions shown in FIG. 2A.

In one embodiment, peripheral column 22 of the first section 12 comprises one or more than one notch 34 as seen in FIG. 2A and FIG. 6. The notches can be used to mate with a driver in addition to the central aperture 30 or instead of the central aperture 30, as will be understood by those with skill in the art with respect to this disclosure.

Figure 11F:
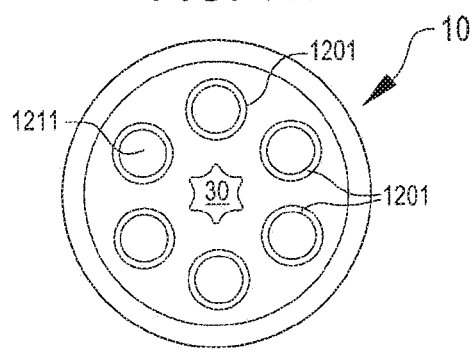
FIG. 11F is a top view of another embodiment of a device for repairing anatomical joint conditions according to the present invention.

The joint-ward end 16 of the first section 12 of the device 10 performs a partial load-bearing and/or load-sharing function post implantation, and comprises a shape suitable to substantially match the shape of the articulation surface that the device 10 recreates on the bone after implantation, as will be understood by those with skill in the art with respect to this disclosure. Therefore, the joint-ward end 16 can have either a convex profile as seen on a cross-sectional, lateral perspective view, as shown in FIGS. 9A-9C, a concave profile as seen on a cross-sectional, side view, as shown in FIG. 10, or even a straight profile. The joint-ward end may have a convex profile having a radius of curvature of between about 10 mm and 50 mm. In one embodiment, a washer is attachable to the joint-ward end of the first section and has a concave, convex, or flat profile as seen on cross-sectional, lateral perspective view (FIGS. 11-11F).

The lateral wall 20 of the first section 12 can be any shape suitable for the intended purpose of the device 10, as will be understood by those with skill in the art with respect to this disclosure. In a preferred embodiment, the lateral wall 20 of the first section 12 comprises a generally convex profile as seen on a cross-sectional, lateral perspective view, as shown in FIG. 9A. This convex profile advantageously provides a smooth transition to and encourages biologic bonding to surrounding cartilage and bone after implantation, as will be understood by those with skill in the art with respect to this disclosure.

The device 10 further comprises a second section 14. The second section 14 of the device 10 comprises a mating end 36, an opposing leading end 38, and a lateral wall 40 extending between the mating end 36 and the leading end 38. The second section 14 further comprises an axial length (cc). The axial length (cc) may be between about 5 mm and 30 mm (FIG. 1Aa). Preferably, the axial length (cc) is between about 6 mm (FIG. 9B) and about 11 mm (FIG. 9C), for example. In one embodiment, the lateral wall 40 of the second section 14 is generally cylindrical as seen in FIGS. 1A and 9A. In another embodiment, the lateral wall 40 of the second section 14 is generally conical, tapering between the mating end 36 and the leading end 38 as seen in FIG. 9B. In one embodiment, the lateral wall 40 of the second section 14 tapers between about 0.2 degrees and 15 degrees and preferably, the lateral wall 40 of the second section 14 tapers about 9 degrees (FIG. 9B).

The mating end 36 of the second section 14 of the device 10 is configured to mate with the mating end 18 of the first section 12 of the device 10. The mating end 18 of the first section 12 and the mating end 36 of the second section 14 can comprise any mating mechanism suitable for the intended purpose of the device 10 can be used, as will be understood by those with skill in the art with respect to this disclosure. In one embodiment, the mating end 18 of the first section 12 and the mating end 36 of the second section 14 mate by a suitable biocompatible adhesive, as will be understood by those with skill in the art with respect to this disclosure. In a preferred embodiment, the mating mechanism is reversible, allowing an interchange of an alternate first section 12 to a specific second section 14 so that the device 10 can be reconfigured as needed for contouring to a particular joint surface, thereby decreasing the number of second sections 14 that need to be stored on site, as will be understood by those with skill in the art with respect to this disclosure. In one embodiment, the mating end 18 of the first section 12 and the mating end 36 of the second section 14 mate by a reversible twist locking mechanism, as will be understood by those with skill in the art with respect to this disclosure. In another embodiment, the first section 12 and the second section 14 are made as a unified whole as shown in FIGS. 9B-9C and are not separable.

The first section 12 and the second section 14 can comprise any material suitable for the intended purpose of the device 10, as will be understood by those with skill in the art with respect to this disclosure. The first section 12 may comprise a material selected from the group consisting of a biocompatible plastic, a biocomposite polymer, a metal and a metal alloy or a material selected from the group consisting of carbon fiber, cobalt chrome, nitinol (e.g. nickel titanium), polycaprolactone (PCL), polyether-ether-ketone (PEEK), tantalum and titanium. In one embodiment, the second section 14 comprises a material selected from the group consisting of a biocompatible plastic, a biocomposite polymer, a metal and a metal alloy. The second section 14 comprises a material selected from the group consisting of carbon fiber, cobalt chrome, nitinol, polycaprolactone (PCL), polyether-ether-ketone (PEEK), tantalum and titanium. The first section 12 may comprise a first material and the second section 14 may comprise a second material, where the first material and the second material are the same or are different materials.

The device 10 can be made by any suitable method, as will be understood by those with skill in the art with respect to this disclosure. In one embodiment, the first section 12 and the second section 14 are machined from modular parts such as by additive manufacturing (AM), direct metal laser sintering (DMLS), selective laser sintering (SLS), selective laser melting (SLM), metal injection molding (MIM), laser engineered net shaping (LENS), 3D printing, 3D bioprinting (i.e. printing using biologic tissues) computer-added design/computer aided manufacturing (CAD/CAM), as will be understood by those with skill in the art with respect to this disclosure. Alternatively, device 10 may be made as a monobloc device. The device 10 may be produced in a customized fashion to correspond to a specific joint anatomy, including bipolar and/or gender-specific differences, for example.

The leading end 38 of the second section 14 of the device 10 is configured to place the device 10 into a prepared space made according to a method according to the present invention. In one embodiment, the leading end 38 comprises a scalloped edge 42. In another embodiment, the leading end 38 comprises bevels 44. The leading end 38 may comprise both a scalloped edge 42 and bevels 44 as shown particularly in FIGS. 1Aa, 1D, 2A, 2D and 3, for example. In one embodiment, the leading end 38 comprises a beveled edge 44 as shown in FIGS. 1B, 1C, and 9D, for example. Alternatively, the leading edge 38 may not comprise beveled edges (FIG. 1Ab). In yet another embodiment, the scalloped edge 42 may be a the shape of the letter "V" rotated 180 degrees (FIGS. 1Ab and 2A) or the shape of the letter "U" rotated 180 degrees (FIG. 2D), for example. In some embodiments, the scalloped edge may be relatively pronounced (i.e. resembling table legs) to reduce material cost and lower the overall profile of the implant (FIG. 1Ab). The implant may include threads 46 along the lateral wall 40 or lack threads as shown in FIGS. 1Aa and 1Ab, respectively.

Figure 3:
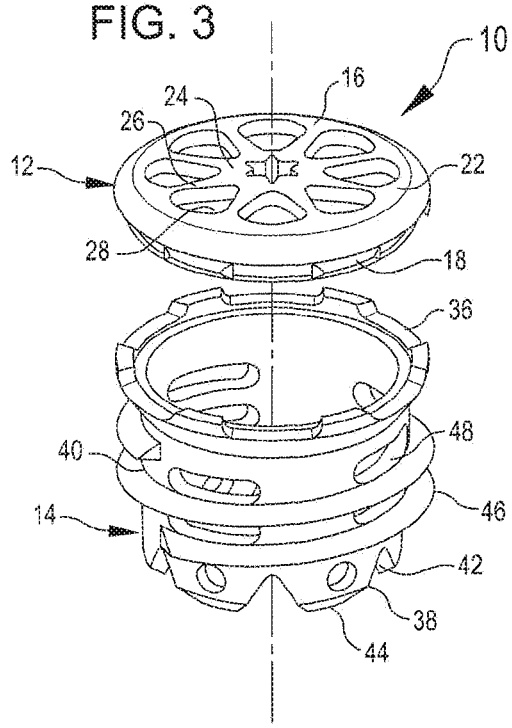
FIG. 3 is an exploded, top, lateral perspective view of the embodiment of the device for repairing anatomical joint conditions shown in FIG. 1Aa.

The lateral wall 40 of the second section 14 of the device 10 extends between the mating end 36 and the leading end 38. The lateral wall 40 of the second section 14 comprises threads 46 for anchoring the device 10 within the bone. In one embodiment, the lateral wall 40 of the second section 14 further comprises a plurality of fenestrations 48 between the threads 46 (FIGS. 1Aa, 1B, 1C and 1D). In a preferred embodiment, the device 10 further comprises a plurality of fenestrations 50 formed by a confluence of the mating end 18 of the first section 12 and the mating end 36 of the second section 14 (FIG. 1Aa and FIG. 3). Each fenestration 48, 50 can comprise any size or shape suitable for the intended purpose of the device 10, including, but not limited to, providing support for different tissue types to promote healing and repair at the treatment site. In a preferred embodiment, the fenestrations may be oval, round, or other shapes. In one embodiment, the lateral wall 40 of the second section 14 is textured to promote bony ingrowth after implantation, as will be understood by those with skill in the art with respect to this disclosure. The fenestrations between the protrusions on the second section of the lateral wall are between about 300 microns and 1200 microns in size to promote bone growth while the plurality of fenestrations on the joint-ward end of the first section are between about 400 microns to 800 microns in size to promote cartilage growth.

The fenestrations may take for form of pores, with each pore sized about 800 microns in diameter to promote bone growth. Pores sized about 500 microns in diameter may be best suited to promote cartilage growth. The external surface of the device is at least partially textured to increase the surface area of the device. The texture may include a dimpled pattern or even a "pattern 701 within a pattern 702" configuration shown in FIG. 7, for example. Another variation of this "pattern 801 within a pattern 802" configuration is depicted in FIG. 8. Of course, a multitude of other such patterns are contemplated and the invention is not limited to the explicit examples provided herewith.

Figure 2D:
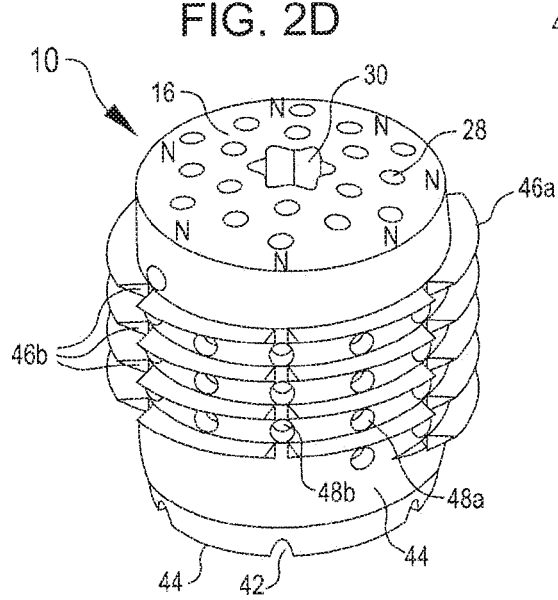
Figure 4D:
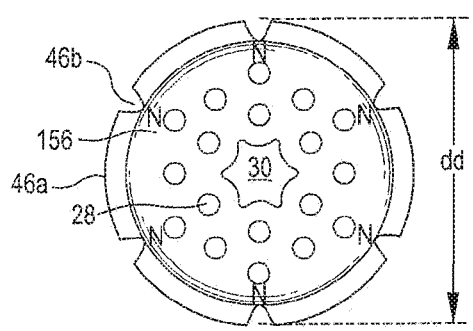
Figure 5:
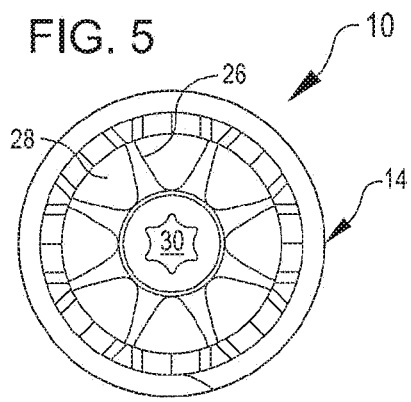
FIG. 5 is a bottom perspective view of the embodiment of the device for repairing anatomical joint conditions shown in FIG. 1Aa.

As shown FIGS. 1D, 4D, and particularly in FIG. 2D, a plurality of fenestrations 48a, 48b are located between the threads 46a including at least some fenestrations 48b positioned in vertical alignment with notches 46b. The notches are located along (i.e. track) the spiral thread path. The notches 46b are intermittently spaced along the threads path and intermittently interrupt the thread path. In this embodiment, one end of a suture or similar materials may be threaded through the fenestrations(s) 48b on one side of the device 10 and secured in place with a knot, clip or other fastener at each fixation point. The other end of the suture may be wrapped over the joint-ward end 16 and threaded (i.e. inserted) through fenestration(s) 46b on another side of the device 10 to substantially hold a biomaterial in place on the top of the joint-ward end 16 of the device. The discussion below with respect to FIGS. 11Ha through 11Hi elaborates on this particular embodiment.

Referring to FIG. 10, the joint-ward end 16 may be concave. A washer 1111, 1121, 1131 may be attached to the joint-ward end of the device via threads 1141, spikes 1151 or snap-fit 1161 as shown in FIGS. 11B-11D, respectively. The threads may include reverse cutting threads, notched threads, tapered threads, buttress threads, metric threads, trapezoidal threads, acme threads, pipe straight threads, unified threads, custom threads and multi-threads. The washer may have a convex 1611, concave 1612, or flat 1613 geometric surface. The washer 1111 may also be slid in direction 1181 such that tracks 1171 meet and engage the corresponding groove 1191 of the device 10 to secure the washer 1111 together as depicted in FIG. 11E, for example. FIG. 11F is a top view of the joint-ward end of device 10 showing chambers 1201 that may hold a carrier substance 1211 such as a polymer, or biomaterial, or medicine, or a hybrid combination thereof. The biomaterial may include cartilage, osteocartilage, a chemotactic substance or a cellular differentiation substance (including stem cells), for example. The medicine may include an antimicrobial, antibiotic, antiviral or chemotherapeutic agent, for example. The therapeutic biomaterial may possess chemotactic, cellular homing, biological crosstalk and/or time-release capabilities and promote tissue growth, encourage bleeding and inhibit infection to facilitate repair of the anatomical joint.

Figure 11G:
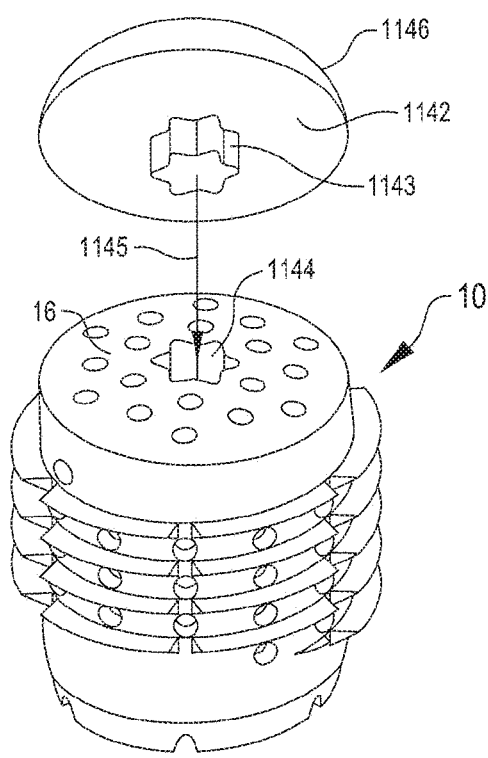
FIG. 11G is a lateral perspective view of another embodiment of a device for repairing anatomical joint conditions according to the present invention.

FIG. 11G depicts another embodiment wherein a cap 1142 may be secured to the joint-ward end 16 of the device 10 via snap-fit arrangement 1145. A male portion 1143 of the cap 1142 engages a female portion 1144 of the joint-ward end 16 of the device 10. The cap 1142 may hold a carrier substance 1146 containing a polymer, or biomaterial, or a hybrid combination thereof.

Figure 11H:
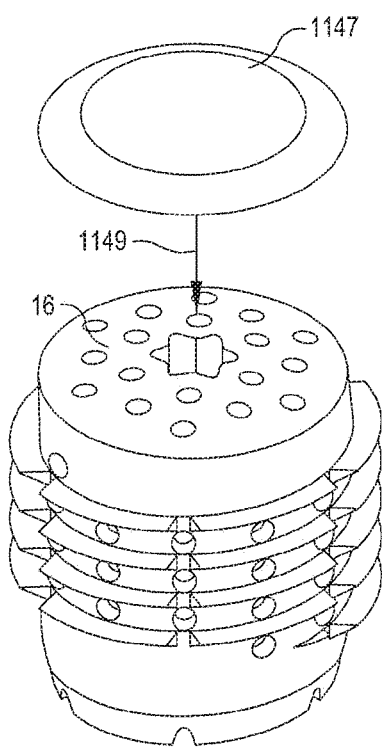
FIGS. 11Ha-11Hc are lateral perspective views of alternative embodiments according to the present invention.
Figure 11H:
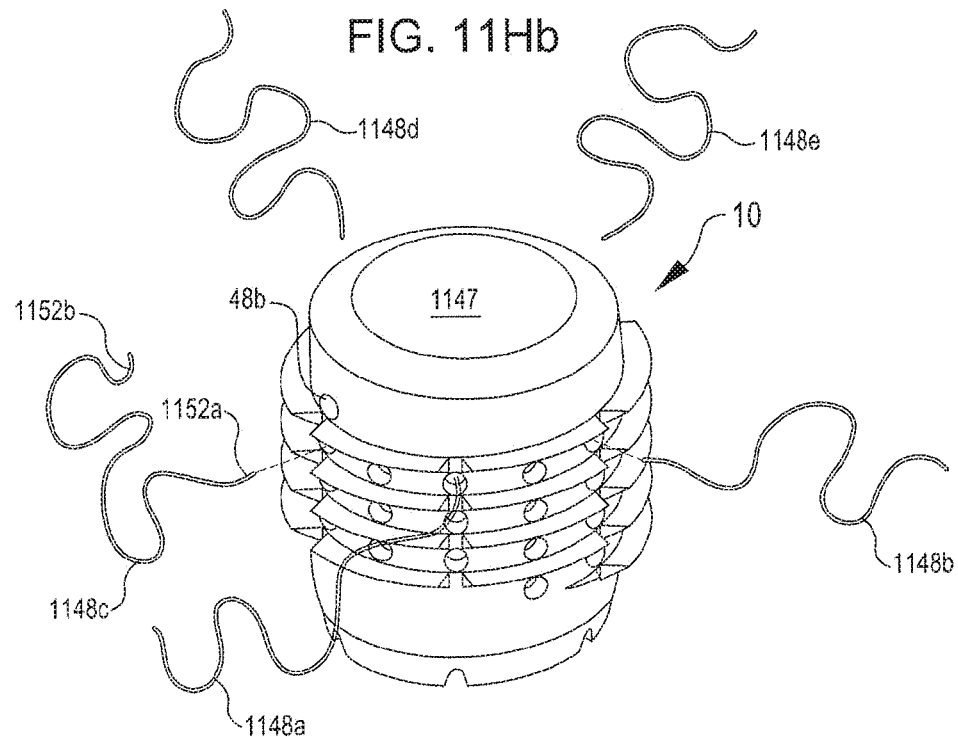
Figure 11H:
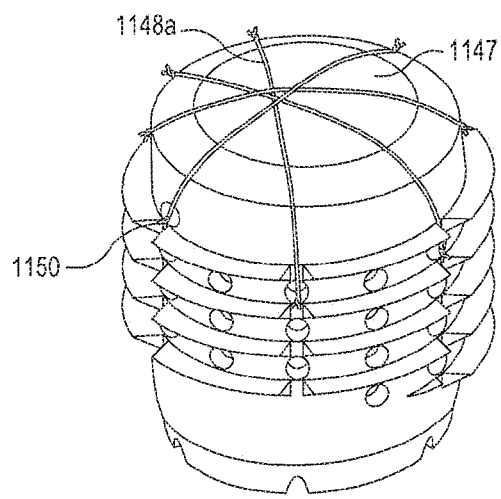
Figure 11H:
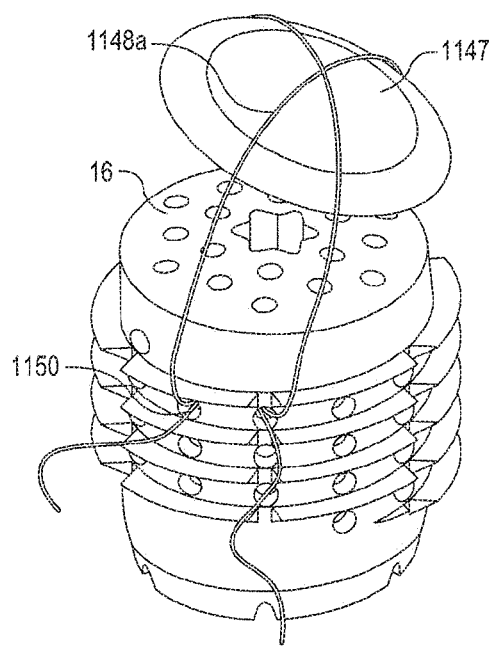
Figure 11H:
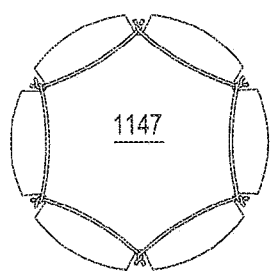
Figure 11H:
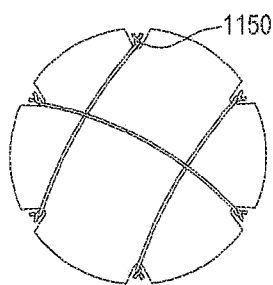
Figure 11H:
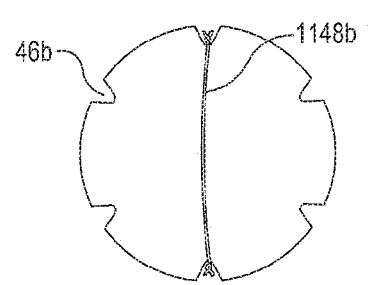
Figure 11H:
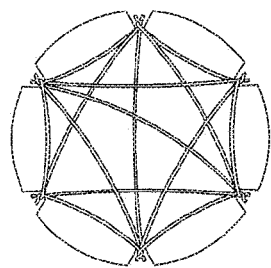
Figure 11H:
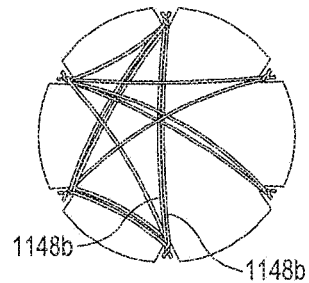
Figure 11H:
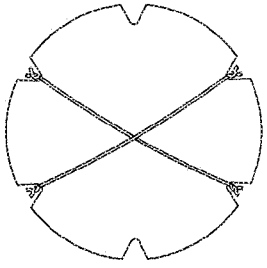
Figure 11H:
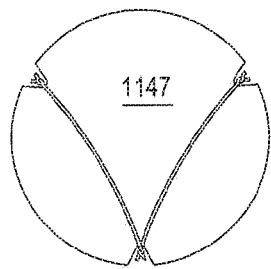
Figure 11H:
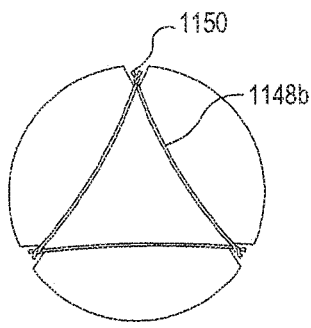
Figure 11H:
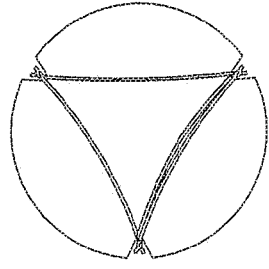

As shown in the sequence of FIGS. 11Ha-11Hc, a carrier substance 1147 may be positioned 1149 substantially over (e.g. on top of) the joint-ward end 16 of the device 10 and fastened into place using one or more strands 1148a, 1148b, 1148c, 1148d, 1148e. The strands may include suture material including absorbable sutures (e.g. polyglactin, poligle- caprone, polydioxanone) and non-absorbable sutures (e.g. nylon, dacron, silk, polypropylene), as well as elastic bands, laces, strings, tethers, or similar material. The strands may be substantially round, oval or flat in cross sectional area and may be bonded to, or impregnated with, therapeutic agents. The strands may additionally include an aglet 1152a at one or both ends of the strand 1152b to facilitate threading the strand 1148c through fenestration 48b After threading the strand end 1152a through fenestration 48b, the end may be attached by a knot 1150 or other securing contrivance. The opposite end 1152b (i.e. non-secured end) of the strand 1148c is looped across the carrier substance 1147 and the end 1152b is threaded through a fenestration opposite (or adjacent) the fenestration 48b and anchored in place using a knot or other fastener to secure the strand substantially taut with a sufficient tensile strength across the joint-ward end 16 to hold the carrier substance 1147 in place. The carrier substance and/or one or more strands may be secured pre- or post-implantation of the device 10 into the bone. If the one or more strands are attached in a configured pattern before the carrier substance 1147 is positioned, strand(s) with some elastic properties may be preferred to allow the strand(s) to be lifted (i.e. stretched upward away from the joint-ward end 16 of the device) to create a sufficient space to allow the carrier substance to be tucked into position under the strand(s), for example. Sliding self-locking sutures may also be employed.

Should the strands be secured post-implantation, at least one level of fenestrations need to be accessible to secure the strands. When the implant is secured substantially flush with the joint articulation, exposing at least one row of fenestrations and notched threads can be accomplished by clearing tissue around the circumference of the implanted device using a reamer or other instrument. In one embodiment of the invention, indications 156 may be included on the top surface of the joint-ward end 16 of the device to assist in visually locating the notches and fenestrations when the device is implanted substantially flush with the hone surface. One example of the indication 156 is shown in FIG. 4D where the indication is an engraved "N". The strands may also be secured while the device is only partially implanted and the device can subsequently be implanted substantially flush after the strands have been attached. In this manner, removal of tissue around a circumference of the device to access the fenestrations is minimized or avoided. The notches 46b between the threads 46a serve as guides for the strands, including sutures and keep them in place to prevent their migration (i.e. rolling, sliding) to the right or left side of the fenestration to which they are attached. The notches 46b in this particular embodiment also prevent the sutures from running over and across the sharp threads. In this manner the notches reduce the risk of the strand becoming weakened (e.g. frayed or severed), for example.

As shown in FIG. 11Hm, a carrier substance 1147 may be preloaded on the device 10. The word "preloaded" refers to an embodiment where the carrier substance 1147 is attached to the device 10 before the device is partially or fully implanted at a treatment site (i.e. bone defect). One advantage of preloading the carrier substance is that it saves time during the procedure. In this embodiment, the carrier substance 1147 is attached to an edge of the joint-ward end 16 of the device. The attachment may be made with one or more strands or other attachment means. In this manner, the carrier substance 1147 can be visualized as a "lid flap", for example. The strand(s) 1148a are loosely attached to another side (or sides) of the device with some slack so that the carrier substance 1147 is positionable off center relative to the central aperture 30. This leaves the central aperture 30 accessible to the driver instrument. After the device has been implanted at the treatment site and the driver instrument has been removed, the carrier substance 1147 is cinched down substantially over (e.g. on top of) the joint-ward end 16 of the device 10 by pulling on the loosely attached strand(s) to remove the slack. The strand(s) may then be secured in place with a knot, sliding self locking sutures, or other means of attachment 1150. The strands may include suture material including absorbable sutures (e.g. polyglactin, poliglecaprone, polydioxanone) and non-absorbable sutures (e.g. nylon, dacron, silk, polypropylene), as well as elastic bands, laces, strings, tethers, or similar material. The strands may be substantially round, oval or flat in cross sectional area and may be bonded to, or impregnated with, therapeutic agents.

The configuration of strands shown in FIGS. 11Ha-11Hc include a total of 5 separate strands positioned in an "asterisk" pattern (FIG. 11Hc). However, a multitude of other patterns are contemplated base on various factors and considerations. These considerations may include, but are not limited to, the thickness of the carrier substance, the composition of the strand material, the area of the bone defect in proximity to the joint-ward end of the device, and the preference of the surgeon, for example. Many of these considerations are specific to the individual repair and associated anatomy. A few examples of suture patterns using a six-point suture fixation attachment, including a "hexagon" (FIG. 11Hd), "letter H" (FIG. 11He), "single strand" (FIG. 11Hf), "geometric trampoline" (FIG. 11Hg), "random web" (FIG. 11Hh), and "letter X" (FIG. 11Hi) are shown in top views of FIG. 4D after the carrier material 1147 has been positioned. In this embodiment, the carrier material is attached to the device without disturbing the surrounding cartilage.

More than a single suture may be weaved, stitched or otherwise positioned across the same area in the same direction as shown by sutures 1148*b*, 1148*b'* in FIG. 11Hh, for example. This pattern offers additional strength on the left side to hold the carrier material 1147 in place in this particular example. It is also contemplated that several embodiments may be combined to secure the carrier substance in place. For example, the snap-fit cap shown in FIG. 11G may additionally be sutured according to embodiments shown in FIGS. 11Ha through 11Hi.

In addition to suturing the carrier substance to the implant, the carrier substance may be bonded to the implant using adhesives or coated on the implant. One such coating may include hydroxyapatite (HA), for example. Regardless of how the carrier substance is attached to the implant, the carrier substance may be secured to the implant either before or after implantation of the device 10 into the bone.

It will be appreciated that there are numerous stitches and suture threading patterns that may be employed to secure a carrier substance containing a polymer, or biomaterial, or medicine or a hybrid combination thereof to an implantable orthopedic device according to the methods and devices described herein. Additionally, the suture fixation is not limited to six-point fixation attachment and may be attached using sutures attached at three fixation points rather than six, for example, as shown in FIGS. 11Hj through 11Hl. These variations as well as variations in the design of the above-described devices and instruments are within the scope of the present disclosure.

Turning now to FIG. 12A, flares 1299 may be used to firmly attach the device 10 to the bone. The flares 1299 may be used alone or in combination with threads 46. Furthermore, the flares may be located on the outside of the device 1299 or on the inside of the device 1298 (FIG. 12B) or a combination of thereof. The flares 1298, 1299 can also be used in combination with threads 46 to anchor the device 10 securely to the bone.

One or more vascular channels may be created in the subchondral bone at the treatment site to facilitate beneficial bleeding. These vascular channels 1511, 1512 are shown in FIG. 15B, for example. The vascular channels are created by drilling, reaming, tapping, boring, or poking into the bone. It has been found that some minor bleeding actually promotes healing as the blood wicks upward toward the treatment site. In this regard, FIGS. 13A and 13B are top views of groove configurations on the inside (FIG. 13A) or outside (FIG. 13B) of device 10 to allow blood wicking. As seen in FIG. 13C, the grooves may be arranged in a vertical configuration 1313 on the device with each groove substantially parallel to a neighboring groove. Spiral configurations 1314 (FIG. 13D) and many other groove configurations are contemplated.

Figure 14A:
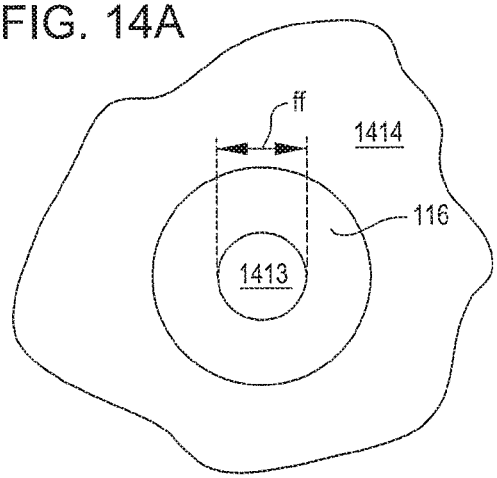
FIG. 14A is a top perspective view of an embodiment of a device for repairing anatomical joint conditions according to the present invention.
Figure 14B:
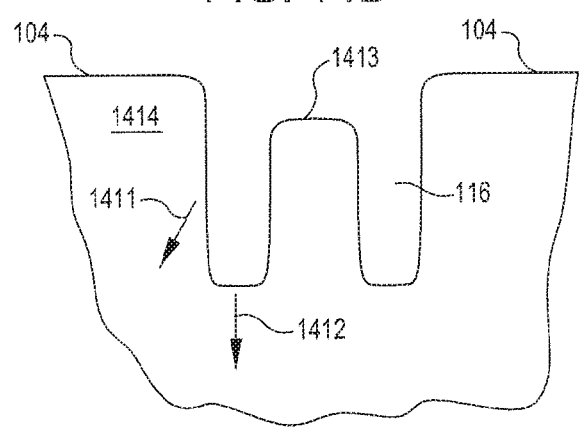
FIG. 14B is a side view of an embodiment of a device for repairing anatomical joint conditions according to the present invention.

According to an embodiment of the invention, an anatomical joint condition is repaired by removing an inner circular portion of the subchondral bone to create a space 116 while preserving a central post 1413 of subchondral bone a substantially undisturbed native state using a cannulated drill or other similar orthopedic instrument. FIG. 14A is a top view of the central post 1413 and the surrounding bone 1414. FIG. 14B is basically a side view of FIG. 14A showing the central post 1413 and space 116. After the space 116 is created, vascular channels may be made in a relatively deeper vertical direction 1412 and/or made in an angled direction 1411 to provoke bleeding. See also channels 1511 and 1512 in FIG. 15B.

Figure 15A:
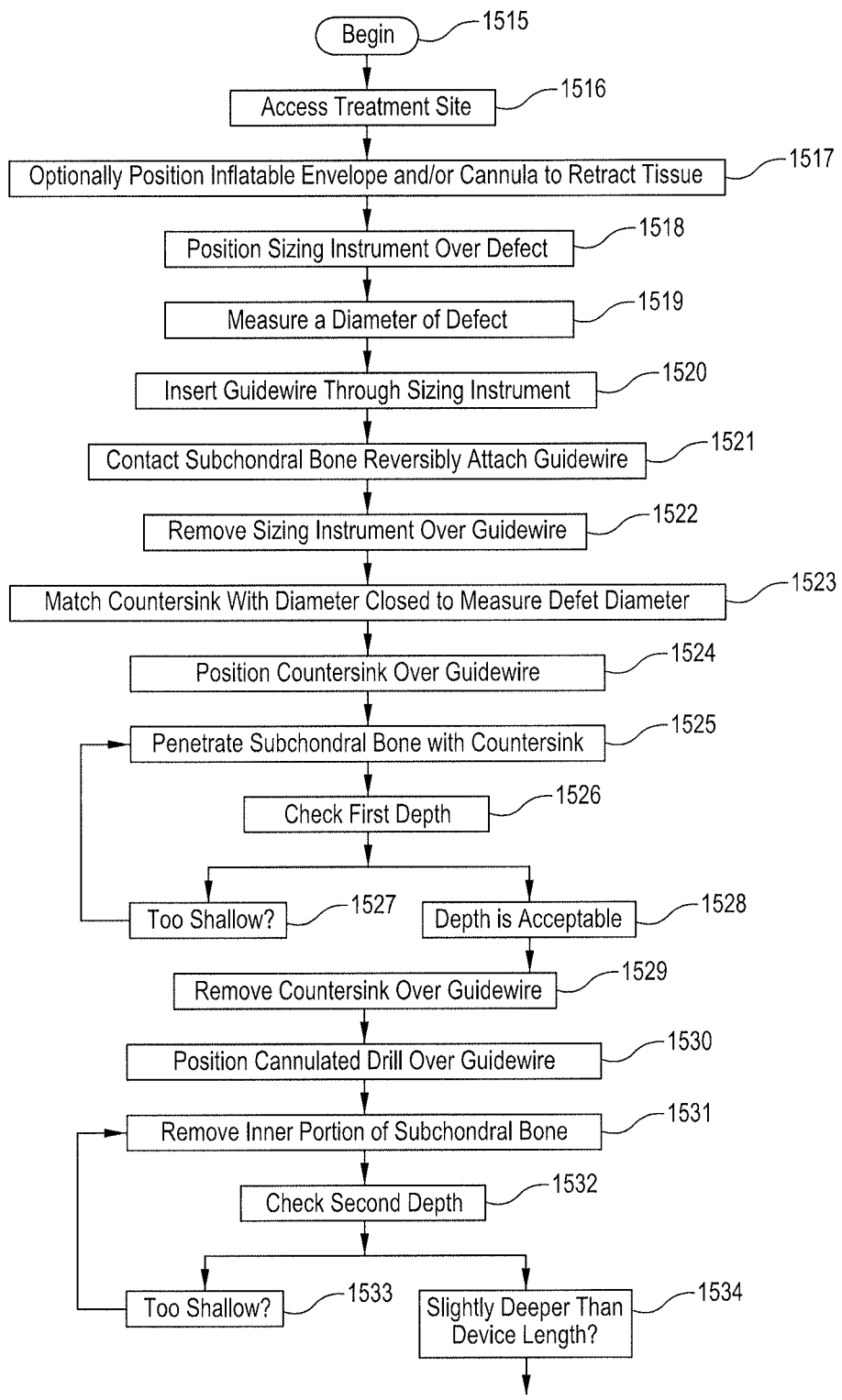
FIG. 15A (presented in subparts 15Aa and 15Ab on separate sheets) is a flow chart diagram of an embodiment of a method for repairing anatomical joint conditions according to the present invention.
Figure 15A:
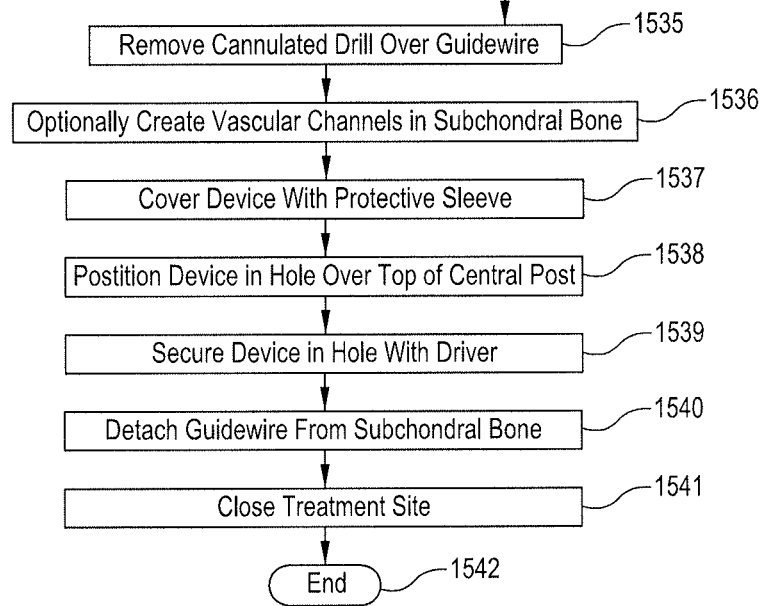
Figure 15B:
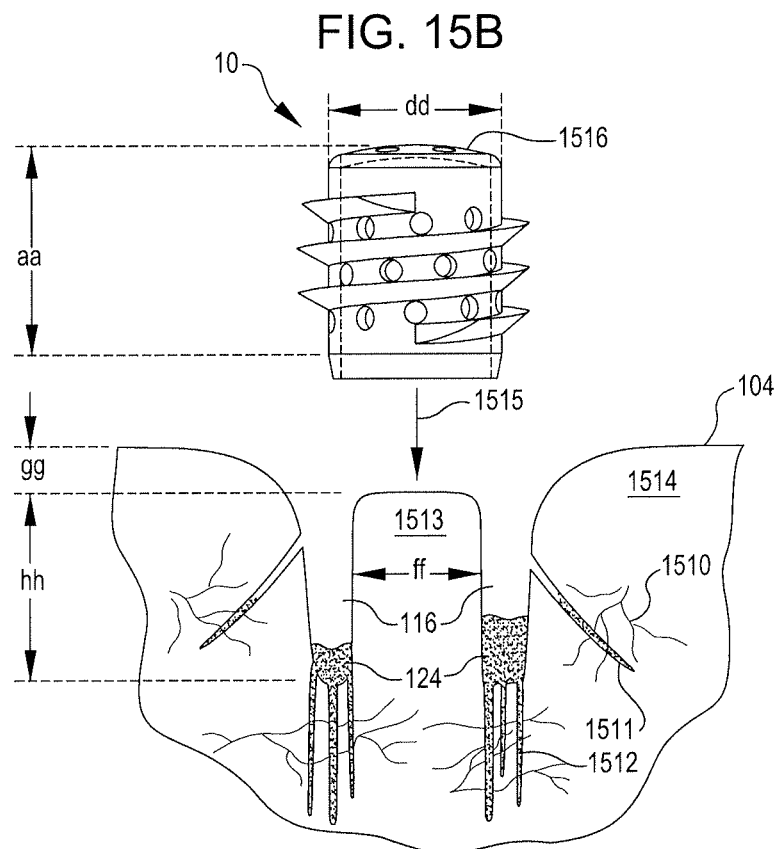
FIG. 15B is a cross section diagram depicting an embodiment of a method for repairing anatomical joint conditions according to the present invention.

FIG. 15A (presented in subparts 15Aa and 15Ab on separate sheets) is a flow chart outlining steps to repair an anatomical joint condition using the present invention. The surgeon begins the procedure 1515 by surgically accessing the treatment site 1516. Optionally, an inflatable envelope and/or a cannula may be positioned to retract the tissue so as to have better access to the treatment site 1517. A sizing instrument is centrally positioned over the defect at the treatment site on the subchondral bone 1518. A diameter of the defect is measured with concentric rings on the sizing instrument by comparing the defect diameter with the closest corresponding known diameter on the sizing instrument 1519. A guidewire is inserted through the lumen of the cylindrical member while the distal end of the sizing instrument is centrally positioned over the defect 1520. The subchondral bone is contacted with a distal end of the guidewire and the center of the defect is marked by reversibly attaching the guidewire to the subchondral bone 1521. Next, the sizing instrument is removed over the guidewire 1522. A countersink instrument is selected that has a diameter substantially matching the measured diameter of the defect 1523. The countersink instrument is positioned over the guidewire 1524. The thickness of the countersink mimics the thickness of the joint-ward end of the implant. By simultaneously rotating and lowering the countersink to engage a soft tissue and the subchondral bone, the subchondral bone is penetrated with the countersink to form a hole 1525 having a first depth. The first depth is checked 1526. If the hole is too shallow to allow placement of the device 1527 at a desired depth, the step 1525 is repeated. If the desired depth is acceptable (i.e. the device is flush with the bone surface, countersunk slightly below the bone surface, or slightly protruding above the bone surface as shown in FIGS. 16Ta-16Tc, respectively), the first depth may be considered acceptable 1528 and the countersink may be removed over the guidewire 1529. A cannulated drill is positioned over the guidewire 1530. An inner circular portion of the subchondral bone is removed 1531 while preserving a central post of subchondral bone in an substantially undisturbed native state by simultaneously rotating and lowering the cannulated drill into a center of the countersink hole. The inner circular portion has a second depth which is checked 1532. If the second depth is too shallow, step 1531 may be repeated. If the second depth is found to be slightly deeper that the device length 1534, then the cannulated drill can be removed over the guidewire 1535. At this stage, one or more vascular channels may be created in the subchondral bone 1536. Next, a protective sleeve is optionally placed over an implantable orthopedic device 1537 and the device is implanted in the patient. The device is positioned in the hole over a top of the central post and the sleeve is removed 1538. The central bone post is accepted by a hollow central column of the device when positioned/implanted. The orthopedic device is secured in the hole using a driver instrument 1539 and the driver instrument is removed. The guidewire is detached from the subchondral bone 1540 and the guidewire is removed. The treatment site is closed 1541 at the conclusion 1542 of the repair procedure.

FIG. 15B is a cross section of one embodiment of the present invention for repairing an anatomical joint. For purposes of the following narrative, the bone 1514 will be referred to as a subchondral bone at a knee joint; however, the following description could be used for any bone requiring anatomical joint repair. The subchondral bone 1514 surface 104 has been prepared at the defect site by penetrating the bone with a countersink instrument to a first depth gg and removing an inner circular portion of the bone using a cannulated drill to a second depth hh while keeping a central post of subchondral bone 1513 fundamentally intact and substantially undisturbed. By removing an inner circular portion of bone, a circular space 116 is created. Preserving the central post 1513 provides structural integrity to the treatment site and facilitates repair since less bone is removed. The second depth hh encourages blood flow 124 around the walls of the central post 1513. Vascular channels 1511, 1512 may be created at various angles and depths to tap into the vasculature (i.e. capillary bed) 1510 to promote bleeding 124. Bleeding may include laminar blood flow, turbulent blood flow, capillary blood flow, and percolatory blood flow, for example.

An implantable orthopedic device 10 is placed over the top of the post 1513 as shown in direction 1515. The width dd of the device 10 may be slightly wider that the width ff of the post 1513. The length aa of the device 10 may be slightly less than or equal to the second depth hh to allow sufficient placement of the device 10. The central post 1513 accepts the hollow central column of device 10. When device 10 is fully implanted, the joint-ward end 1516 of device 10 is substantially flush with the surface 104 of the subchondral bone 1514 (e.g. the first depth gg allows placement of the device 10 at an substantially flush orientation with the bone surface 104) via countersink hole. In some situations, as shown in FIG. 16Tb, the joint-ward end 1516 of the device 10 may be implanted slightly below a surface 104 of the subchondral bone 1514 to account for a thickness of a carrier substance that may optionally be attached to the joint-ward end of the device either pre- or post-implantation. The inner circular portion of removed bone (i.e. space 116) has a diameter less than or equal to the diameter of the countersink hole.

According to another embodiment of the present invention, there is provided a method for repairing an anatomical joint condition or disease in a patient. Referring now to FIGS. 16A through 16L, there are shown schematic depictions of some steps of a method for repairing anatomical joints and ameliorating joint conditions and diseases, as well as preparing a defect at a treatment site on a subchondral bone to repair an anatomical joint according to the present invention. In this example, the figures illustrate one embodiment of the method being used on a femorotibial joint 100 to ameliorate an arthritic condition which has caused a defect 102 on an articulation surface 104 of a bone or joint, shown here as on the medial condyle 106 of the femur 108.

A patient is first identified with a joint condition or disease that is suitable for treatment by the present method, where the joint comprises a bone with a surface comprising a defect caused by the joint condition or disease. Diagnosing the patient may include performing one or more than one action, including performing a physical examination, performing a non-invasive imaging examination (such as magnetic resonance imaging, computerized tomography and ultrasound), performing arthroscopy or simply consulting patient records to determine if the patient has a joint condition or disease suitable for treatment by the present method. As will be understood by those with skill in the art with respect to this disclosure, the joint can be any joint with a hyaline cartilage bearing surface, joint capsule, and synovial fluid. The joint may be a diarthrodial joint (i.e., synovial joint). In one embodiment, the joint is selected from the group consisting of an acetabulofemoral joint, an acromioclavicular joint, a femoropatellar joint, a femorotibial joint, a glenohumeral joint, a humeroradial joint, a humeroulnar joint, an interphalangeal joint, a metacarpal joint, a radioulnar joint and a talocrural joint. In one embodiment, the patient may be a human or a non-human animal. In a preferred embodiment, the joint condition and disease is selected from the group consisting of arthroses, chondromalacia patella, isolated chondral defect, juvenile idiopathic arthritis, ligamentous deficiency arthroses, osteoarthritis (degenerative arthritis or degenerative joint disease), osteonecrosis, osteochondritis dissecans, patellar instability, post-ligamentous injury arthritis, post-meniscectomy arthritis, post-meniscectomy arthroses, post-traumatic arthritis, septic arthritis, rheumatoid arthritis and genetic defects. In one embodiment, identifying the patient comprises diagnosing the patient with a joint condition and disease.

The method further comprises accessing the joint treatment site 100 via arthroscopy or by an open surgical procedure, such as for example a mini-open procedure.

Figure 16A:
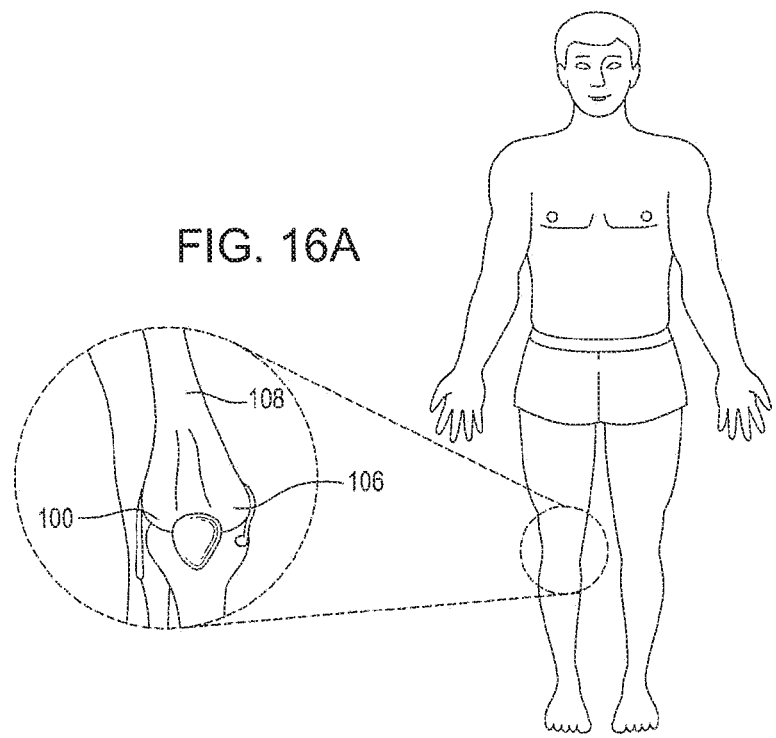
FIG. 16A through FIG. 16V are schematic depictions of some steps of a method for repairing anatomical joint conditions according to the present invention.
Figure 16B:
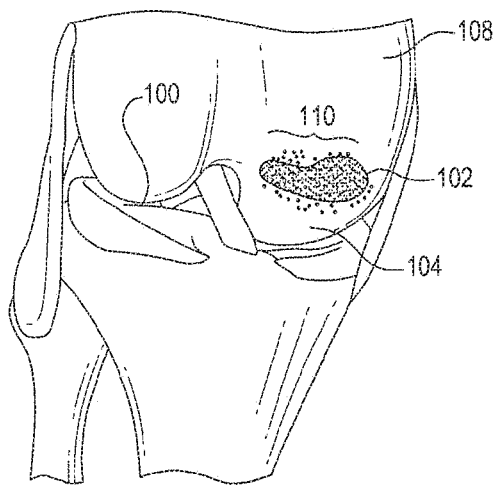
Figure 16C:
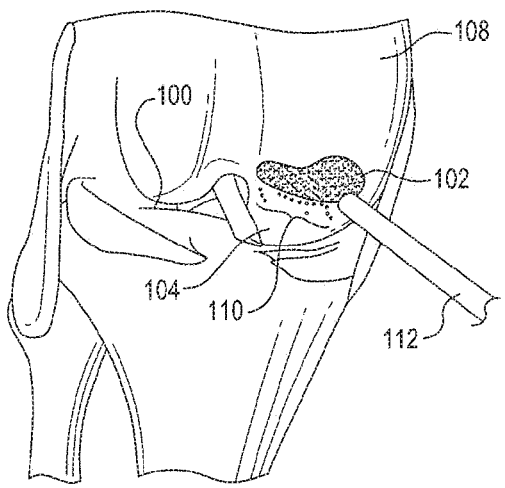

As shown in FIGS. 16B and 16C, the surface 104 of the bone includes an abnormality (i.e. defect) 110 (such as for example area cartilage softening, thinning, damage, or absence), and a burr and/or a suction shaver 112 may be used to remove some or all of the abnormalities 110 thereby creating a smoother articulation surface 104 as shown in FIG. 16C.

Figure 16D:
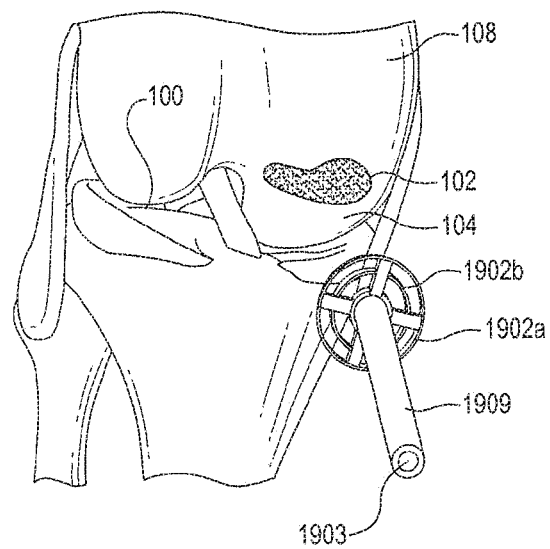

As shown in FIG. 16D, the distal end of a sizing instrument 1909 is placed over the defect 102 to measure the defect using the concentric rings 1902*a*, 1902*b* on the sizing instrument by comparing the defect 102 diameter with the closest corresponding known ring diameter 1902*a*, 1902*b* on the sizing instrument 1909.

Figure 16E:
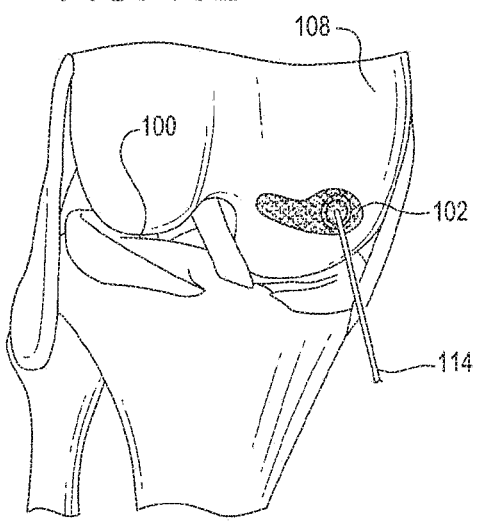

The method further comprises inserting a guidewire 114 through the lumen 1903 of the sizing instrument 1909 when the sizing instrument is positioned over the center of the defect 102. The distal end of the guidewire 114 contacts the bone and reversibly attaches to the bone to mark the center of the defect 102. The sizing instrument 1909 is removed over the guidewire 114 while the guidewire 114 remains attached to the bone as shown in FIG. 16E.

Figure 16F:
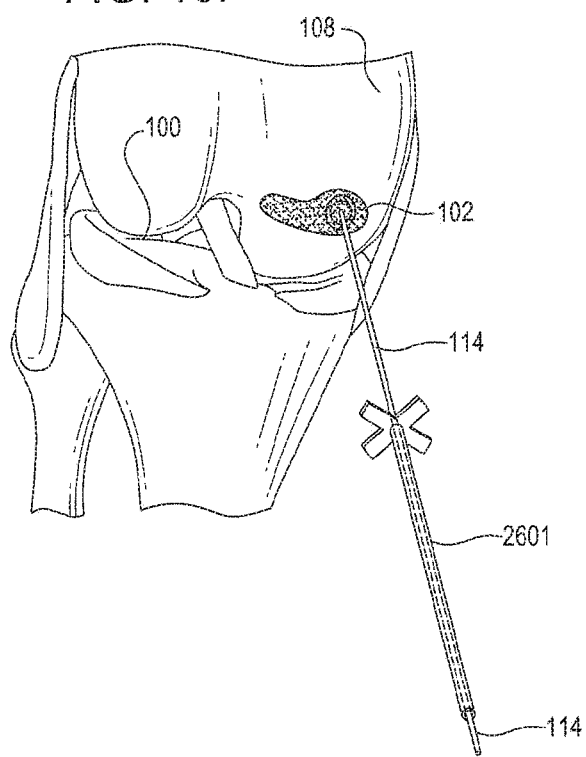
Figure 16G:
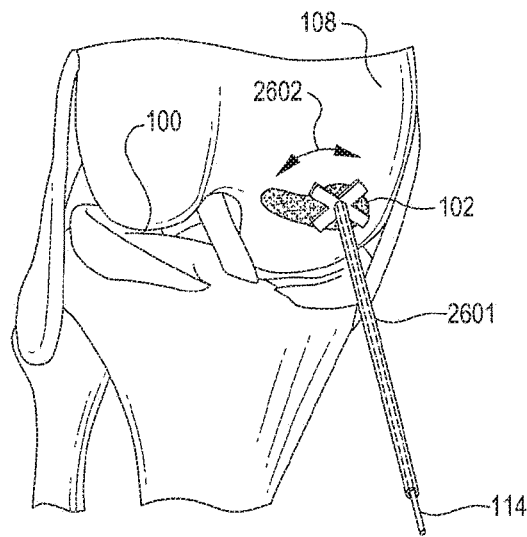

A countersink instrument 2601 is positioned over the guidewire 114 and moved onto contact the defect 102 (FIG. 16F). As shown in FIG. 16G, the countersink instrument 2601 is rotated 2602 to remove soft tissue and some bone to a given depth. The countersink is removed over the guidewire when a sufficient depth has been determined.

Figure 16H:
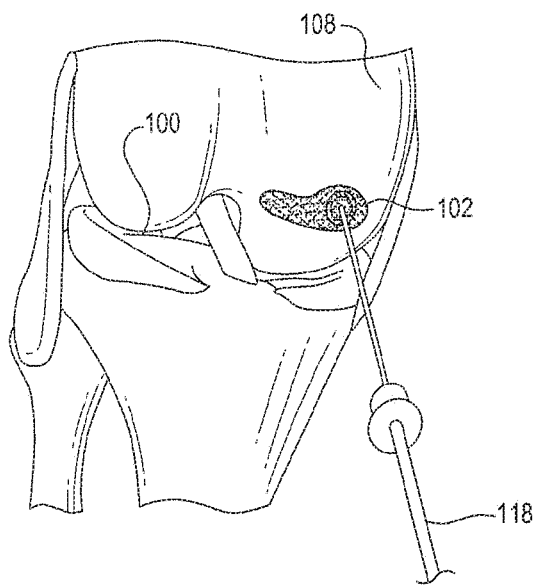
Figure 16:
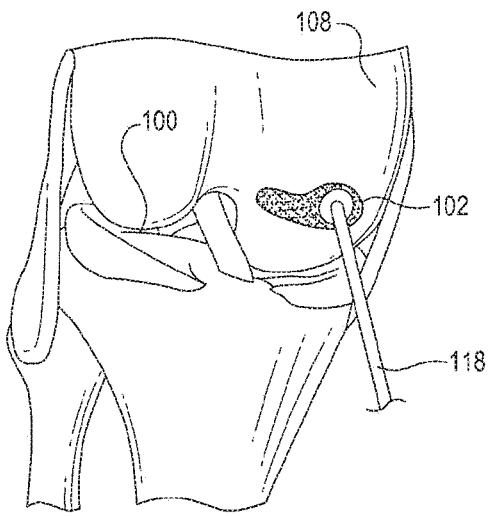
Figure 16J:
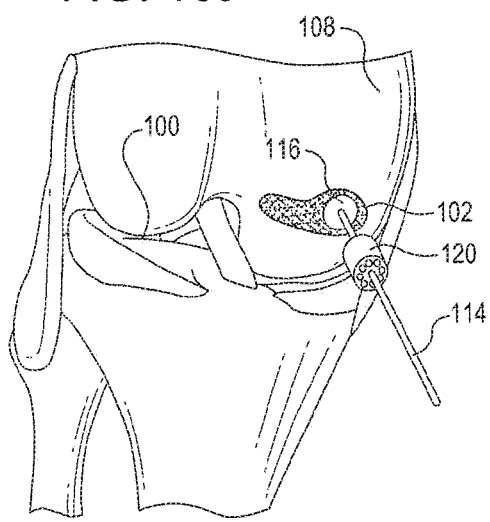

Next, the method further comprises creating a space 116 in the defect 102 of the bone for a device. In one embodiment, the space 116 is created using a cannulated drill 118 placed over the guidewire 114 to core and plane the surface of the defect 102 as shown in FIG. 16H, and FIG. 16I. The cannulated drill 118 is then removed leaving the guidewire 114 in place.

Figure 16K:
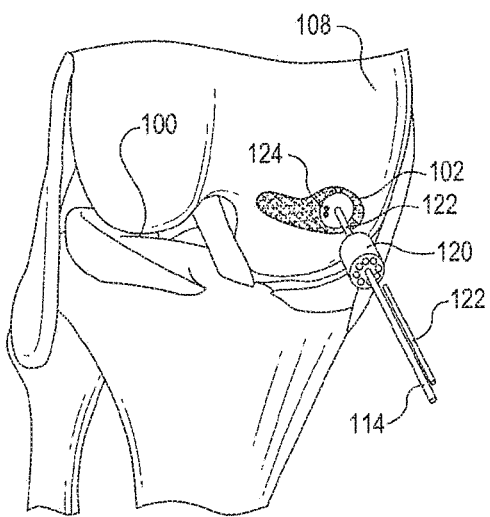
Figure 16L:
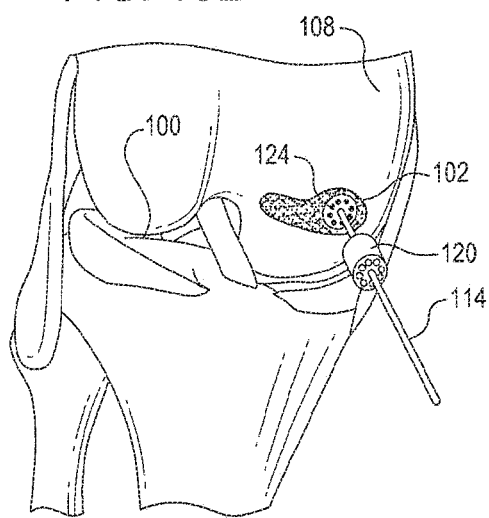

In one embodiment, the method further comprises creating one or more vascular channels in the bone deep to the space 116 using a drill bit guide 120 positioned over the guidewire 114 (FIG. 16J) and a drill bit 122 passed within the drill bit guide 120 (FIG. 16K). Confirmation of creation of the one or more vascular channels is made by the presence of blood 124 leaking into the space 116 from the one or more vascular channels as shown in FIG. 16L, for example. The drill bit guide 120 and drill bit 122 are then removed leaving the guidewire 114 in place.

Figure 16M:
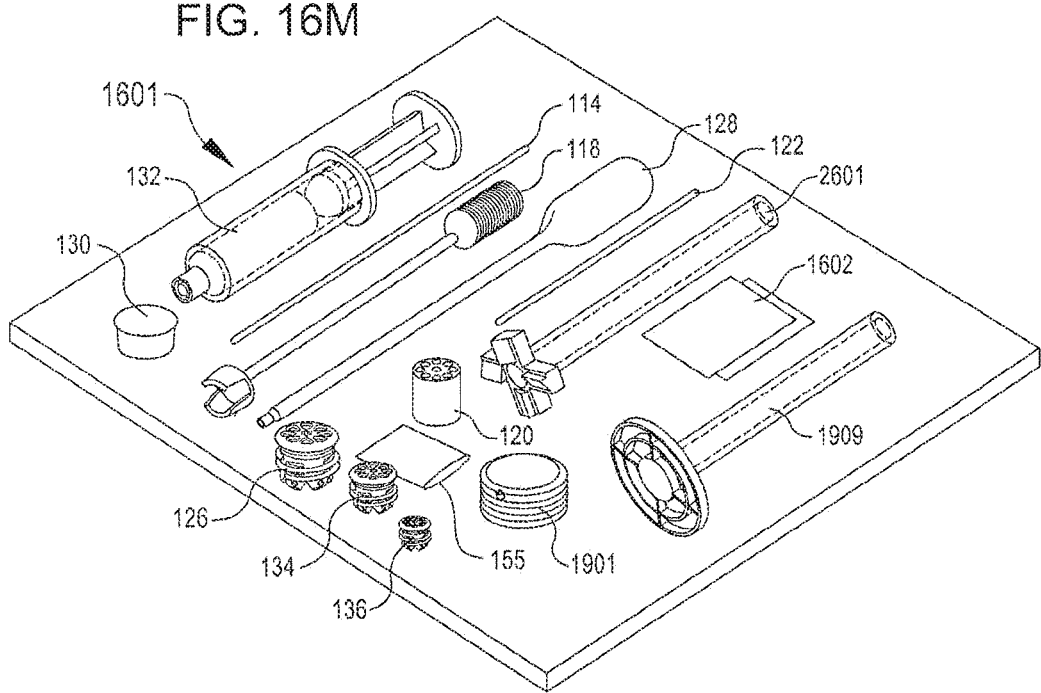
Figure 16N:
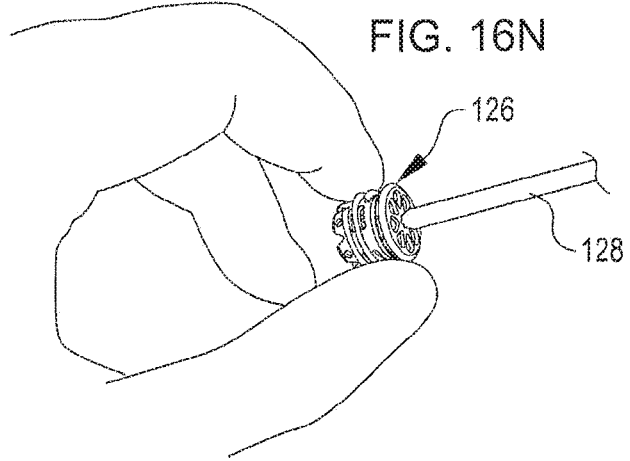
Figure 22A:
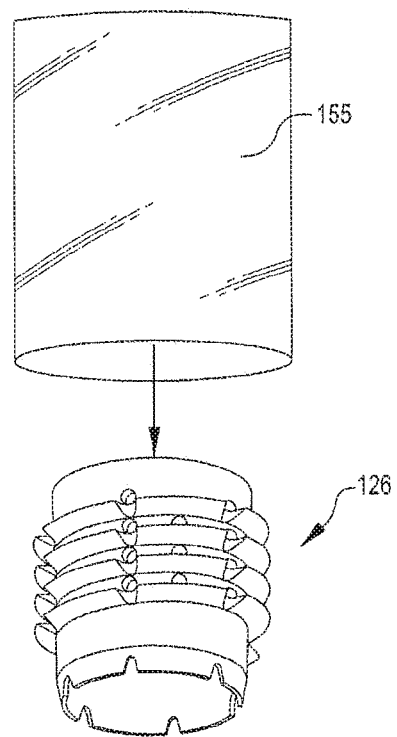
FIGS. 22A and 22B are perspective views of a protective sleeve for covering the implantable orthopedic device according to embodiments of the present invention.
Figure 22B:
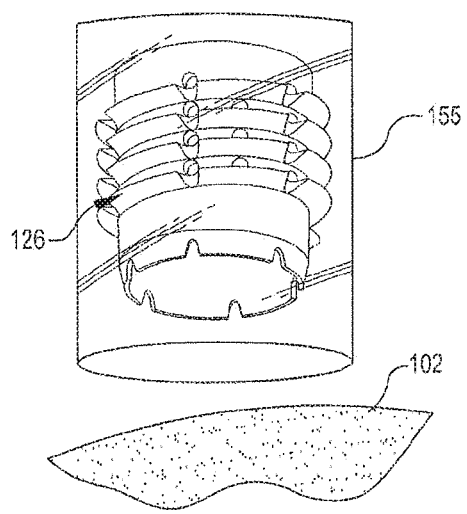

Next, the method further comprises providing a first device 126 for repairing joint conditions suitable for ameliorating the joint condition or disease of the patient as can be seen in FIG. 16M which includes a sterilizable kit containing packaging 1601, instructions 1602 and other instruments and materials for repairing joint conditions as described herewith. In one embodiment, the first device 126 is a device according to the present invention. The first device 126 provided has a size suitable for incorporation into the space 116 made in the defect 102, and the joint-ward end of the first device 126 comprises a shape suitable to substantially match the shape of the articulation surface 104 that the first device 126 recreates on the bone after implantation, as will be understood by those with skill in the art with respect to this disclosure. Referring now to FIG. 16N, the first device 126 is attached to a driver 128, such as for example by mating the distal end of the driver 128 with the central aperture of the first device 126. In one embodiment as shown in FIG. 22A-22B, the method further comprises optionally covering the device 126 with a sleeve 155 before positioning the device 126 in the patient. The sleeve 155 protects the surrounding tissues as the device 126 is moved through tissues and ultimately positioned into the space 116 made in the defect 102. The sleeve 155 is removed just prior to placement of the device 126 at the site of the defect 102 (e.g. before the orthopedic implant is positioned in the hole over a top of the central post). The sleeve 155 may be made of a transparent or semi-transparent material to facilitate visual orientation of the device and sleeve removal over the defect 102.

Figure 16O:
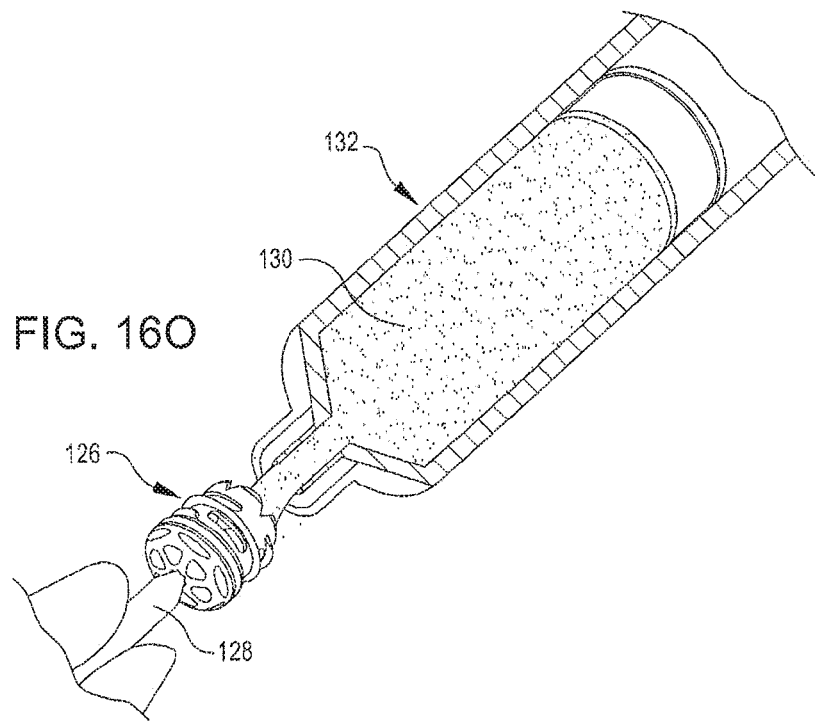

In one embodiment, the method further comprises injecting a biomaterial 130 such as a biologic material (i.e. stem cells or platelet-rich plasma, or both stem cells and platelet-rich plasma) into the first device 126 using an injector 132 as shown in FIG. 16O. In one embodiment, the method further comprises placing an insert according to the present invention in the first device 126 instead of injecting a biocompatible bone cement in the first device 126. In one embodiment, the insert is a biological material according to the present invention.

Figure 16P:
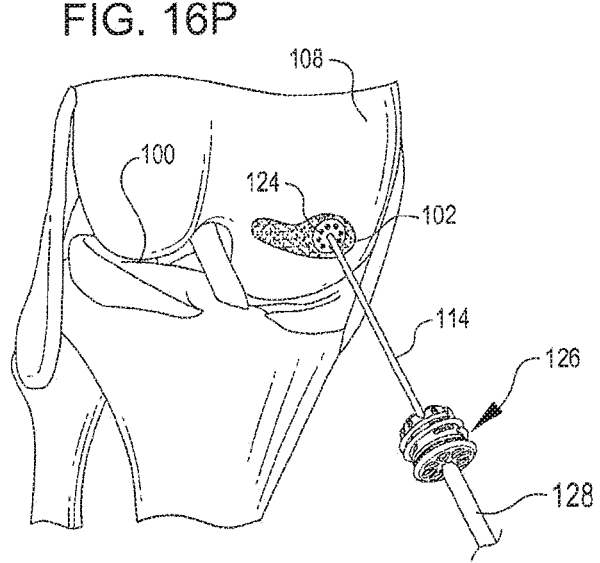
Figure 16Q:
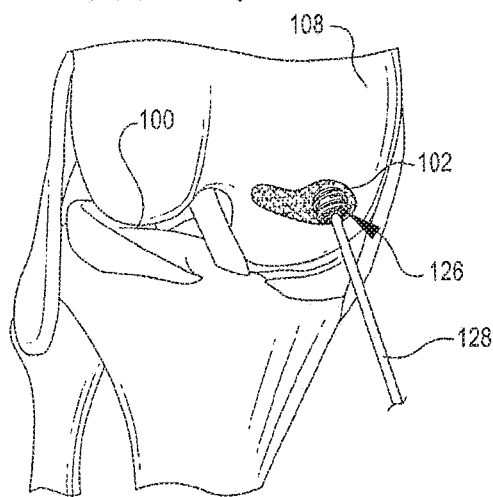
Figure 16R:
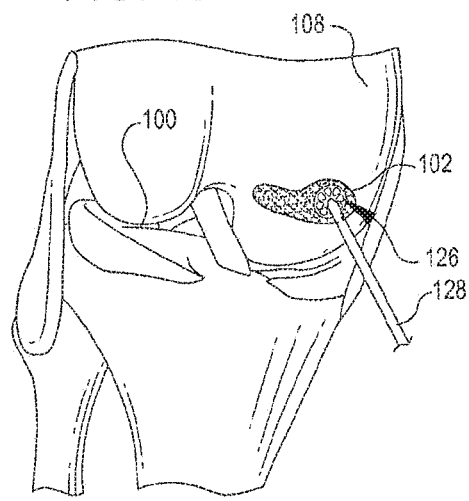
Figure 16S:
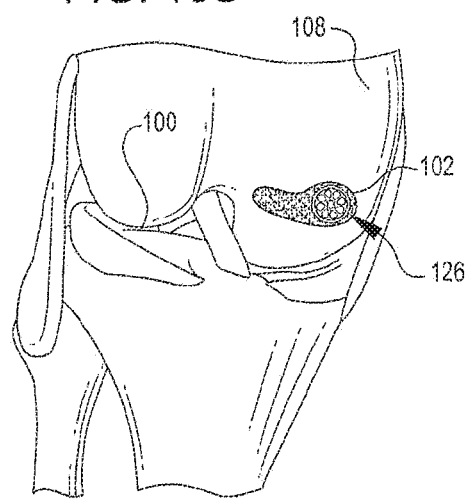
Figure 16T:
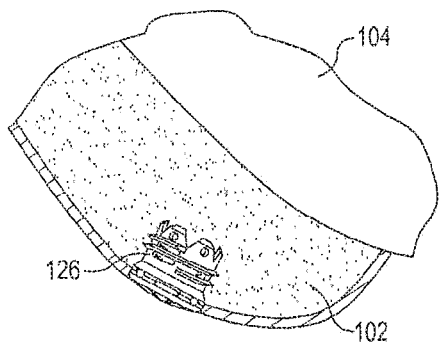
Figure 16T:
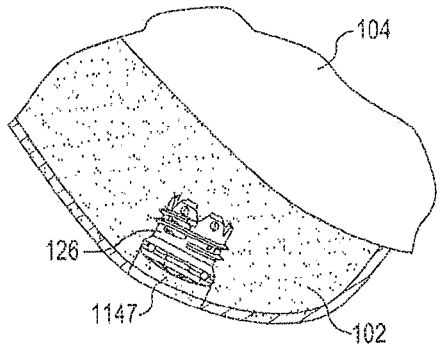
Figure 16T:
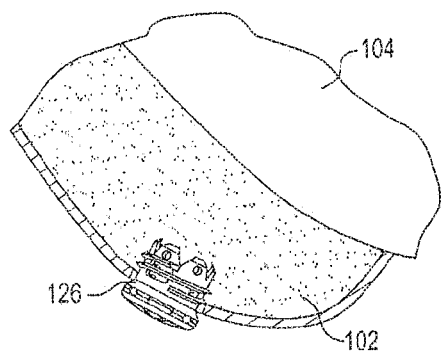

The method further comprises screwing the first device 126 into the space 116 using the driver 128, as shown in FIG. 16P through, FIG. 16S. FIGS. 16Ta-16Tc are partial, lateral cross-sections of the medial condyle 106 at the site of the defect 102 showing placement of the first device 126. As can be seen in FIG. 16Ta, the joint-ward end of the first device 126 forms a shape that substantially recreates the shape of a normal articulation surface on the bone after implantation. In this example the device is implanted substantially flush with a surface of the bone. This facilitates load-sharing. FIG. 16Tb alternatively shows the device 126 slightly countersunk below the surface of the bone with a carrier substance 1147 attached to the joint-ward end to facilitate tissue ingrowth, osteointegration, and healing. FIG. 16Tc alternatively shows the device 126 protruding slightly above the surface of the bone. This facilitates weight-bearing.

Figure 16U:
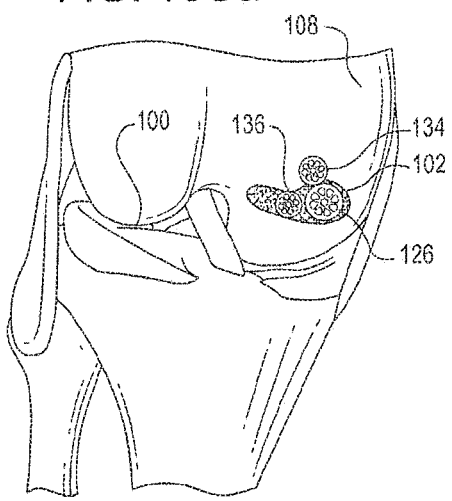
Figure 16U:
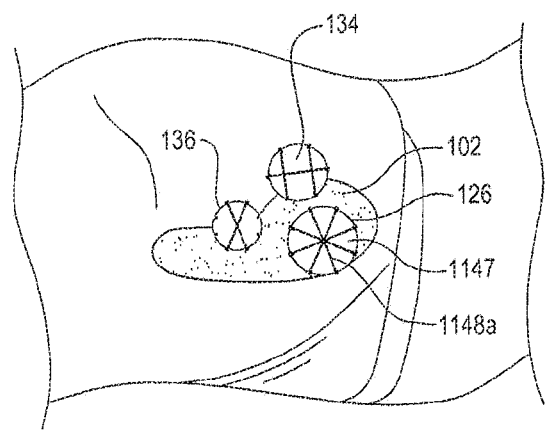
Figure 16U:
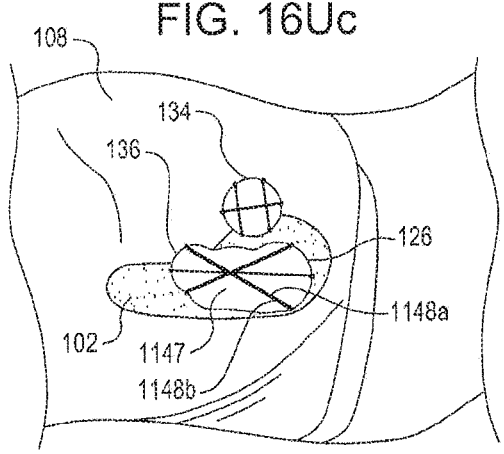
Figure 16U:
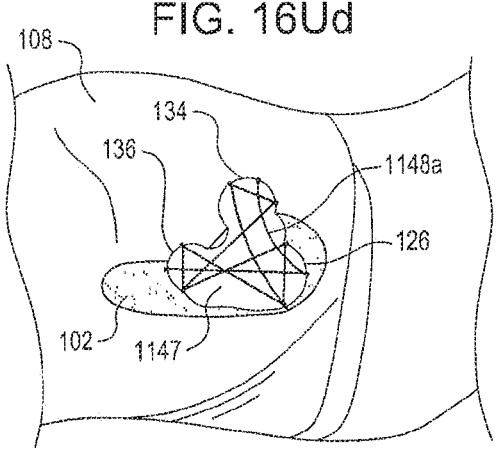
Figure 16U:
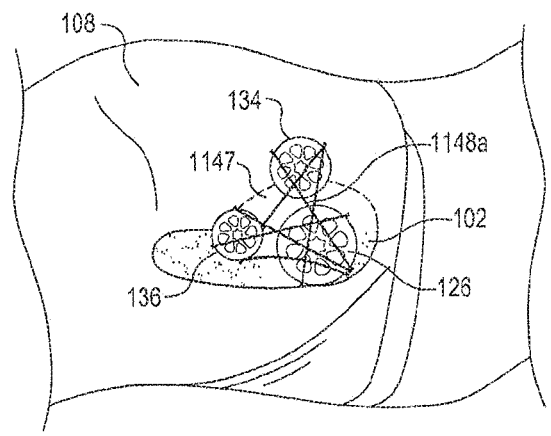

In one embodiment, as can be seen in FIG. 16Ua, the method further comprises placing one or more than one additional device 134, 136 in the defect 102. In one embodiment, the one or more than one additional device is one additional device. In another embodiment, one or more than one additional device is two additional devices. As will be understood by those with skill in the art with respect to this disclosure, the one or more than one additional device 134, 136 can be the same as the first device in terms of size and shape or can be different than the first device in terms of size and shape.

In another embodiment, a carrier substance containing a polymer, or biomaterial, or a hybrid combination thereof may be secured among and/or between more than one implantable orthopedic device. FIG. 16Ub is an enlarged version of FIG. 16Ua showing the devices 126, 134, 136 and defect 102. Devices 126, 134, 136 may be the same or different size versions of the device 10 embodied in FIGS. 11Ha-11Hc, for example. The carrier substance 1147 may be secured on the joint-ward end of each device before or after implantation as previously described. FIG. 16Ub shows the carrier substance 1147 individually secured among each of three different sized devices. FIG. 16Uc shows the carrier substance 1147 spanning an area between devices 126 and 136 with sutures 1148a, 1148b attached (e.g. tethered). In this example, the suture strands are shared with devices 126, 136 to secure the carrier substance 1147 in place over the defect 102 located generally between the devices 126, 136. An second carrier substance is separately secured to device 134. In another configured pattern as shown in FIG. 16Ud, the carrier substance 1147 is secured with sutures among and between devices 126, 134, 136 to cover the majority of the defect 102. In yet another embodiment, FIG. 16Ue shows the carrier substance 1147 secured between devices 126, 134, 136 with strands 1148a shared among the devices.

There are many combinations of suture threading patterns, anchor types and sizes, anchor placement locations, and deployment sequences that may be used to attach a carrier substance among and/or between more than one implantable device according to the methods and devices described herein. The carrier substance may include a mesh, substrate, washer, or pouch configuration and may be attached via sutures, staples, coatings, adhesives, or similar attachment to a threaded (FIG. 1Aa), press-fit (FIG. 12A) or smooth (FIG. 1Ab) implantable orthopedic device either before or after the device has been implanted into the bone. These variations as well as variations in the design of the above-described devices and instruments are within the scope of the present disclosure.

Figure 16V:
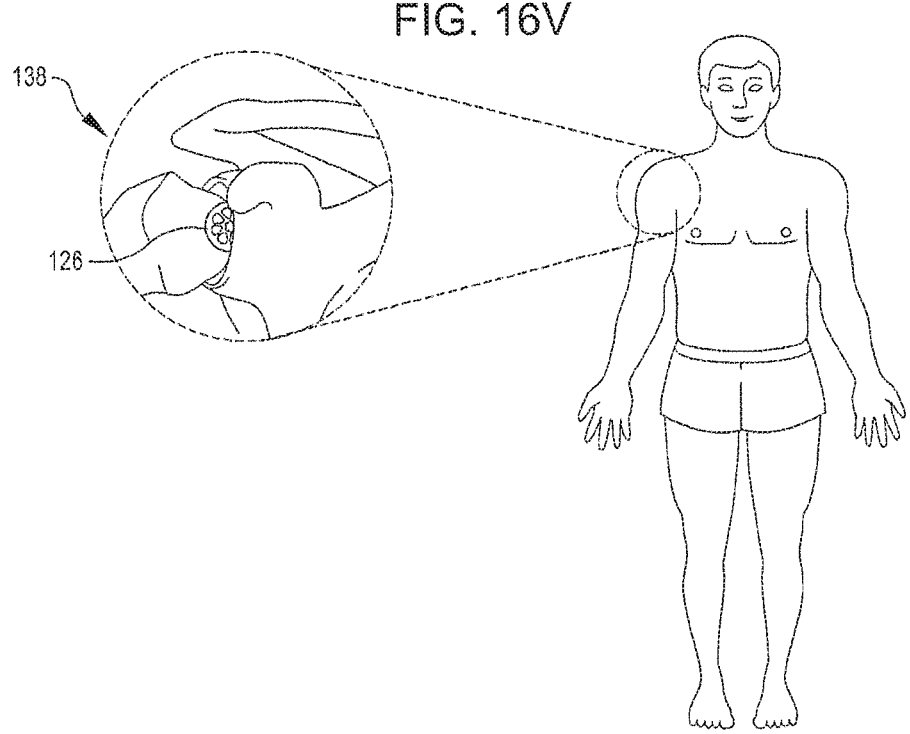

Though the method of the present invention has been disclosed with respect to a defect 102 in a femorotibial joint 100, corresponding methods can be used with other joints. FIG. 16V is a partial, lateral cross-section of a glenohumeral joint 138 at the site of a defect showing placement of a device 126 for repairing joint conditions according to the present invention.

Figure 17A:
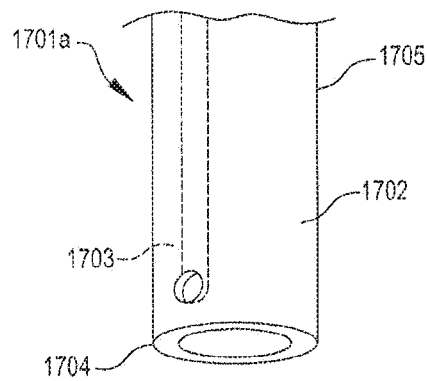
FIGS. 17A-17C are cross section diagrams showing embodiments of a device for repairing anatomical joint conditions according to the present invention.
Figure 17B:
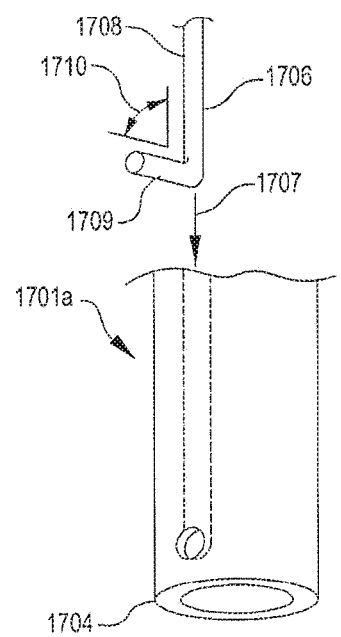
Figure 17C:
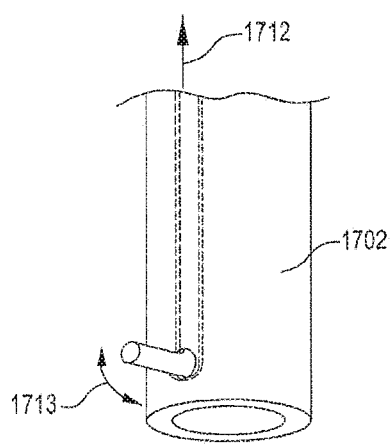
Figure 17D:
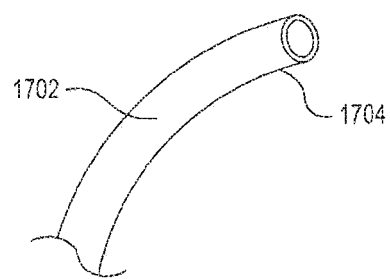
FIGS. 17D-17E are lateral perspective views of other embodiments of the present invention.
Figure 17E:
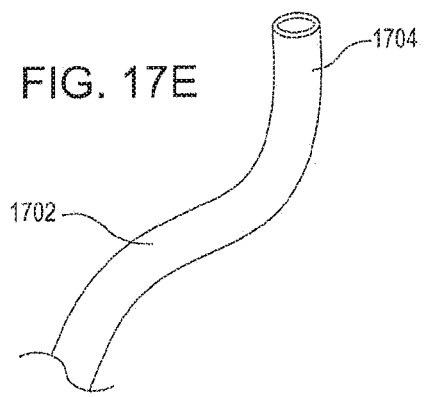

FIGS. 17A through 17C, show a cannula 1701a for arthroscopically retracting a target tissue at an anatomical joint. The cannula 1701a comprises a delivery tube 1702 with a distal end 1704, a proximal end 1705, and an elongate member disposed between the distal and proximal ends. A guided slot 1703 runs at least partially along a length of the elongate member and a rod-like retractor 1706B configured for movable insertion 1707 in the delivery tube along slot 1703. The retractor has a distal end 1709, a proximal end 1708, and an elongate section disposed between the distal and proximal ends. As shown in FIGS. 17B and 17C, the distal end 1709 of the retractor may be bent at an angle 1710 between about 1 degree and 179 degrees relative to the elongate section. When the cannula is used to retract target tissue at an anatomical joint, the distal end of the retractor is configured to movably track along the slot 1703 and engage and retract the target tissue in an substantially proximal direction relative to an axis of the delivery tube when a force 1712 is applied to the proximal end of the retractor. The distal end 1709 may be rotated about an axis 1713 to assist in engaging a target tissue. The delivery tube 1702 of the cannula 1701a may be bendable to conform to a number of shapes including a curved shape as shown in FIG. 17D, a sigmoid shape as shown in FIG. 17E, or any other shapes that assist in engaging and retracting a target tissue within a sometimes tortuous path within an anatomical joint space. The bendable configurations may be reversibly customizable via application of one or more directional forces along the delivery tube 1702.

Figure 17F:
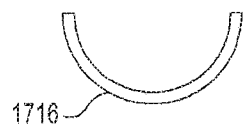
FIG. 17Fa is an cross section view of the distal end of a cannula according to other embodiments of the present invention.
Figure 17F:
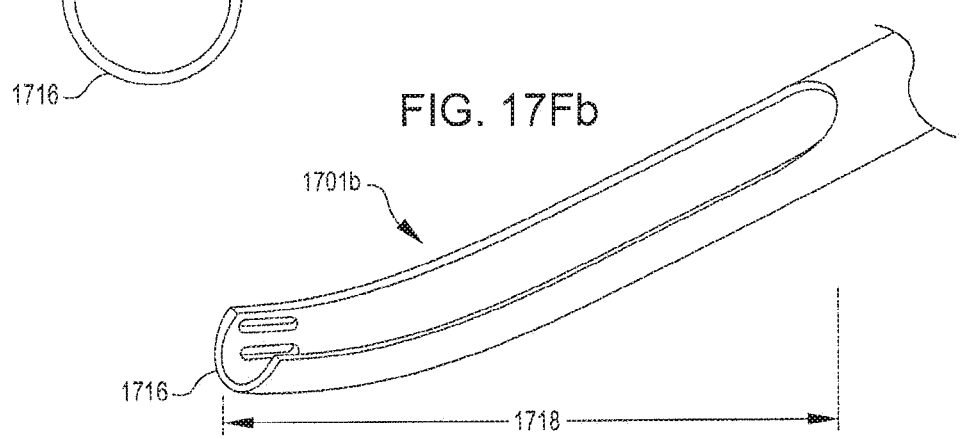
Figure 17G:
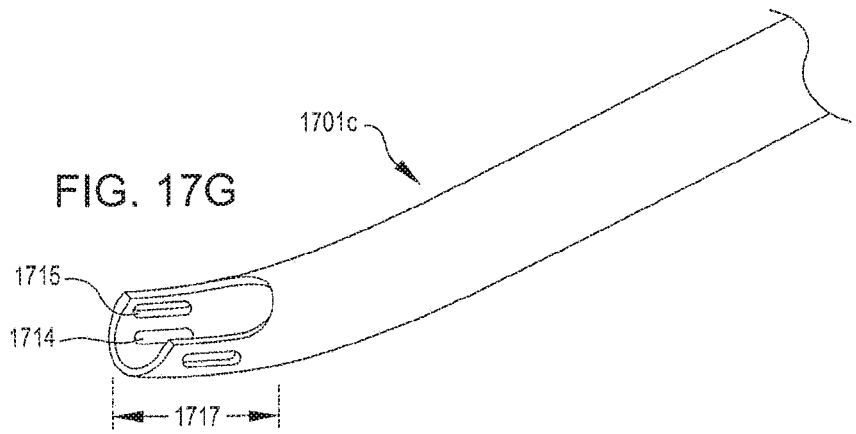
Figure 17H:
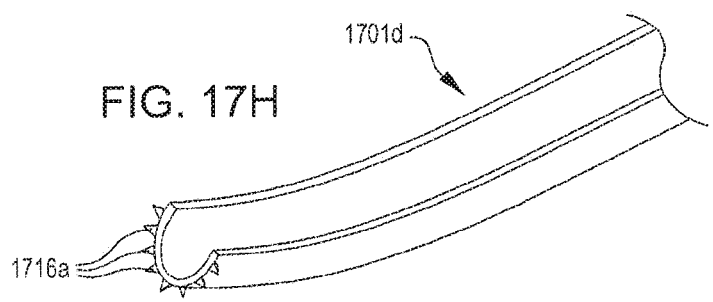

A cannula 1701b, 1701c with a "half pipe" design feature is shown in FIGS. 17Fa, 17Fb and 17G. The distal tip 1716 of the cannula is shaped like the letter "C" when viewed in cross section (FIG. 17Fa). The cannula 1701b may be a transparent material (e.g. clear plastic) as shown in FIG. 17Fb or the cannula 1701c may be an opaque material such as metal as depicted in FIG. 17G, for example. The shape of the cannula facilitates visualization of the implant as it is delivered to the defect. Openings 1714, 1715 may also serve this purpose. The half pipe feature may include only a few millimeters from the tip 1717 or run substantially along the entire length 1718 of the cannula 1701b. The cannula 1701d may also include teeth 1716a, as shown in FIG. 17H, to hold the cannula in place as the implant is delivered to the target tissue site. The cannula 1701a, 1701b, 1701c may be used with or without a guidewire.

Figure 18A:
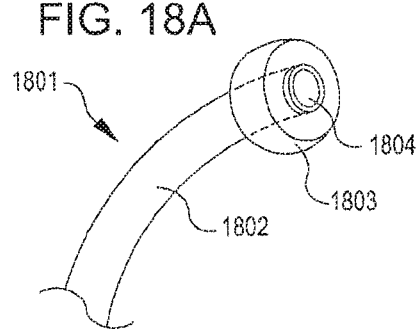
FIG. 18A is a lateral perspective view of an embodiment of the present invention.
Figure 18B:
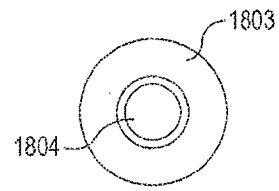
FIGS. 18B-18D are top perspective views of an embodiment of a device for repairing anatomical joint conditions according to the present invention.
Figure 18C:
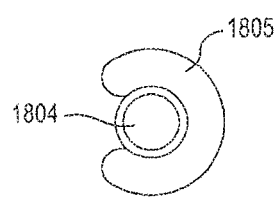
Figure 18D:
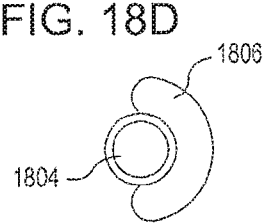

FIG. 18A is a lateral perspective view of an embodiment of the present invention. In this embodiment, the cannula 1802 includes an inflatable retractor preferably located near the distal end 1804 that may inflate around some 1806, most 1805 or all 1803 of the cannula 1802 as shown in cross section (FIGS. 18D, 18C and 18B), respectively. When the retractor is inflated, the target tissue is moved away from the defect 102 to allow enhanced access and visualization of the defect during reparation of the anatomical joint.

Figure 19A:
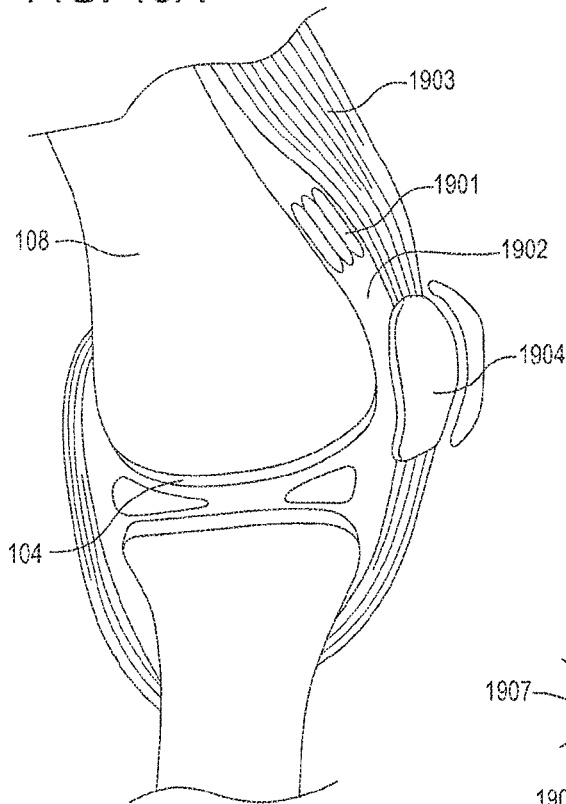
FIG. 19A is a side view perspective of a human knee joint showing an embodiment of the present invention.

FIG. 19A is a side view perspective of a human knee joint showing an embodiment of the present invention. As shown, an inflatable envelope 1901 has been arthroscopically inserted into a targeted space. In this example, the targeted space includes the suprapatellar pouch 1902 between the femur 108 and the quadriceps muscle 1903 near the human knee joint. Of course, the envelope 1901 may be inserted in any number of locations, including between the femur 108 and patella 1904, for example. When the envelope is inflated, it displaces tissue by inflation pressure to allow better access and visualization of the defect. The envelope may be inflated by a gas or liquid (i.e. saline solution), for example.

Figure 19B:
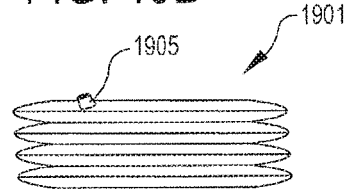
FIGS. 19B-19C are perspective views of an embodiment of a device for repairing anatomical joint conditions according to the present invention.
Figure 19C:
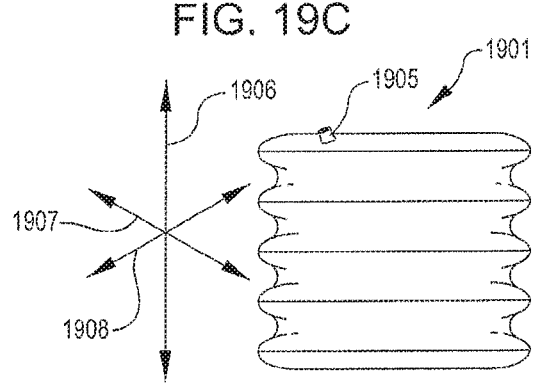

FIG. 19B shows the envelope in a deflated state prior to insertion. FIG. 19C shows the envelop inflated by introducing a gas or liquid through nozzle 1905. The envelope can be configured to inflate in many directions 1906, 1907, 1908. It is generally preferred to have the envelope to inflate primarily in direction 1906 to act as a type of "joint jack" (e.g. similar to a car jack elevating an automobile to aid in replacing a flat tire).

Figure 20A:
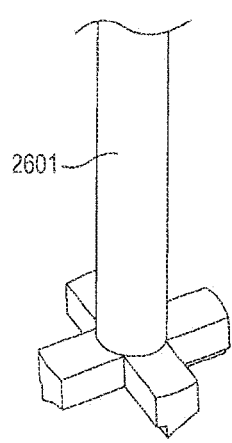
FIGS. 20A-20B and 20D are perspectives views of a countersink instrument per another embodiment of a device for repairing anatomical joint conditions according to the present invention.
Figure 20B:
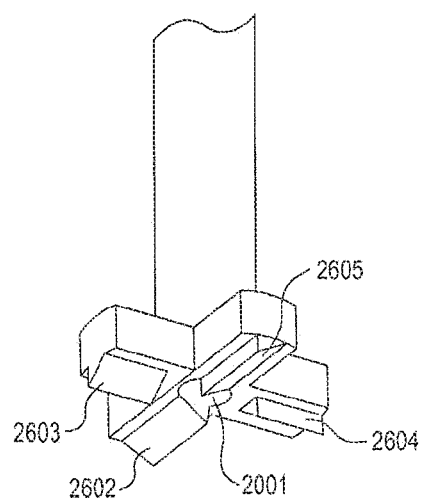
Figure 20C:
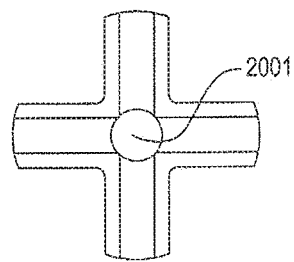
FIG. 20C is a bottom perspective view of a countersink instrument shown in FIGS. 39A-39B and 39D.
Figure 20D:
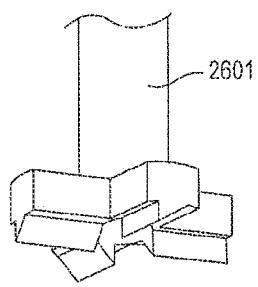
Figure 20E:
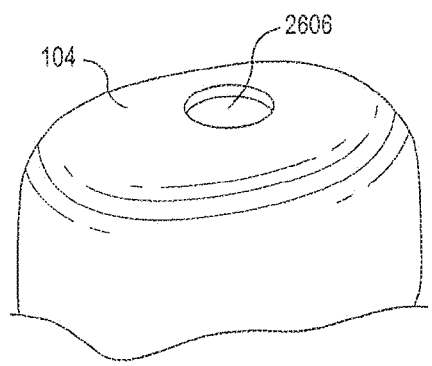
FIG. 20E is a perspective view of a countersink hole prepared in bone using the instrument in FIGS. 20A-20D.
Figure 20F:
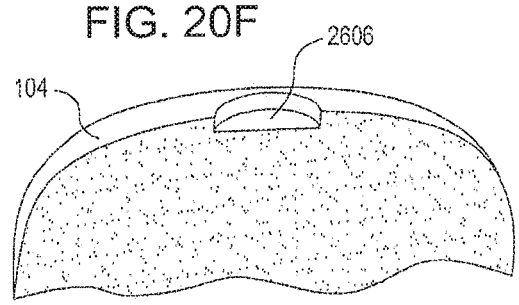
FIG. 20F is a cross section of a countersink hole prepared in bone using the instrument in FIGS. 20A-20D.

FIGS. 20A-20B and 20D are perspectives views of countersink instrument 2601 of another embodiment of a device for repairing anatomical joint conditions according to the present invention. Lumen 2001 provides for the insertion of the guidewire 114 in use. The countersink instrument 2610 may include 2 or more blades equally spaced apart from one another. FIGS. 20A-20D show 4 total blades 2602, 2603, 2604, 2605. FIG. 20C shows a bottom perspective view the countersink instrument shown in FIGS. 39A-39B and 39D. FIG. 20E is a perspective view of a countersink hole 2606 prepared in bone 104 using the countersink instrument 2601 in FIGS. 20A-20D. FIG. 20F is a cross section of a countersink hole 2606 prepared in bone 104 using the instrument 2601 shown in FIGS. 20A-20D. The countersink instrument 2601 is used to basically clear soft tissue and drill a countersink hole in the bone before using the cannulated drill.

Figure 21A:
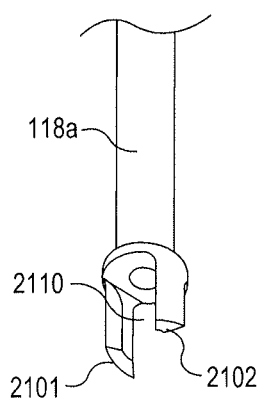
FIG. 21A is a perspective view of an embodiment of a cannulated drill for repairing anatomical joint conditions according to the present invention.
Figure 21B:
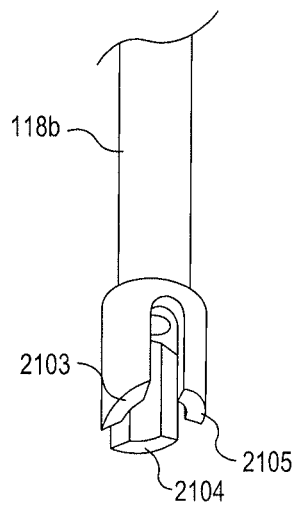
FIG. 21B is a perspective view of another embodiment of a cannulated drill as another embodiment of a device for repairing anatomical joint conditions according to the present invention.
Figure 21C:
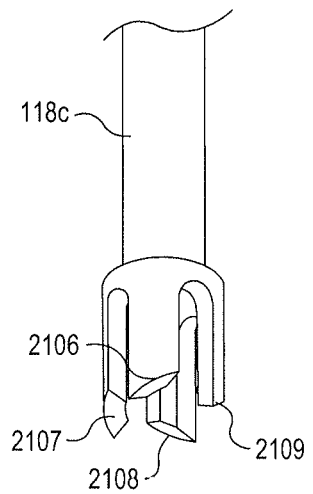
FIG. 21C is a perspective view of yet another embodiment of a cannulated drill for repairing anatomical joint conditions according to the present invention.
Figure 21D:
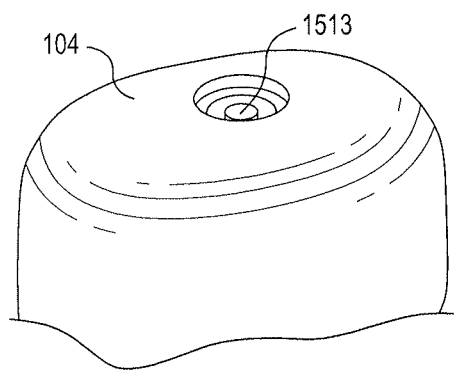
FIG. 21D is a perspective view of a hole and post prepared in bone using the instruments embodied in FIGS. 21A-21C.
Figure 21E:
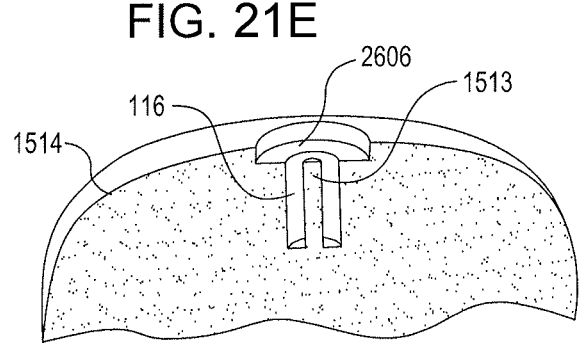
FIG. 21E is a cross section of a hole and post prepared in bone using the instruments embodied in FIGS. 21A-21C.

Turning now to FIG. 21A, a cannulated drill 118a includes 2 prongs (i.e. blades) 2101, 2102 spaced equally apart from each other. The cannulated drill 118c may have 4 prongs 2106, 2107, 2108, 2109 as shown in FIG. 21C. However, the 3 pronged 2103, 2104, 2105 cannulated drill 118b shown in FIG. 21B is preferred as it is more likely to drill a true hole without clogging bone into area 2110 between prongs, for example. The cannulated drill 118a, 118b, 118c removes bone 104 while leaving a center core 1513 of bone intact below the countersink hole 2606. This is shown in perspective view (FIG. 21D) and a cross sectional view (FIG. 21E) using the instruments in FIGS. 21A-21C. The countersink instrument 2601 and/or cannulated drill 118a, 118b, 118c may be made out of stainless steel, titanium or other materials commonly known in this technical field, for example.

FIG. 23A is a perspective view of a driver instrument 157 that reversibly engages an implantable orthopedic device 10. The device is configured to implant in a bone 102. The driver instrument 157 comprises a distal end 158 having a male configuration including a centrally-located threaded protuberance 159 and relatively shorter elongate knobs 160a, 160b, 160c. The knobs form a diameter around the protuberance 159. When the driver instrument 157 is aligned in proximity 161 with the implantable device 10, lowered 166 into position, and rotated 162 in one direction, the threaded protuberance 159 engages a mirror reverse female configuration 163 located on a joint-ward end 164 of the implantable device. Continued rotation 162 causes the knobs 160a, 160b, 160c to engage the corresponding female configuration 165a, 165b, 165c on the implantable device to provide sufficient leverage to implant the implantable orthopedic device 10 in the bone 102 as shown in FIG. 23B. Rotating the driver instrument in the opposite direction 168 allows the knobs 160a, 160b, and 160c and threaded protuberance 159 to disengage with the now implanted device 10 and the driver instrument 157 is removed from the area 169 as shown in FIG. 23C.

Figure 24A:
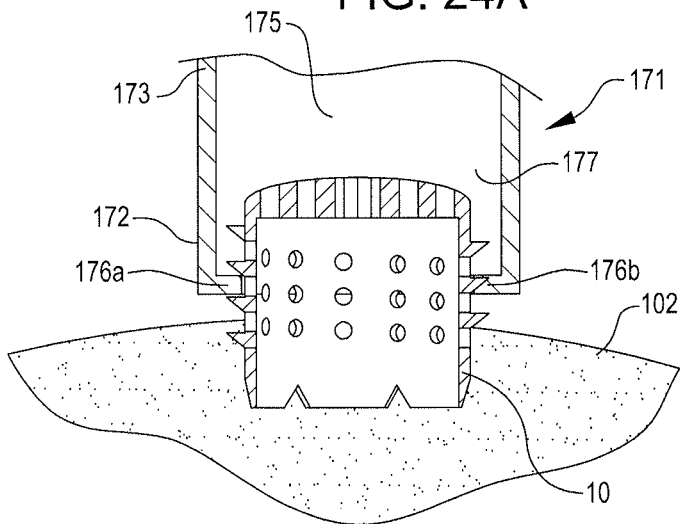
FIG. 24A is a cut-a-way side view of an extraction tool engaged with an implantable orthopedic device according to embodiments of the present invention.
Figure 24B:
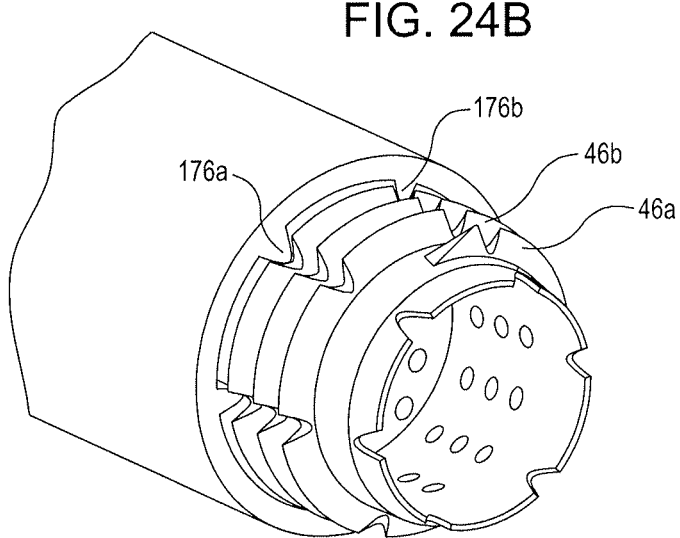
FIG. 24B is a perspective view of an extraction tool and an implantable orthopedic device according to embodiments of the present invention.
Figure 24C:
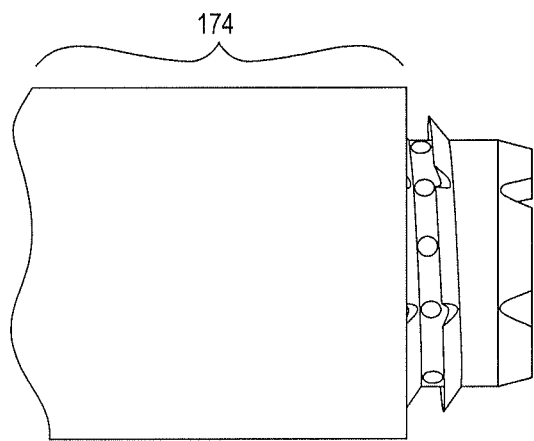
FIG. 24C is a side view of FIG. 24B after further engagement of the extraction tool with an implantable orthopedic device according to embodiments of the present invention.
Figure 25A:
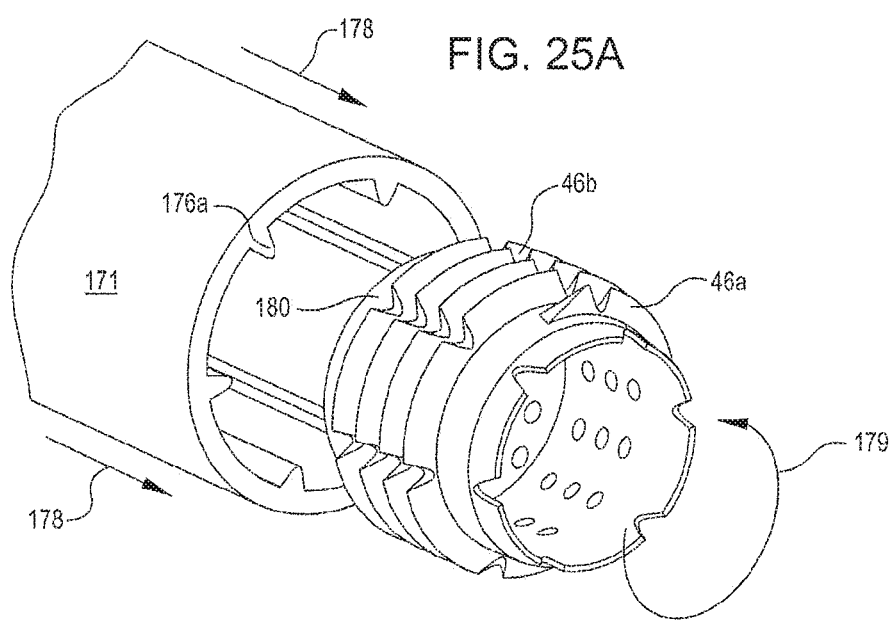
FIGS. 25A-25B are sequential perspective views of an extraction tool and an implantable orthopedic device according to embodiments of the present invention.
Figure 25B:
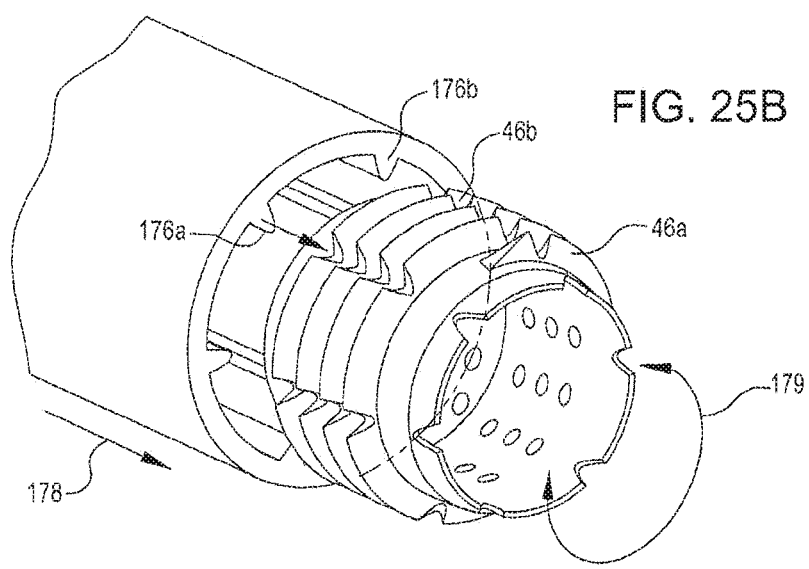
Figure 26:
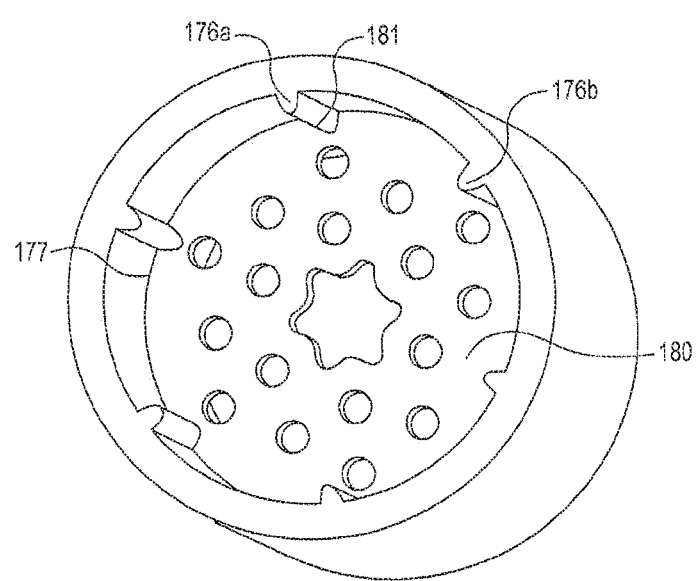
FIG. 26 is a cut-a-way perspective view from inside the extraction tool as it is placed over an exposed surface of the implantable orthopedic device according to embodiments of the present invention.

Turning now to FIG. 24A, an extraction tool 171 is shown in a cross sectional view. The extraction tool may be used for removing an orthopedic device 10 implanted in a bone 102. The extraction tool 171 comprises a distal end 172, a proximal end 173 and an elongate member 174 disposed between the distal end and the proximal end. The elongate member 174 includes a conduit 175 running at least along a length of the distal end 172. The conduit 175 includes two or more nubs 176a, 176b. Each nub is between about 0.5 and 1.5 mm in length. Preferably, each nub is about 0.9 mm in length. The nubs 176a, 176b project from an inside surface 177 of the conduit 175. As shown in FIGS. 24B and 25A-25B the nubs are configured to engage and slide past 178 corresponding notches 46b spaced vertically along thread 46a paths of the implantable orthopedic device 10 such that, when the extraction tool 171 is placed over an exposed surface 180 (e.g. a surface not implanted in bone) of the implantable orthopedic device 10, and the two or more nubs 176a, 176b engage 181 and slide 178 past the corresponding notches, the extraction tool 171 is rotated in either direction 179 to seat the notches between thread paths. Once seated, the extraction tool allows efficient leverage when twisting and/or pulling to remove the device from the bone in use. Once the device is removed from the bone, the extraction tool can be separated from the orthopedic device by rotating the extraction tool relative to the orthopedic device to unseat the nubs from between the thread paths and then aligning the nubs with the notches. Once the nubs are aligned with the notches, the extraction tool can be separated from the device by guiding the nubs along the vertically aligned notches in a direction away from the orthopedic device. In this manner, the extraction tool and orthopedic device may be separated.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. An implantable orthopedic device for repairing anatomical joints and ameliorating joint conditions at a treatment site of a human or animal, the device comprising:
   a) a first section comprising a joint-ward end, an opposing mating end, and a lateral wall extending between the joint-ward end and the mating end;
   where the first section further comprises a peripheral column partially forming the lateral wall of the first section and a central column at least partially within the peripheral column;
   where the joint-ward end comprises a plurality of fenestrations, where each fenestration is formed by a confluence of the peripheral column and the central column; and
   where the first section further comprises a central aperture within and formed by the central column, and configured to mate with an introducer; and
   b) a second section comprising a mating end, an opposing leading end, and a lateral wall extending between the mating end and the leading end, the lateral wall having an inner wall and an outer wall;
   where the lateral wall of the second section comprises protrusions on the inner wall, outer wall, or a combination thereof;
   where the leading end comprises an edge configured to be the first to penetrate a bone during implantation; and
   where the lateral wall of the second section further comprises a plurality of fenestrations between the protrusions;
   where the device has a width and a length, wherein the width and the length of the device comprises an aspect ratio of between about 0.3 and 3.0, respectively;
   wherein a washer is mechanically attachable atop the joint-ward end of the first section and opposite the opposing mating end, the washer having a geometry;
   wherein the washer is configured to be partially or completely absorbable over a period of time after the washer is attached to the device at the treatment site, the washer configured to promote guided tissue regeneration (GTR);
   wherein the central column includes a chamfer, the chamfer narrowing a diameter of the central column from a first diameter at a first distance from the leading edge to a second, smaller diameter at a second, greater distance from the leading edge so as to compact a central post of a bone when the implantable orthopedic device is placed in a hole over a top of the central post.

2. The device of claim 1, wherein the implantable orthopedic device is configured to be implanted in the bone at the treatment site and the bone is a subchondral bone;
   wherein the implantable orthopedic device includes a biomaterial;
   wherein the biomaterial comprises a biphasic material, wherein the biphasic material includes a solid component and non-solid component, further wherein the non-solid component is a gel, the gel having an elastomeric quality and a viscosity so as to sufficiently inhibit the gel from dripping off the device when the device is implanted at the treatment site;
   wherein the biomaterial further comprises a biocompatible material, a biocomposite material, a biomimetic material, a bioactive material, a nanomaterial, a partially absorbable material, a fully absorbable material, a tissue forming material, a replaceable material, a graft material, or any combination of the aforementioned materials, the biomaterial contained by a cover;
   wherein the viscosity is greater than about 1.0 mPa-s;
   wherein the viscosity is between about 1.5 mPa-s and 5.0 mPa-s; wherein the non-solid component of the biphasic material exhibits viscoelastic properties; and wherein the biomaterial includes an antimicrobial agent and/or a chemotherapeutic agent.

3. The device of claim 2, wherein the device is configured to accept and retain an amount of the biomaterial when the biomaterial is administered post-implantation or pre-implantation of the device and the amount is administered post-implantation via a needle injection, a fluoroscope guide, or an ultrasound guide; and further
   wherein a carrier substance is attached to the device and the carrier substance is a polymer, a polymer configured in a sponge matrix arrangement, or biomaterial, or medication, or a hybrid combination thereof;
   wherein the carrier substance is a biomaterial that includes cartilage, osteocartilage, platelet-rich plasma, a chemotactic substance or a cellular differentiation substance; and
   wherein the cellular differentiation substance includes stem cells or injectable mesenchymal stem cells (MSCs) configured to migrate to the device when the device is implanted at the treatment site.

4. The device of claim 2, further wherein the washer has a geometry comprising a convex, concave or flat profile as seen on a cross-sectional, lateral perspective view;
  wherein the washer geometry is configured in a bowl-shape to contain a biomaterial and promote tissue ingrowth at the treatment site and includes chambers to house a biomaterial and engage a tissue at the treatment site.

5. The device of claim 4, wherein the chambers have an overhanging lip portion configured to retain the biomaterial.

6. The device of claim 2, wherein the biomaterial comprises a porous material impregnated with a matrix-promoting substance, the substance supporting a population of progenitor cells.

7. The device of claim 1, wherein the anatomical joint is:
  (i) a mammalian hip, knee, ankle, shoulder, elbow, wrist, finger, toe, or spine;
  (ii) selected from the group consisting of an acetabulofemoral joint, an acromioclavicular joint, a femoropatellar joint, a femorotibial joint, a glenohumeral joint, a humeroradial joint, a humeroulnar joint, an interphalangeal joint, a metacarpal joint, a radioulnar joint and a talocrural joint; or
  (iii) a human knee joint, and wherein the condition is chosen from the group consisting of chondromalacia patella, isolated chondral defect, juvenile idiopathic arthritis, ligamentous deficiency arthroses, osteonecrosis, osteoarthritis, osteochondritis dissecans, patellar instability, post-ligamentous injury arthritis, post-meniscectomy arthritis, post-meniscectomy arthroses, post-traumatic arthritis, septic arthritis, rheumatoid arthritis, osteochondral defect, subchondral bone insufficiency, fracture, or overload (implying a pre-fracture state) and genetic defects.

8. The device of claim 1, wherein the plurality of fenestrations of the second section are variable sizes so as to provide support for different tissue types and promote healing repair at the treatment site;
  wherein the plurality of fenestrations between the protrusions on the second section of the lateral wall are between about 300 microns and 1200 microns in size to promote bone growth;
  wherein the plurality of fenestrations of the jointward end are pores, the pores sized about 800 microns in diameter to promote bone growth or sized about 500 microns in diameter to promote cartilage growth.

9. The device of claim 1, wherein an external surface of the device is at least partially textured to increase the surface area of the device to provide compressive, tensile; and/or shear stress attenuation enhancement at the treatment site;
  wherein the at least partial texture includes a dimpled pattern or a pattern within a pattern configuration; and
  wherein the external surface is a biomaterial, the biomaterial promoting tissue growth, tissue differentiation and/or tissue attraction.

10. The device of claim 1, wherein the mating end of the second section includes a non-threaded press-fit portion configured to substantially seal out synovial fluid; and
  wherein the device includes a blind-ended central aperture which extends only partially through the joint-ward end of the device such that synovia leakage is mitigated or prevented.

11. The device of claim 1, wherein the protrusions are threads; and wherein the width and the length of the device comprises an aspect ratio of between about 0.3 and 2.0, respectively.

12. The device of claim 1,
  wherein loading of the central post is increased and/or resorption of the central post is decreased when the central post of the bone is compacted; and
  wherein the chamfer includes an angle of about 45 degrees and inhibits formation of bone cysts and/or bone spurs.

13. An implantable orthopedic device for repairing anatomical joints and ameliorating joint conditions at a treatment site of a human or animal, the device comprising:
  a) a first section comprising a joint-ward end, an opposing mating end, and a lateral wall extending between the joint-ward end and the mating end;
  where the first section further comprises a peripheral column partially forming the lateral wall of the first section and a central column at least partially within the peripheral column;
  where the joint-ward end comprises a plurality of fenestrations, where each fenestration is formed by a confluence of the peripheral column and the central column; and
  where the first section further comprises a central aperture within and formed by the central column, and configured to mate with an introducer; and
  b) a second section comprising a mating end, an opposing leading end, and a lateral wall extending between the mating end and the leading end, the lateral wall having an inner wall and an outer wall;
  where the lateral wall of the second section comprises protrusions on the inner wall, outer wall, or a combination thereof;
  where the leading end comprises an edge configured to be the first to penetrate a bone during implantation; and
  where the lateral wall of the second section further comprises a plurality of fenestrations between the protrusions;
  where the device has a width and a length, wherein the width and the length of the device comprises an aspect ratio of between about 0.3 and 3.0, respectively;
  wherein a washer is mechanically attachable atop the joint-ward end of the first section and opposite the opposing mating end, the washer having a geometry;
  wherein the washer is configured to be partially or completely absorbable over a period of time after the washer is attached to the device at the treatment site, the washer configured to promote guided tissue regeneration (GTR);
  wherein the lateral wall of the second section includes one or more vascular grooves extending from the mating end to the leading end and providing a surface area for blood adhesion to facilitate blood wicking toward the joint-ward end and the treatment site.

14. The device of claim 13,
  wherein the one or more vascular grooves extend in a substantially parallel configuration or a substantially spring-shaped configuration to encourage blood flow capillarity and discourage blood flow turbulence.

15. An implantable orthopedic device for repairing anatomical joints and ameliorating joint conditions at a treatment site of a human or animal, the device comprising:
  a) a first section comprising a joint-ward end, an opposing mating end, and a lateral wall extending between the joint-ward end and the mating end;
  where the first section further comprises a peripheral column partially forming the lateral wall of the first section and a central column at least partially within the peripheral column;

where the joint-ward end comprises a plurality of fenestrations, where each fenestration is formed by a confluence of the peripheral column and the central column; and
where the first section further comprises a central aperture within and formed by the central column, and configured to mate with an introducer; and
b) a second section comprising a mating end, an opposing leading end, and a lateral wall extending between the mating end and the leading end, the lateral wall having an inner wall and an outer wall;
where the lateral wall of the second section comprises protrusions on the inner wall and on the outer wall;
where the leading end comprises an edge configured to be the first to penetrate a bone during implantation;
where the lateral wall of the second section further comprises a plurality of fenestrations between the protrusions;
where the device has a width and a length, wherein the width and the length of the device comprises an aspect ratio of between about 0.3 and 3.0, respectively;
wherein a washer is mechanically attachable atop the joint-ward end of the first section and opposite the opposing mating end, the washer having a geometry;
wherein the washer is configured to be partially or completely absorbable over a period of time after the washer is attached to the device at the treatment site, the washer configured to promote guided tissue regeneration (GTR);
wherein the protrusions on the inner wall extend from the inner wall and extend at least partially toward a central longitudinal axis of the device;
wherein the protrusions on the outer wall extend from the outer wall and extend at least partially away from the central longitudinal axis of the device;
wherein the protrusions on the inner wall and the protrusions on the outer wall are both configured to engage bone as the device is implanted at a treatment site.

16. The device of claim 15, wherein the lateral wall of the second section has a taper from the mating end to the leading end;
wherein the outer wall of the lateral wall of the second section has a taper of between about 1.0 degree and 9.0 degrees from the mating end to the leading end;
wherein the inner wall of the lateral wall of the second section has a taper of between about 1.0 degree and 9.0 degrees from the mating end to the leading end;
wherein the protrusions include a variable thread pitch design or a consistent thread pitch design;
wherein the threads are chosen from the group consisting of reverse cutting threads, notched threads, tapered threads, buttress threads, metric threads, trapezoidal threads, acme threads, pipe straight threads, unified threads, custom threads and multi-threads; and
wherein the tapered threads are configured to constantly purchase new bone to minimize strip out and increase holding power at the treatment site.

17. An implantable orthopedic device for repairing anatomical joints and ameliorating joint conditions at a treatment site of a human or animal, the device comprising:
a) a first section comprising a joint-ward end, an opposing mating end, and a lateral wall extending between the joint-ward end and the mating end;
where the first section further comprises a peripheral column partially forming the lateral wall of the first section and a central column at least partially within the peripheral column;
where the joint-ward end comprises a plurality of fenestrations, where each fenestration is formed by a confluence of the peripheral column and the central column; and
where the first section further comprises a central aperture within and formed by the central column, and configured to mate with an introducer; and
b) a second section comprising a mating end, an opposing leading end, and a lateral wall extending between the mating end and the leading end, the lateral wall having an inner wall and an outer wall;
where the lateral wall of the second section comprises protrusions on the inner wall, outer wall, or a combination thereof;
where the leading end comprises an edge configured to be the first to penetrate a bone during implantation; and
where the lateral wall of the second section further comprises a plurality of fenestrations between the protrusions;
where the device has a width and a length, wherein the width and the length of the device comprises an aspect ratio of between about 0.3 and 3.0, respectively;
wherein a washer is mechanically attachable atop the joint-ward end of the first section and opposite the opposing mating end, the washer having a geometry;
wherein the washer is configured to be partially or completely absorbable over a period of time after the washer is attached to the device at the treatment site, the washer configured to promote guided tissue regeneration (GTR);
wherein the lateral wall of the second section comprises a plurality of flares extending below the first section, the flare(s) configured to resist subsidence within the bone at the treatment site;
wherein the plurality of flares are arranged in a helical flare configuration and comprise at least two helical flares aligned along a helical path and separated from one another by at least one gap located in the helical path.

18. The device of claim 17, wherein:
the helical flare configuration includes an angle of more than 45 degrees;
the plurality of flares is configured to self-lock; or
the plurality of flares further comprises a tapered flare, a notched flare, or a barbed flare configuration.

19. An implantable orthopedic device for repairing anatomical joints and ameliorating joint conditions at a treatment site of a human or animal, the device comprising:
a) a first section comprising a joint-ward end, an opposing mating end, and a lateral wall extending between the joint-ward end and the mating end;
where the first section further comprises a peripheral column partially forming the lateral wall of the first section and a central column at least partially within the peripheral column;
where the joint-ward end comprises a plurality of fenestrations, where each fenestration is formed by a confluence of the peripheral column and the central column; and
where the first section further comprises a central aperture within and formed by the central column, and configured to mate with an introducer; and
b) a second section comprising a mating end, an opposing leading end, and a lateral wall extending between the mating end and the leading end, the lateral wall having an inner wall and an outer wall;

where the lateral wall of the second section comprises protrusions on the inner wall, outer wall, or a combination thereof;
where the leading end comprises an edge configured to be the first to penetrate a bone during implantation; and
where the lateral wall of the second section further comprises a plurality of fenestrations between the protrusions;
where the device has a width and a length, wherein the width and the length of the device comprises an aspect ratio of between about 0.3 and 3.0, respectively;
wherein the central column includes a chamfer, the chamfer narrowing a diameter of the central column from a first diameter at a first distance from the leading edge to a second, smaller diameter at a second, greater distance from the leading edge so as to compact a central post of a bone when the implantable orthopedic device is placed in a hole over a top of the central post;
wherein the lateral wall of the second section includes one or more vascular grooves extending from the mating end to the leading end and providing a surface area for blood adhesion to facilitate blood wicking toward the joint-ward end and the treatment site;
wherein the protrusions on the inner wall extend from the inner wall and extend at least partially toward a central longitudinal axis of the device;
wherein the protrusions on the outer wall extend from the outer wall and extend at least partially away from the central longitudinal axis of the device;
wherein the protrusions on the inner wall and the protrusions on the outer wall are both configured to engage bone as the device is implanted at a treatment site;
wherein the lateral wall of the second section comprises a plurality of flares defined at least in part by the protrusions on the outer wall, the plurality of flares extending below the first section, the flare(s) configured to resist subsidence within the bone at the treatment site;
wherein the plurality of flares are arranged in a helical flare configuration and comprise at least two helical flares aligned along a helical path and separated from one another by at least one gap located in the helical path;
further wherein a washer is attachable atop the joint-ward end of the first section and opposite the opposing mating end, the washer having a geometry;
wherein the washer is configured to be partially or completely absorbable over a period of time after the washer is attached to the device at the treatment site, the washer configured to promote guided tissue regeneration (GTR).

20. The device of claim 19, wherein the washer geometry comprises a convex, concave or flat profile as seen on a cross-sectional, lateral perspective view;
wherein the washer geometry is configured in a bowl-shape to contain a biomaterial and promote tissue ingrowth at the treatment site and includes chambers to house a biomaterial and engage a tissue at the treatment site;
wherein the washer geometry is independently customizable and configured to match a topography of the bone at the treatment site; or
wherein the attachable washer includes a threaded attachment, a spiked attachment, a slide-lock attachment, a snap-fit attachment or a notched attachment.

21. A kit for repairing an anatomical joint, the kit comprising: the implantable orthopedic device of claim 1;
a sizing instrument;
a guidewire;
a countersink instrument;
a cannulated drill;
a drill bit guide;
a drill bit;
a sleeve a driver instrument;
an injector;
an inflatable envelope;
at least one biomaterial;
instructions for use; and
a package holding the implantable orthopedic device, the sizing instrument, the guidewire, the countersink instrument, the cannulated drill, the drill bit guide, the drill bit, the sleeve, the driver instrument, the injector, the inflatable envelope, the at least one biomaterial, and the instructions for use; and
wherein the kit is sterilizable.

22. A method of attaching a carrier substance to a bone defect, comprising:
positioning a first implantable orthopedic device comprising the device of claim 1 substantially near the bone defect;
providing a length of strand material, the material having a first end and a second end;
threading the first end through a first fenestration of the plurality of fenestrations of the lateral wall;
wherein the first end exits through a second fenestration of the plurality of fenestrations of the lateral wall;
the first and second fenestrations in vertical alignment with one another;
securing the first end to the device; placing the carrier substance substantially near or in contact with the joint-ward end of the device, the carrier substance having therapeutic properties;
looping the second end of strand material across the carrier substance;
threading the second end through a third fenestration of the plurality of fenestrations of the lateral wall;
the third fenestration opposite or adjacent to the first fenestration;
wherein the second end exits through a fourth fenestration of the plurality of fenestrations of the lateral wall;
the third and fourth fenestrations in vertical alignment with one another;
pulling the second end of the length of strand material taut across the carrier substance; and
securing the second end to the device so as to tether the carrier substance near the joint-ward end of the device;
wherein the carrier substance and/or one or more strands may be secured pre- or post-implantation of the implantable device.

23. A method of securing a carrier substance to a bone defect, comprising: positioning a first implantable orthopedic device comprising the device of claim 1 substantially near the bone defect at a first location;
positioning a second implantable orthopedic device comprising the device of claim 1 substantially near the bone defect at a second location, the first and second locations being different locations;
placing the carrier substance substantially near or in contact with the joint-ward end of the first and second devices, the carrier substance spanning a contiguous area between the first and second devices across the bone defect;
providing a length of strand material, the material having a first end and a second end;

threading the first end through a first fenestration of the plurality of fenestrations of the lateral wall in the first device;
wherein the first end exits through a second fenestration of the plurality of fenestrations of the lateral wall in the first device;
securing the first end to the first device; looping the second end of a strand material across the carrier substance;
threading the second end through a first fenestration of the plurality of fenestrations of the lateral wall in the second device;
wherein the second end exits through a second fenestration of the plurality of fenestrations of the lateral wall in the second device;
pulling the second end of the length of suture material taut across the carrier substance; and
securing the second end to the second device so as to tether the carrier substance between the devices;
wherein the carrier substance comprises a polymer, or biomaterial, or medicine, or a combination thereof; and
wherein the fenestrations of at least one of the devices are vertically aligned with each other along the lateral wall.

* * * * *